US011464789B2

(12) United States Patent
Barbut et al.

(10) Patent No.: US 11,464,789 B2
(45) Date of Patent: Oct. 11, 2022

(54) AMINOSTEROL COMPOSITIONS AND METHODS OF USING THE SAME FOR TREATING SCHIZOPHRENIA

(71) Applicant: Enterin, Inc., Philadelphia, PA (US)

(72) Inventors: Denise Barbut, Philadelphia, PA (US); Michael Zasloff, Philadelphia, PA (US)

(73) Assignee: Enterin, Inc., Philadelphia, PA (US)

(*) Notice: Subject to any disclaimer, the term of this patent is extended or adjusted under 35 U.S.C. 154(b) by 0 days.

(21) Appl. No.: 16/530,093

(22) Filed: Aug. 2, 2019

(65) Prior Publication Data

US 2020/0155574 A1 May 21, 2020

Related U.S. Application Data

(60) Provisional application No. 62/714,470, filed on Aug. 3, 2018, provisional application No. 62/714,468, filed on Aug. 3, 2018, provisional application No. 62/789,438, filed on Jan. 7, 2019.

(51) Int. Cl.
*A61K 31/575* (2006.01)
*A61P 25/18* (2006.01)
*A61K 9/00* (2006.01)

(52) U.S. Cl.
CPC .......... *A61K 31/575* (2013.01); *A61K 9/0043* (2013.01); *A61K 9/0053* (2013.01); *A61P 25/18* (2018.01)

(58) Field of Classification Search
CPC .. A61K 31/575; A61K 9/0043; A61K 9/0053; A61P 25/18
See application file for complete search history.

(56) References Cited

U.S. PATENT DOCUMENTS

| | | | |
|---|---|---|---|
| 5,192,756 | A | 3/1993 | Zasloff et al. |
| 5,840,936 | A | 11/1998 | Zasloff et al. |
| 6,020,310 | A | 2/2000 | Beck et al. |
| 6,143,738 | A | 11/2000 | Zasloff |
| 6,962,909 | B2 | 11/2005 | Zasloff et al. |
| 10,040,817 | B2 | 8/2018 | Zasloff et al. |
| 2008/0058300 | A1 | 3/2008 | McLane et al. |
| 2009/0028816 | A1 | 1/2009 | Sultzbaugh et al. |
| 2013/0217707 | A1 | 8/2013 | Faraone |
| 2013/0281388 | A1 | 10/2013 | Deaver et al. |
| 2015/0368290 | A1 | 12/2015 | Zasloff |
| 2016/0303159 | A1 | 10/2016 | Lopes Da Silva |
| 2017/0326156 | A1 | 11/2017 | Zasloff et al. |
| 2017/0340623 | A1 | 11/2017 | Charmot et al. |
| 2018/0002370 | A1 | 1/2018 | Zasloff et al. |
| 2018/0133230 | A1 | 5/2018 | Zasloff et al. |
| 2019/0091241 | A1 | 3/2019 | Barbut et al. |
| 2019/0321367 | A1 | 10/2019 | Erickson et al. |
| 2019/0381071 | A1 | 12/2019 | Zasloff et al. |

FOREIGN PATENT DOCUMENTS

| | | | |
|---|---|---|---|
| WO | WO 1996/040728 A2 | 12/1996 |
| WO | WO 2006/119211 A2 | 11/2006 |
| WO | WO 2015/200195 A1 | 12/2015 |
| WO | WO 2019/241503 A1 | 12/2019 |

OTHER PUBLICATIONS

Birtwistle et al., Role of dopamine in schizophrenia and Parkinson's disease. British J. Nursing, vol. 7(14), Abstract (Year: 2013).*
Ghanemi, Schizophrenia and Parkinson's disease: Selected therapeutic advances beyond the dopaminergic etiologies. Alexandria J. Medicine, vol. 49, pp. 287-291 (Year: 2013).*
Office Action issued in co-pending U.S. Appl. No. 16/530,147, dated Apr. 24, 2020.
Non-Final Office Action issued on co-pending U.S. Appl. No. 16/530,295, dated Jan. 15, 2021.
Non-Final Office Action issued on U.S. Appl. No. 16/530,051, dated Jan. 8, 2021.
Non-Final Office Action issued on co-pending U.S. Appl. No. 16/530,127, dated Jan. 8, 2021.
T. Ehrenfeld ("Depression Can Make You Hear Voices Many depressed people hide their psychosis from doctors." Psychology Today, https://www.psychologytoday.com/us/blog/open-gently/201610/depression-can-make-you-hear-voices (2016).
Non-Final Office Action issued on U.S. Appl. No. 16/530,200, dated Jan. 15, 2021.
Non-Final Office Action issued on U.S. Appl. No. 16/530,138, dated Jan. 25, 2021.
Thorve, et al., "Diabetes-induced erectile dysfunction: epidemiology, pathophysiology and management," *Journ. of Diabetes and Its Complications*, vol. 25, pp. 129-136 (2011).
Thompson, et al., "Pharmacological Inhibition of Protein Tyrosine Phosphatase 1B Protects Against Atherosclerotic Plaque Formation in the LDLR—Mouse Model of Atherosclerosis," *Clinical Science*, vol. 131, pp. 2489-2501 (2017).
Smith, et al., "The Protein Tyrosine Phosphatase 1B Inhibitor MSI-1436 Stimulates Regeneration of Heart and Multiple other Tissues," *NJP Regenerative Medicine*, vol. 2, No. 4, pp. 1-10 (Mar. 2017).
Wade, et al., "Protein Tyrosine Phosphatases in Cardiac Physiology and Pathophysiology," *Heart Failure Reviews*, vol. 23, pp. 261-272 (Feb. 2018).
Office Action issued in co-pending U.S. Appl. No. 16/530,147, dated Feb. 18, 2020.
Bhargava et al., "A phase I and pharmacokinetic study of squalamine, a novel antiangiogenic agent, in patients with advanced cancers," *Clin. Cancer Res.*, 7:3912-9 (2001).
Hao et al., "A Phase I and pharmacokinetic study of squalamine, an aminosterol angiogenesis inhibitor," *Clin. Cancer Res.*, 9:2465-71 (2003).
Perni et al., "A natural product inhibits the initiation of alpha-synuclein aggregation and suppresses its toxicity," *PNAS, USA*, 114:E1009-E17 (2017).

(Continued)

*Primary Examiner* — Barbara P Badio
(74) *Attorney, Agent, or Firm* — Foley & Lardner LLP

(57) ABSTRACT

The present application relates generally to methods for treating, preventing and/or slowing the onset or progression of schizophrenia and/or a related symptom. The methods comprise administering at least one aminosterol or a pharmaceutically acceptable salt or derivative thereof to a subject in need.

23 Claims, 13 Drawing Sheets

(56) References Cited

OTHER PUBLICATIONS

International Search Report and Written Opinion issued in International Patent Application No. PCT/US2019/044882, dated Nov. 26, 2019.
International Search Report and Written Opinion issued in International Patent Application No. PCT/US2019/44917, dated Oct. 24, 2019.
Albert et al., "The Diagnosis of Mild Cognitive Impairment Due to Alzheimer's Disease: Recommendations from the National Institute on Aging—Alzheimer's Association Workgroups on Diagnostic Guidelines for Alzheimer's Disease," *Alzheimer's & Dementia*, 7(3):270-279 (2011).
Braak et al., "Idiopathic Parkinson's disease: possible routes by which vulnerable neuronal types may be subject to neuroinvasion by an unknown pathogen," *J. Neural. Transm. (Vienna)*, 110:517-36 (2003).
Braak et al., "Staging of brain pathology related to sporadic Parkinson's disease," *Neurobiol. Aging*, 24:197-211 (2003).
Breen et al., "Sleep and circadian rhythm regulation in early Parkinson disease," *JAMA Neurol.*, 71:589-95 (2014).
Breen, D.P. & Lang, A.E., "Tracking the Course of Prodromal Parkinson's Disease," *Brain*, 140:259-262 (2017).
Friedman JH, Akbar U., "Psychosis in Parkinson's disease: unexplained observations in a seemingly simple model," *Expert Rev. of Neurotherapeutics*, 16:595-6 (2016).
Holmqvist et al., "Direct evidence of Parkinson pathology spread from the gastrointestinal tract to the brain in rats," *Acta Neuropathol.*, 128:805-820 (2014).
Hughes et al., "Associations of Probable REM Sleep Behavior Disorder, Constipation, and Hyposmia with PD" (2017), 3 pages.
Lin et al., "Risk of Parkinson's disease following severe constipation: a nationwide population-based cohort study," *Parkinsonism Relat. Disord.*, 20:1371-5 (2014).
Madrid-Navarro et al., "Multidimensional Circadian Monitoring by Wearable Biosensors in Parkinson's Disease," *Front. Neurol.*, 9:157 (2018).
Marsili et al., "Diagnostic Criteria for Parkinson's Disease: From James Parkinson to the Concept of Prodromal Disease," *Front. Neurol.*, Online Mar. 23, 2018.
Mearin et al., "Bowel Disorders," *Gastroenterology*, 150(6):1393-1407 (2016).
Pagano, G., "Imaging in Parkinson's Disease," *Clin. Med.*, 16:371-375 (2016).
Palsetia et al., "The Clock Drawing Test versus Mini-mental Status Examination as a Screening Tool for Dementia: A Clinical Comparison," *Indian J. Psychol. Med.*, 40:1-10 (2018).
Rocca et al., "The Role of I 1-Weighted Derived Measures or Neurodegeneration for Assessing Disability Progression in Multiple Sclerosis," *Front Neurol.*, 8:433 (Sep. 4, 2017).
Stolzenberg et al., "A Role for Neuronal Alpha-Synuclein in Gastrointestinal Immunity," *J. Innate Immun.*, 9:456-63 (2017).
Tang et al., "Loss of mTOR-Dependent Macroautophagy Causes Autistic-like Synaptic Pruning Deficits," *Neuron*, 83(5):1131-1143 (2014).
Videnovic A, Golombek D., "Circadian Dysregulation in Parkinson's Disease," *Neurobiol. Sleep Circadian Rhythms*, 2:53-8 (2017).
West et al., "Squalamine increases vagal afferent firing frequency in aging mice," J. of the Canadian Association of Gatroenterology, 1 (2018).
Korff, et al., "α-Synuclein in Cerebrospinal Fluid of Alzheimer's Disease and Mild Cognitive Impairment" *J. Alzheimers Dis.* Jan. 1, 2013; 36(4): 679-688.
Non-Final Office Action issued in co-pending U.S. Appl. No. 16/530,113, dated Mar. 25, 2021.
Office Action issued in co-pending U.S. Appl. No. 16/530,127, dated Jun. 25, 2021.
Office Action issued in co-pending U.S. Appl. No. 16/530,295, dated Jul. 9, 2021.
Office Action issued in co-pending U.S. Appl. No. 16/530,247, dated Jul. 9, 2021.
Office Action issued in co-pending U.S. Appl. No. 16/530,051, dated Jul. 16, 2021.
Stanford Health Care ("Complications of Constipation," https://standordhealthcare.org/medical-conditions/primary-care/constipation/complications.html. Accessed Jun. 18, 2021.
Pathak, ("Rectal Prolapse," Web MD, https://www.webmd.com/digestive-disorders/what-is-rectal-prolapse.), Aug. 26, 2020.
International Preliminary Report on Patentability issued in International Patent Application No. PCT/US2019/044917, dated Feb. 18, 2021.
International Preliminary Report on Patentability issued in International Patent Application No. PCT/US2019/044882, dated Feb. 18, 2021.
Non-Final Office Action issued in co-pending U.S. Appl. No. 16/530,247, dated Mar. 4, 2021.
Office Action issued in co-pending U.S. Appl. No. 16/530,200, dated Aug. 24, 2021.
Carmona, et al., "A Squalamine Derivative, NV669, as a Novel PTP1B Inhibitor: in vitro and in vivo effects on pancreatic and hepatic tumor growth," *Oncotarget*, vol. 10, pp. 6651-6667 (2019).
Pang et al., "Constipation in Children with Autism and Autistic Spectrum Disorder," *Pediatr. Surg. Int.*, vol. 27, pp. 353-358 (2011).
Posey et al., "Pharmacotherapeutic Management of Autism," *Expert Opinion on Pharmacotherapy*, vol. 2, No. 4, pp. 587-600 (2001).
Blanchet et al., "Claramines: A New Class of Broad-Spectrum Antimicrobial Agents with Biomodal Activity," *ChemMedChem*, Wiley-VCH Verlag, vol. 13, No. 10, pp. 1018-1027 (2018).
Office Action issued in co-pending U.S. Appl. No. 16/530,113, dated Nov. 3, 2021.
Office Action issued in co-pending U.S. Appl. No. 16/530,113, dated Apr. 13, 2022.
Office Action issued in co-pending U.S. Appl. No. 16/530,200, dated Mar. 22, 2022.
Office Action issued in co-pending U.S. Appl. No. 16/530,127, dated Mar. 22, 2022.
Pernie, et al., "Multistep Inhibition of α-Synuclein Aggregation and Toxicity in Vitro and in Vivo by Trodusquermine," ACS Chemical Biology, vol. 13, No. 8, pp. 2308-2319 (Jun. 2018).
Communication issued in European Patent Application No. 19843250.2, dated Mar. 18, 2022.
Office Action issued in co-pending U.S. Appl. No. 16/530,295, dated Jun. 21, 2022.
Office Action issued in co-pending U.S. Appl. No. 16/530,247, dated Jun. 15, 2022.
Office Action issued in co-pending U.S. Appl. No. 16/530,051, dated Jun. 16, 2022.
Office Action issued in co-pending U.S. Appl. No. 16/530,113, dated Aug. 2, 2022.
Lepine et al. ("The Epidemiology of pain in depression," Human Psychopharmacology (2004); 19: S3-S7, published online in Wiley InterScience (www.interscience.wiley.com), DOI: 10.1002/hup.6.18).
Blackburn, "Depressive Disorders: Treatment Failures and Poor Prognosis over the last 50 years," Pharmacology Research & Perspectives, vol. 7, pp. 1-20 (2019).
Gower, et al., "Emergency Department Management of Delirium in the Elderly," Western Journ. of Emergency Medicine, vol. XIII, No. 2, pp. 194-201 (May 2012).
Alzheimer Scotland (Information Sheet: Constipation & Faecal Impaction, Alzheimer Scotland: Action on Demand (Aug. 2011), 8 pages.
National Institute of Aging ("Alzheimer's Caregiving: Alzheimer's and Hallucinations, Delusions, and Paranoia," (Aug. 2017), 5 pages.
National Institute on Aging, "How is Alzheimer's Disease Treated?," (May 2022), 13 pages.
Extended Search Report issued in co-pending European Patent Application No. 19845506.5, dated Aug. 19, 2022.
Shpakov, "Functional Activity of the Insulin Signaling System of the brain in Health and Type 2 Diabetes Mellitus," *Neuroscience and Behavioral Physiology*, vol. 47, No. 2, (Feb. 2017).

(56) References Cited

OTHER PUBLICATIONS

Vieira, et al., "Protein Tyrosine Phosphatase 1B (PTP1B): A Potential Target for Alzheimer's Therapy?," *Frontiers in Aging Neuroscience*, vol. 9, No. 7, 9 pages (Jan. 2017).

* cited by examiner

AMINOSTEROL COMPOSITIONS AND METHODS OF USING THE SAME FOR TREATING SCHIZOPHRENIA

CROSS-REFERENCE TO RELATED APPLICATIONS

This application claims the priority benefits under 35 USC § 119 to U.S. provisional Application No. 62/714,470, filed Aug. 3, 2018; U.S. provisional Application No. 62/714,468, filed Aug. 3, 2018; and U.S. provisional Application No. 62/789,438, filed Jan. 7, 2019, the entire contents of which are incorporated herein by reference in their entirety.

FIELD

The present application relates generally to compositions and methods for treating, preventing, and/or slowing the onset or progression of schizophrenia and/or a variety of symptoms and disorders related thereto with aminosterols or pharmaceutically acceptable salts or derivatives thereof.

BACKGROUND

Amino sterols are amino derivatives of a sterol. Examples of aminosterols include squalamine and Aminosterol 1436 (also known as trodusquemine and MSI-1436).

Squalamine is a unique compound with a structure of a bile acid coupled to a polyamine (spermidine):

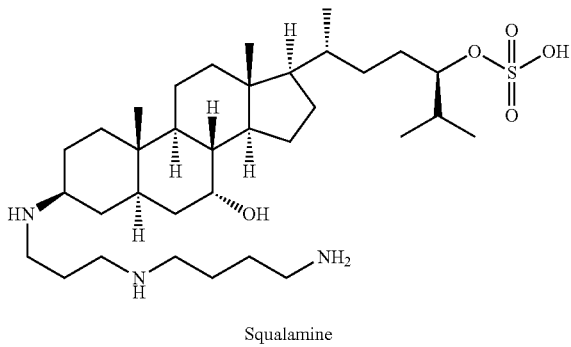

Squalamine

The discovery of squalamine, the structure of which is shown above, was reported by Michael Zasloff in 1993 (U.S. Pat. No. 5,192,756). Squalamine was discovered in various tissues of the dogfish shark (*Squalus acanthias*) in a search for antibacterial agents. The most abundant source of squalamine is in the livers of *Squalus acanthias*, although it is found in other sources, such as lampreys (Yun et al., 2007).

Several clinical trials have been conducted relating to the use of squalamine, including the following:

(1) ClinicalTrials.gov Identifier NCT01769183 for "Squalamine for the Treatment in Proliferative Diabetic Retinopathy," by Elman Retina Group (6 participants; study completed August 2014);

(2) ClinicalTrials.gov Identifier NCT02727881 for "Efficacy and Safety Study of Squalamine Ophthalmic Solution in Subjects With Neovascular AMD (MAKO)," by Ohr Pharmaceutical Inc. (230 participants; study completed December 2017);

(3) ClinicalTrials.gov Identifier NCT02614937 for "Study of Squalamine Lactate for the Treatment of Macular Edema Related to Retinal Vein Occlusion," by Ohr Pharmaceutical Inc. (20 participants; study completed December 2014);

(4) ClinicalTrials.gov Identifier NCT01678963 for "Efficacy and Safety of Squalamine Lactate Eye Drops in Subjects With Neovascular (Wet) Age-related Macular Degeneration (AMD)," by Ohr Pharmaceutical Inc. (142 participants; study completed March 2015);

(5) ClinicalTrials.gov Identifier NCT00333476 for "A Study of MSI-1256F (Squalamine Lactate) To Treat "Wet" Age-Related Macular Degeneration," by Genaera Corporation (140 participants; study terminated);

(6) ClinicalTrials.gov Identifier NCT00094120 for "MSI-1256F (Squalamine Lactate) in Combination With Verteporfin in Patients With "Wet" Age-Related Macular Degeneration (AMD)," by Genaera Corporation (60 participants; study completed February 2007);

(7) ClinicalTrials.gov Identifier NCT00089830 for "A Safety and Efficacy Study of MSI-1256F (Squalamine Lactate) To Treat "Wet" Age-Related Macular Degeneration," by Genaera Corporation (120 participants; study completed May 2007); and (8) ClinicalTrials.gov Identifier NCT03047629 for Evaluation of Safety and Tolerability of ENT-01 for the Treatment of Parkinson's Disease Related Constipation (RASMET) (50 participants; study completed Jun. 14, 2018).

Aminosterol 1436 is an aminosterol isolated from the dogfish shark, which is structurally related to squalamine (U.S. Pat. No. 5,840,936). It is also known as MSI-1436, trodusquemine and produlestan.

Several clinical trials have been conducted relating to the use of Aminosterol 1436:

(1) ClinicalTrials.gov Identifier NCT00509132 for "A Phase I, Double-Blind, Randomized, Placebo-Controlled Ascending IV Single-Dose Tolerance and Pharmacokinetic Study of Trodusquemine in Healthy Volunteers," by Genaera Corp.;

(2) ClinicalTrials.gov Identifier NCT00606112 for "A Single Dose, Tolerance and Pharmacokinetic Study in Obese or Overweight Type 2 Diabetic Volunteer," by Genaera Corp.;

(3) ClinicalTrials.gov Identifier NCT00806338 for "An Ascending Multi-Dose, Tolerance and Pharmacokinetic Study in Obese or Overweight Type 2 Diabetic Volunteers," by Genaera Corp.; and (4) ClinicalTrials.gov Identifier: NCT02524951 for "Safety and Tolerability of MSI-1436C in Metastatic Breast Cancer," by DepyMed Inc.

The full potential of aminosterols for use in treatment of has yet to be determined.

SUMMARY

The present application relates generally to methods for treating, preventing, and/or slowing the onset or progression of schizophrenia (SZ) and/or a related symptom. The methods comprise administering at least one aminosterol or a pharmaceutically acceptable salt or derivative thereof to a subject in need. Certain embodiments describe the determination and administration of a "fixed dose" of an aminosterol or a pharmaceutically acceptable salt or derivative thereof that is not age, size, or weight dependent but rather is individually calibrated.

The aminosterol or a salt or derivative thereof can be formulated with one or more pharmaceutically acceptable carriers or excipients. Preferably the aminosterol is a pharmaceutically acceptable grade of the aminosterol.

In one embodiment, the invention encompasses a method of treating, preventing and/or slowing the onset or progression of schizophrenia and/or a related symptom in a subject in need comprising administering to the subject a therapeutically effective amount of at least one aminosterol or a salt or derivative thereof. In one aspect, the at least one aminosterol or a salt or derivative thereof is administered via oral, nasal, sublingual, buccal, rectal, vaginal, intravenous, intra-arterial, intradermal, intraperitoneal, intrathecal, intramuscular, epidural, intracerebral, intracerebroventricular, transdermal, or any combination thereof. In another aspect, the at least one aminosterol or a salt or derivative thereof is administered nasally. In another aspect, administration of the at least one aminosterol or a salt or derivative thereof comprises non-oral administration.

The therapeutically effect amount of the at least one aminosterol or a salt or derivative thereof in the methods of the invention can be, for example, about 0.1 to about 20 mg/kg, about 0.1 to about 15 mg/kg, about 0.1 to about 10 mg/kg, about 0.1 to about 5 mg/kg, or about 0.1 to about 2.5 mg/kg body weight of the subject. In another aspect, the therapeutically effect amount of the at least one aminosterol or a salt or derivative thereof in the methods of the invention can be, for example, about 0.001 to about 500 mg/day, about 0.001 to about 250 mg/day, about 0.001 to about 125 mg/day, about 0.001 to about 50 mg/day, about 0.001 to about 25 mg/day, or about 0.001 to about 10 mg/day. In other embodiments comprising intranasal administration, therapeutically effect amount of the at least one aminosterol or a salt or derivative thereof comprises about 0.001 to about 6 mg/day; and/or comprises about 0.001 to about 4 mg/day; and/or comprises about 0.001 to about 2 mg/day; and/or comprises about 0.001 to about 1 mg/day.

In another embodiment, the invention encompasses a method of treating, preventing and/or slowing the onset or progression of schizophrenia and/or a related symptom in a subject in need comprising (a) determining a dose of an aminosterol or a salt or derivative thereof for the subject, wherein the aminosterol dose is determined based on the effectiveness of the aminosterol dose in improving or resolving a SZ symptom being evaluated, (b) followed by administering the aminosterol dose to the subject for a period of time, wherein the method comprises (i) identifying a SZ symptom to be evaluated; (ii) identifying a starting aminosterol dose for the subject; and (iii) administering an escalating dose of the aminosterol to the subject over a period of time until an effective dose for the SZ symptom being evaluated is identified, wherein the effective dose is the aminosterol dose where improvement or resolution of the SZ symptom is observed, and fixing the aminosterol dose at that level for that particular SZ symptom in that particular subject.

In the methods of the invention, the aminosterol or a salt or derivative thereof can be administered via any pharmaceutically acceptable means. For example, the aminosterol or a salt or derivative thereof can be administered orally, intranasally, by injection (IV, IP, or IM) or any combination thereof. Oral and intranasal administration or a combination thereof, are preferred.

In one embodiment, starting dosages of the aminosterol or a salt or derivative thereof for oral administration can range, for example, from about 1 mg up to about 175 mg/day, or any amount in-between these two values. In another embodiment, the composition is administered orally and the dosage of the aminosterol or a salt or derivative thereof is escalated in about 25 mg increments. In yet another embodiment, the composition is administered orally and the dose of the aminosterol or a salt or derivative thereof for the subject following dose escalation is fixed at a range of from about 1 mg up to about 500 mg/day, or any amount in-between these two values.

In another embodiment, the composition is administered intranasally (IN) and the starting aminosterol or a salt or derivative thereof dosage ranges from about 0.001 mg to about 3 mg/day, or any amount in-between these two values. For example, the starting aminosterol dosage for IN administration, prior to dose escalation, can be, for example, about 0.001, about 0.005, about 0.01, about 0.02, about 0.03, about 0.05, about 0.06, about 0.07, about 0.08, about 0.09, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 1.0, about 1.1, about 1.25, about 1.3, about 1.4, about 1.5, about 1.6, about 1.7, about 1.75, about 1.8, about 1.9, about 2.0, about 2.1, about 2.25, about 2.3, about 2.4, about 2.5, about 2.6, about 2.7, about 2.75, about 2.8, about 2.9, or about 3 mg/day.

In another embodiment, the composition is administered intranasally and the dosage of the aminosterol or a salt or derivative thereof is escalated in increments of about 0.01, about 0.05, about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

Finally, in yet another embodiment, the composition is administered intranasally and the dose of the aminosterol or a salt or derivative thereof for the subject following escalation is fixed at a range of from about 0.001 mg up to about 6 mg/day, or any amount in-between these two values. In yet a further embodiment, the aminosterol composition is administered intranasally and the dose of the aminosterol or a salt or derivative thereof for the subject following dose escalation is a dose which is sub therapeutic when given orally or by injection.

In one embodiment, the dosage of the aminosterol or a salt or derivative thereof is escalated every about 3 to about 5 days. In another embodiment, the dose of the aminosterol or a salt or derivative thereof is escalated about 1×/week, about 2×/week, about every other week, or about 1×/month. In yet another embodiment, the dose of the aminosterol or a salt or derivative thereof is escalated every about 1, about 2, about 3, about 4, about 5, about 6, about 7, about 8, about 9, about 10, about 11, about 12, about 13, or about 14 days.

In another embodiment, the fixed dose of the aminosterol or a salt or derivative thereof is given once per day, every other day, once per week, twice per week, three times per week, four times per week, five times per week, six times per week, every other week, or every few days. In addition, the fixed dose of the aminosterol or a salt or derivative thereof can be administered for a first defined period of time of administration, followed by a cessation of administration for a second defined period of time, followed by resuming administration upon recurrence of SZ or a symptom of SZ. For example, the fixed aminosterol dose can be incrementally reduced after the fixed dose of aminosterol or a salt or derivative thereof has been administered to the subject for a period of time. Alternatively, the fixed aminosterol dose is varied plus or minus a defined amount to enable a modest reduction or increase in the fixed dose. For example, the fixed aminosterol dose can be increased or decreased by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In another embodiment, the starting aminosterol or a salt or derivative thereof dose is higher if the SZ symptom being evaluated is severe.

In one embodiment, the method results in slowing, halting, or reversing progression or onset of SZ over a defined period of time following administration of the fixed escalated dose of the aminosterol or a salt or derivative thereof, as measured by a medically-recognized technique. For example, the progression or onset of schizophrenia may be slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique. In addition, the method of the invention can result in positively impacting the SZ, as measured by a medically-recognized technique.

The positive impact and/or progression of SZ, and/or improvement or resolution of the SZ symptom being evaluated, may be measured quantitatively or qualitatively by one or more clinically recognized scales, tools, or techniques selected from the group consisting of The Clinical Assessment Interview for Negative Symptoms (CAINS), The Brief Negative Symptom Scale (BNSS), Scale for the Assessment of Positive Symptoms (SAPS), the Scale for the Assessment of Negative Symptoms (SANS), the Positive and Negative Symptoms Scale (PANSS), the Negative Symptom Assessment (NSA-16), the Clinical Global Impression Schizophrenia (CGI-SCH), computed tomography (CT), magnetic resonance imaging (MRI), magnetic resonance spectroscopy, functional MRI (fMRI), diffusion tensor imaging, single photon emission computed tomography (SPECT), and positron emission tomography (PET).

In one embodiment, the fixed escalated aminosterol dose reverses dysfunction caused by the SZ and treats, prevents, improves, and/or resolves the schizophrenia symptom being evaluated.

In another embodiment, the fixed escalated aminosterol dose reverses dysfunction caused by the SZ and treats, prevents, improves, and/or resolves the schizophrenia symptom being evaluated. The improvement or resolution of the SZ symptom can be measured using a clinically recognized scale or tool. For example, the improvement in the schizophrenia symptom can be at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using a clinically recognized scale.

In yet another embodiment, the SZ symptom to be evaluated can be selected from the group consisting of (a) reduced social engagement, social withdrawal, and/or social isolation; (b) reduced emotional expression; (c) disorganized or irrational behavior; (d) disorganized or irrational thinking; (e) disorganized or irrational speech; (f) aggression or anger; (g) anxiety; (h) compulsive behavior; (i) excitability; (j) repetitive movements; (k) self-harm; (l) delusions; (m) amnesia; (n) emotional instability, including difficulty controlling emotions; (o) hallucinations; (p) depression; (q) constipation; (r) neurodegeneration associated with schizophrenia; (s) sleep problem, sleep disorder, and/or sleep disturbance; (t) cognitive impairment; (u) feelings of fright and/or paranoia; (v) false beliefs; (w) distorted thoughts; (x) lack of emotion or a very limited range of emotions; (y) catatonia; (z) impaired motor behavior and coordination; (aa) inability to make decisions; (bb) forgetting or losing things; (cc) poor executive functioning; (dd) ADHD, trouble focusing, paying attention and/or difficulty concentrating; (ee) difficulty with working memory; (ff) lack of motivation; (gg) reduced energy or apathy; (hh) reduced speech; (ii) loss of pleasure or interest in life; (jj) poor hygiene and grooming habits; (kk) hypertension; (ll) hypotension; (mm) sexual dysfunction, such as impotence and/or loss of libido, and/or (nn) cardiovascular disease.

In one embodiment, the schizophrenia symptom to be evaluated is a sleep problem, sleep disorder, or sleep disturbance associated with schizophrenia, and the sleep problem, sleep disorder, or sleep disturbance comprises a delay in sleep onset, sleep fragmentation, REM-behavior disorder, sleep-disordered breathing including snoring and apnea, day-time sleepiness, micro-sleep episodes, narcolepsy, hallucinations, or any combination thereof. Further, the REM-behavior disorder can comprise vivid dreams, nightmares, and acting out the dreams by speaking or screaming, or fidgeting or thrashing of arms or legs during sleep. Treating the sleep problem, sleep disorder, or sleep disturbance prevents or delays the onset and/or progression of the schizophrenia.

In one embodiment, the schizophrenia symptom to be evaluated is a sleep problem, sleep disorder, sleep disturbance, circadian rhythm dysfunction, REM disturbed sleep, or REM behavior disorder, and (a) the method results in a positive change in the sleeping pattern of the subject; (b) the method results in a positive change in the sleeping pattern of the subject, wherein the positive change is defined as: (i) an increase in the total amount of sleep obtained of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or (ii) a percent decrease in the number of awakenings during the night selected from the group consisting of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%; and/or (c) as a result of the method the subject obtains the total number of hours of sleep recommended by a medical authority for the age group of the subject.

In another embodiment, the SZ symptom to be evaluated is hallucinations and wherein: (a) the hallucinations comprise a visual, auditory, tactile, gustatory or olfactory hallucinations (b) the method results in a decreased number of hallucinations over a defined period of time in the subject; (c) the method results in a decreased number of hallucinations over a defined period of time in the subject selected from the group consisting of by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or (d) the method results in the subject being hallucination-free. In one embodiment, the fixed escalated aminosterol dose reverses dysfunction caused by the schizophrenia and treats and/or prevents the hallucination.

In another embodiment, the SZ symptom to be evaluated is hallucinations and wherein: (a) the hallucinations comprise a visual, auditory, tactile, gustatory or olfactory hallucinations; (b) the method results in a decreased severity of hallucinations in the subject over a defined period of time, wherein the decrease in severity is measured by one or more medically-recognized techniques; (c) the method results in a decreased severity of hallucinations in the subject over a defined period of time, wherein the decrease in severity is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as measured by one or more medically recognized techniques; and/or (d) the method results in the subject being hallucination-free. The one or more medically recognized techniques may be selected from the group consisting of Chicago Hallucination Assessment Tool (CHAT), The Psychotic Symptom Rating Scales (PSYRATS), Auditory Hallucinations Rating Scale (AHRS), Hamilton Program for Schizophrenia Voices Questionnaire (HPSVQ), Characteristics of Auditory Hallucinations Questionnaire (CAHQ), Mental Health Research Institute Unusual Perception Schedule (MUPS), positive and negative syndrome scale (PANSS), scale for the assessment of positive symptoms (SAPS), Launay-Slade hallucinations scale (LSHS), the Cardiff anomalous perceptions scale (CAPS), and structured interview for assessing perceptual anomalies (SIAPA).

In another embodiment, the schizophrenia symptom to be evaluated is depression. In an exemplary embodiment, the method results in improvement in a subject's depression, as measured by one or more clinically-recognized depression rating scales. For example, the improvement can be in one or more depression characteristics selected from the group consisting of mood, behavior, bodily functions such as eating, sleeping, energy, and sexual activity, and/or episodes of sadness or apathy. In another embodiment, the improvement a subject experiences following treatment can be about 5, about 10, about 15, about 20, about 25, about 30, about 35, about 40, about 45, about 50, about 55, about 60, about 65, about 70, about 75, about 80, about 85, about 90, about 95 or about 100%.

In some embodiments, the schizophrenia symptom to be evaluated is cognitive impairment, and (a) progression or onset of the cognitive impairment is slowed, halted, or reversed over a defined period of time following administration of the fixed escalated dose of the aminosterol or a salt or derivative thereof, as measured by a medically-recognized technique; (b) the cognitive impairment is positively impacted by the fixed escalated dose of the aminosterol or a salt or derivative thereof, as measured by a medically-recognized technique; (c) the cognitive impairment is positively impacted by the fixed escalated dose of the aminosterol or a salt or derivative thereof, as measured by a medically-recognized technique and the positive impact on and/or progression of cognitive impairment is measured quantitatively or qualitatively by one or more techniques selected from the group consisting of ADASCog, Mini-Mental State Exam(MMSE), Mini-cog test, Woodcock-Johnson Tests of Cognitive Abilities, Leiter International Performance Scale, Miller Analogies Test, Raven's Progressive Matrices, Wonderlic Personnel Test, IQ tests, or a computerized tested selected from Cantab Mobile, Cognigram, Cognivue, Cognision, and Automated Neuropsychological Assessment Metrics Cognitive Performance Test (CPT); and/or (d) the progression or onset of cognitive impairment is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique.

In some embodiments, the schizophrenia symptom to be evaluated is constipation, and (a) treating the constipation prevents and/or delays the onset and/or progression of the schizophrenia; (b) the fixed escalated aminosterol dose causes the subject to have a bowel movement; (c) the method results in an increase in the frequency of bowel movement in the subject; (d) the method results in an increase in the frequency of bowel movement in the subject and the increase in the frequency of bowel movement is defined as: (i) an increase in the number of bowel movements per week of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or (ii) a percent decrease in the amount of time between each successive bowel movement selected from the group consisting of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%; (e) as a result of the method the subject has the frequency of bowel movement recommended by a medical authority for the age group of the subject; and/or (f) the starting aminosterol dose is determined by the severity of the constipation, wherein: (i) if the average complete spontaneous bowel movement (CSBM) or spontaneous bowel movement (SBM) is one or less per week, then the starting aminosterol dose is at least about 150 mg; and (ii) if the average CSBM or SBM is greater than one per week, then the starting aminosterol dose is about 75 mg or less.

In one embodiment, the schizophrenia symptom to be evaluated is neurodegeneration, and (a) treating the neurodegeneration prevents and/or delays the onset and/or progression of the schizophrenia; and/or (b) the method results in treating, preventing, and/or delaying the progression and/or onset of neurodegeneration in the subject. In an exemplary embodiment (a) progression or onset of the neurodegeneration is slowed, halted, or reversed over a defined period of time following administration of the fixed escalated dose of the aminosterol or a salt or derivative thereof, as measured by a medically-recognized technique; and/or (b) the neurodegeneration is positively impacted by the fixed escalated dose of the aminosterol or a salt or derivative thereof, as measured by a medically-recognized technique. The positive impact and/or progression of neurodegeneration can be measured quantitatively or qualitatively by one or more techniques selected from the group consisting of electroencephalogram (EEG), neuroimaging, functional MRI, structural MRI, diffusion tensor imaging (DTI), [18F]fluorodeoxyglucose (FDG) PET, agents that label amyloid, [18F]F-dopa PET, radiotracer imaging, volumetric analysis of regional tissue loss, specific imaging markers of abnormal protein deposition, multimodal imaging, and biomarker analysis. In addition, the progression or onset of neurodegeneration can be slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique.

For all of the embodiments described herein, each defined period of time is independently selected from the group consisting of about 1 day to about 10 days, about 10 days to about 30 days, about 30 days to about 3 months, about 3 months to about 6 months, about 6 months to about 12 months, and about greater than 12 months.

In another embodiment, the aminosterol or a salt or derivative thereof is administered in combination with at least one additional active agent to achieve either an additive or synergistic effect. For example, the additional active agent can be administered via a method selected from the group consisting of (a) concomitantly; (b) as an admixture; (c) separately and simultaneously or concurrently; or (d) separately and sequentially. In another embodiment, the additional active agent is a different aminosterol from that administered in primary method. In yet a further embodiment, the method of the invention comprises administering a first aminosterol which is aminosterol 1436 or a salt or derivative thereof intranasally and administering a second aminosterol which is squalamine or a salt or derivative thereof orally.

In another embodiment, the at least one additional active agent is an active agent used to treat schizophrenia or a symptom thereof. In some embodiments, the active agent is selected from the group consisting of first-generation antipsychotics such as chlorpromazine (THORAZINEM®), fluphenazine (PROLIXIN®, haloperidol (HALDOL®), perphenazine (TRILAFON®), thioridazine (MELLARIL®), thiothixene (NAVANE®), and trifluoperazine (STELAZINE®); atypical antipsychotics such as aripiprazole (ABILIFY®), aripiprazole lauroxil (ARISTADA®), asenapine (SAPHRIS®), clozapine (CLOZARIL®), iloperidone (FANAPT®), lurasidone (LATUDA®), olanzapine (Zyprexa®), paliperidone (INVEGA SUSTENNA®), paliperidone palmitate (INVEGA TRINZA®), quetiapine (SEROQUEL®), risperidone (RISPERDAL®), and ziprasidone (GEODON®).

For all of the methods of the invention, in one embodiment each aminosterol dose is taken on an empty stomach, optionally within about two hours of the subject waking. In another embodiment for all of the methods of the invention, no food is taken or consumed after about 60 to about 90 minutes of taking the aminosterol dose. Further, in yet another embodiment applicable to all of the methods of the invention, the aminosterol or a salt or derivative thereof can be a pharmaceutically acceptable grade of at least one aminosterol or a pharmaceutically acceptable salt or derivative thereof. For all of the methods of the invention the subject can be a human.

In another embodiment, the subject to be treated according to the methods of the invention can be a member of a patient population at risk for being diagnosed with SZ.

The aminosterol or a salt or derivative thereof utilized in the methods of the invention can be, for example, (a) isolated from the liver of *Squalus acanthias*; (b) a synthetic aminosterol; (c) squalamine or a pharmaceutically acceptable salt thereof; (d) a squalamine isomer; (e) the phosphate salt of squalamine; (f) aminosterol 1436 or a pharmaceutically acceptable salt thereof; (g) an aminosterol 1436 isomer; (h) the phosphate salt of aminosterol 1436; (i) a compound comprising a sterol nucleus and a polyamine attached at any position on the sterol, such that the molecule exhibits a net charge of at least +1; (j) a compound comprising a bile acid nucleus and a polyamine, attached at any position on the bile acid, such that the molecule exhibits a net charge of at least +1; (k) a derivative modified to include one or more of the following: (i) substitutions of the sulfate by a sulfonate, phosphate, carboxylate, or other anionic moiety chosen to circumvent metabolic removal of the sulfate moiety and oxidation of the cholesterol side chain; (ii) replacement of a hydroxyl group by a non-metabolizable polar substituent, such as a fluorine atom, to prevent its metabolic oxidation or conjugation; and (iii) substitution of one or more ring hydrogen atoms to prevent oxidative or reductive metabolism of the steroid ring system; and/or (l) a derivative of squalamine or aminosterol 1436 modified through medicinal chemistry to improve bio-distribution, ease of administration, metabolic stability, or any combination thereof. In one embodiment, the aminosterol is selected from the group consisting aminosterol 1436 or a pharmaceutically acceptable salt thereof, squalamine or a pharmaceutically acceptable salt thereof, or a combination thereof. In another embodiment, the aminosterol is a phosphate salt.

In another embodiment, the aminosterol in the methods of the invention is selected from the group consisting of:

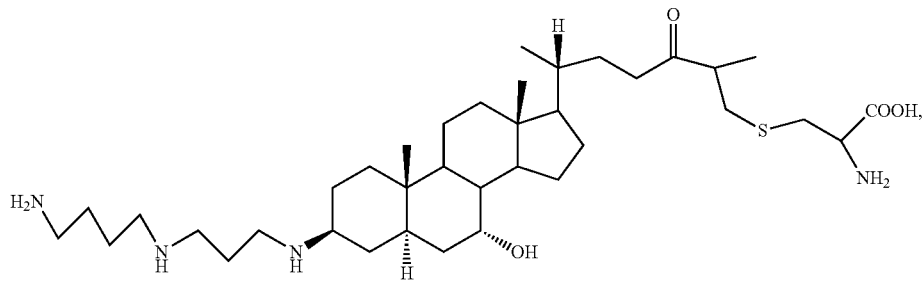

Compound 1

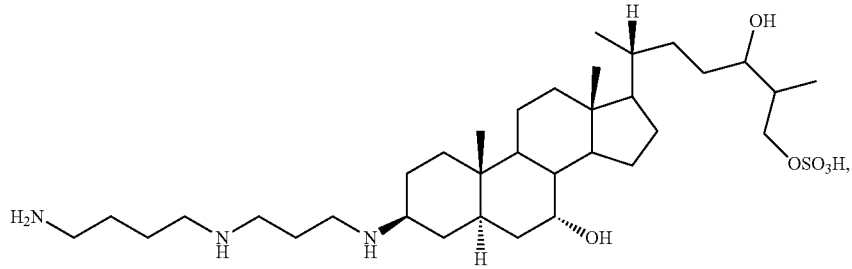

Compound 2

-continued
Compound 3
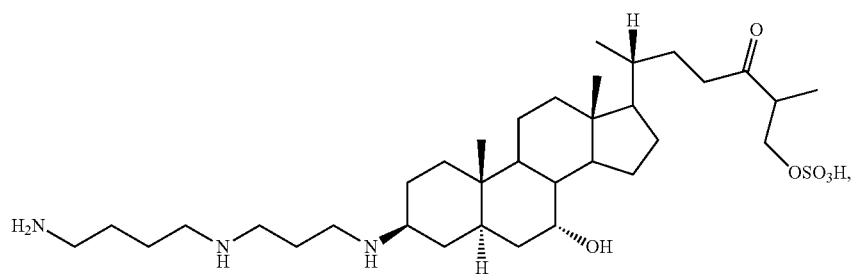
Compound 4
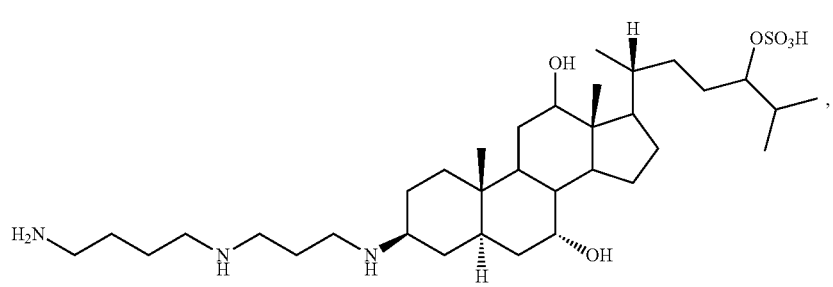
Compound 5
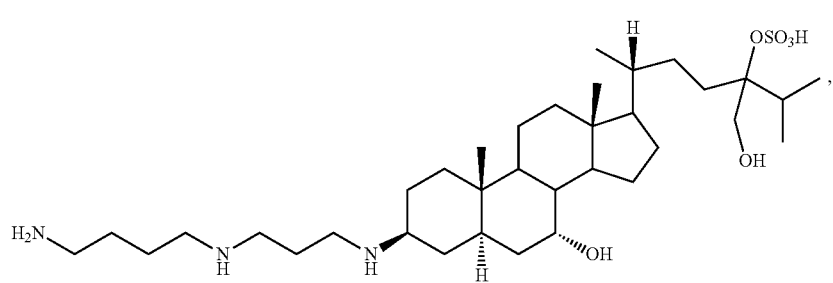
Compound 6
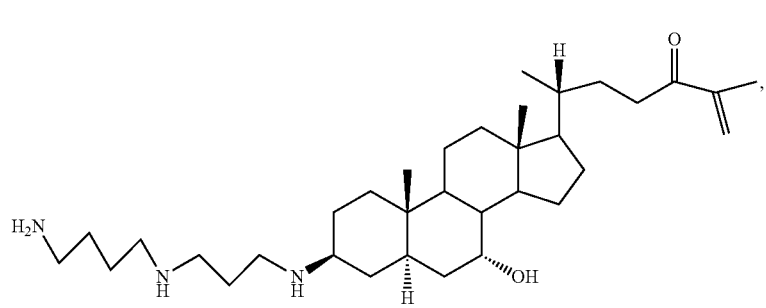
Compound 7
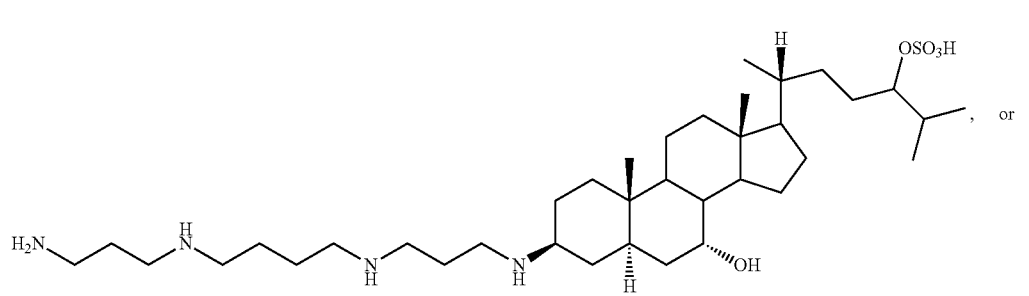
or -continued

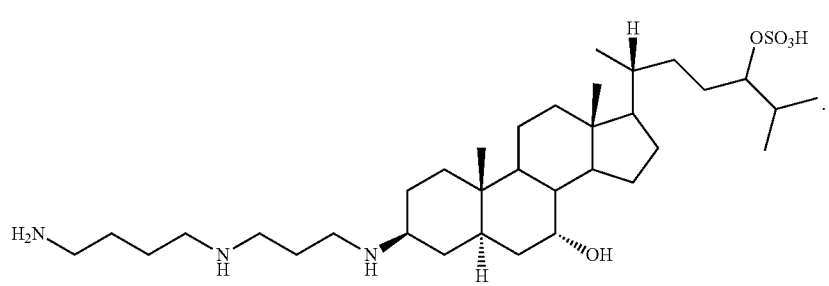

Compound 8

Further, the aminosterol composition can comprise, for example, one or more of the following: an aqueous carrier, a buffer, a sugar, and/or a polyol compound.

Both the foregoing summary and the following description of the drawings and detailed description are exemplary and explanatory. They are intended to provide further details of the invention, but are not to be construed as limiting. Other objects, advantages, and novel features will be readily apparent to those skilled in the art from the following detailed description of the invention.

BRIEF DESCRIPTION OF THE DRAWINGS

As shown in FIG. 1A, in Stage 1 of the clinical study (single dose), cumulative prokinetic response rate was defined as the proportion of patients who had a complete spontaneous bowel movements (CSBM) within 24 hours of dosing. In Stage 2 (daily dosing), a prokinetic response was defined as the fraction of patients who had a CSBM within 24 hours of dosing on at least 2 out of 3 days at any given dose. As shown in FIG. 1B, the prokinetic dose of squalamine was significantly related to baseline constipation severity (p=0.00055). Patients with baseline CSBM <1 required a higher dose (mean, 192 mg) of squalamine than patients with CSBM ≥1 (mean, 120 mg).

DETAILED DESCRIPTION

I. Overview

Figure 1B:
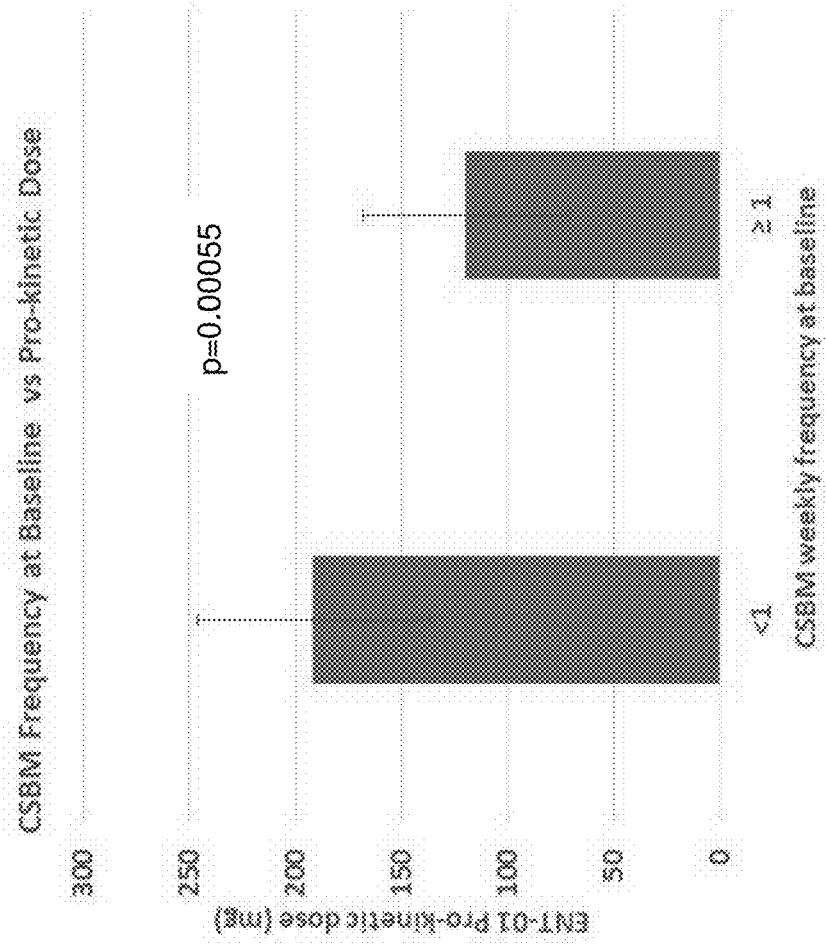
FIGS. 1A and 1B show prokinetic activity of squalamine (ENT-01, a synthetic squalamine salt comprising squalamine as the active ion).

The present application relates generally to compositions and methods for treating, preventing and/or slowing or delaying the onset or progression of schizophrenia and/or a related symptom. The methods comprise administering one or more aminosterols or pharmaceutically acceptable salts or derivatives thereof to a subject in need.

The present application relates generally to methods for treating, preventing, and/or slowing the onset or progression of schizophrenia (SZ) and/or a related symptom. The methods comprise administering at least one aminosterol or a pharmaceutically acceptable salt or derivative thereof to a subject in need. Certain embodiments describe the determination and administration of a "fixed dose" of an aminosterol or a pharmaceutically acceptable salt or derivative thereof that is not age, size, or weight dependent but rather is individually calibrated.

The aminosterol or a salt or derivative thereof can be formulated with one or more pharmaceutically acceptable carriers or excipients. Preferably the aminosterol is a pharmaceutically acceptable grade of the aminosterol.

In one embodiment, the invention encompasses a method of treating, preventing and/or slowing the onset or progression of schizophrenia and/or a related symptom in a subject in need comprising administering to the subject a therapeutically effective amount of at least one aminosterol or a salt or derivative thereof. In one aspect, the at least one aminosterol or a salt or derivative thereof is administered via oral, nasal, sublingual, buccal, rectal, vaginal, intravenous, intra-arterial, intradermal, intraperitoneal, intrathecal, intramuscular, epidural, intracerebral, intracerebroventricular, transdermal, or any combination thereof. In another aspect, the at least one aminosterol or a salt or derivative thereof is administered nasally. In another aspect, administration of the at least one aminosterol or a salt or derivative thereof comprises non-oral administration.

In one embodiment, the present invention is directed to methods of treating, preventing and/or slowing or delaying the onset or progression of schizophrenia and/or a related symptom in a subject in need, comprising (a) determining a dose of an aminosterol or a salt or derivative thereof for the subject, wherein the aminosterol dose is determined based on the effectiveness of the aminosterol dose in improving or resolving a SZ symptom being evaluated; (b) followed by administering the dose of the aminosterol or a salt or derivative thereof to the subject for a period of time. The method of determining the aminosterol dose comprises (i) identifying a SZ symptom to be evaluated; (ii) identifying a starting aminosterol dose for the subject; and (iii) administering an escalating dose of the aminosterol to the subject over a period of time until an effective dose for the SZ symptom being evaluated is identified, wherein the effective dose is the aminosterol dose where improvement or resolution of the SZ symptom is observed, and fixing the aminosterol dose at that level for that particular SZ symptom in that particular subject.

A. Background Regarding Schizophrenia

Schizophrenia is a chronic and severe brain disorder that affects how a person thinks, feels, and behaves. Common symptoms include false beliefs, distorted thoughts, hallucinations, feelings of fright and paranoia, unclear or confused thinking, hearing voices that others do not, reduced social engagement and emotional expression, and a lack of motivation. Although SZ is not as common as other mental disorders, it is the most chronic and disabling of the major mental illnesses. SZ is a life-long disease. SZ occurs in about 1% of the population, and about 2.2 million Americans, ages 18 and older, will develop SZ.

Early-onset SZ occurs from ages 20-30, late-onset occurs after the age of 40, and very-late-onset after the age of 60. It is estimated that 15% of the population with SZ are late-onset and 5% very-late onset. Many of the symptoms of late-onset SZ are similar to the early-onset. However, individuals with late-onsets are more likely to report hallucinations in all sensory modalities, as well as persecutory and partition delusions. On the other hand, late-onset cases are less likely to present with formal thought disorder, affective symptoms. Negative symptoms and cognitive impairment are also rarer in very-late onset cases.

Across studies that use household-based survey samples, clinical diagnostic interviews, and medical records, estimates of the prevalence of SZ and related psychotic disorders in the U.S. range between 0.25% and 0.64%. Despite its relatively low prevalence, SZ is associated with significant health, social, and economic concerns. SZ is one of the top 15 leading causes of disability worldwide. Individuals with SZ have an increased risk of premature mortality. Financial costs associated with SZ are disproportionately high relative to other chronic mental and physical health conditions, reflecting both "direct" costs of health care as well as "indirect" costs of lost productivity, criminal justice involvement, social service needs, and other factors beyond health care.

Contrary to popular belief, SZ is not a split or multiple personality. SZ is a psychosis, a type of mental illness in which a person cannot tell what is real from what is imagined. At times, people with psychotic disorders lose touch with reality. The world may seem like a jumble of confusing thoughts, images, and sounds. The behavior of people with SZ may be very strange and even shocking. A sudden change in personality and behavior, which occurs when SZ sufferers lose touch with reality, is called a psychotic episode.

SZ varies in severity from person to person. Some people have only one psychotic episode while others have many episodes during a lifetime but lead relatively normal lives between episodes. Still other individuals with this disorder may experience a decline in their functioning over time with little improvement between full blown psychotic episodes. SZ symptoms seem to worsen and improve in cycles known as relapses and remissions.

SZ is a long term mental illness which usually shows its first signs in men in their late teens or early 20s, while in women, it tends to be in their early 20s and 30s. The period when symptoms first start to arise and before the onset of full psychosis is called the prodromal period. It can last days, weeks or even years. Sometime it can be difficult to recognize because there is usually no specific trigger. A prodrome is accompanied by what can be perceived as subtle behavioral changes, especially in teens. This includes a change in grades, social withdrawal, trouble concentrating, temper flares, or difficulty sleeping. The most common symptoms of SZ can be grouped into several categories including positive symptoms, cognitive symptoms, and negative symptoms.

Positive symptoms of SZ refer to symptoms added in to one's experience that are exaggerated and irrational forms of thinking or behavior. These symptoms are not based in reality and are sometimes referred to as psychotic symptoms, such as delusions, hallucinations, and catatonia. Disorganized symptoms of SZ are a type of positive symptom that reflects that person's inability to think clearly and respond appropriately. Examples of disorganized symptoms include: (i) talking in sentences that do not make sense or using nonsense words, making it difficult for the person to communicate or engage in conversation; (ii) shifting quickly from one thought to the next without obvious or logical connections between them; (iii) abnormal motor behavior such as moving slowly; (iv) being unable to make decisions; (v) writing excessively but without meaning; (vi) forgetting or losing things; (vii) repeating movements or gestures, such as pacing or walking in circles; and (viii) having problems making sense of everyday sights, sounds, and feelings. Cognitive symptoms of SZ include, for example, (i) poor executive functioning (the ability to understand information and to use it to make decisions); (ii) trouble focusing or paying attention; (iii) difficulty with working memory (the ability to use information immediately after learning it); and (iv) lack of awareness of the cognitive symptoms. Finally, negative symptoms of SZ, which refer to the absence of certain normal behaviors in people with SZ (e.g., a reduced or lack of ability to function normally), include for example, (i) lack of emotion or a very limited range of emotions; (ii) withdrawal from family, friends, and social activities; (iii) reduced energy; (iv) reduced speech; (v) lack of motivation; (vi) loss of pleasure or interest in life; and (vii) poor hygiene and grooming habits.

To date, there are no medications or supplements that have been shown to decrease SZ risk. Moreover, no treatments stop or reverse its progression, though some may temporarily improve symptoms. Affected people increasingly rely on others for assistance, often placing a burden on the caregiver; the pressures can include social, psychological, physical, and economic elements.

What causes schizophrenia? The exact cause of SZ is not yet known, but it is believed that a combination of genetics, brain chemistry, and environment contribute to development of the disorder. For example, regarding genetics, a subject has a greater risk of being diagnosed with SZ if a family member has been diagnosed with SZ. The risk goes up by 10% if the family member is a parent, brother, or sister, and if both parents have SZ then a subject has a 40% chance of being diagnosed with SZ.

Problems with certain naturally occurring brain chemicals, including neurotransmitters called dopamine and glutamate, may contribute to SZ. Neuroimaging studies show differences in the brain structure and central nervous system of people with SZ. While researchers aren't certain about the significance of these changes, they indicate that schizophrenia is a brain disease.

Relationship Between Schizophrenia and PD:

Recent research has suggested that SZ and Parkinson's disease (PD) share a common mechanism. Sumitomo et al. 2018. Specifically, researchers identified a genetic defect and a biological pathway that may contribute to both SZ and early-onset PD. Yet another recent study reported a decreased expression of α-synuclein (αS) in patients with SZ. (Demirel et al., 2017) αS is a protein prominently expressed in the central nervous system. Aggregated αS proteins form brain lesions that are hallmarks of some neurodegenerative diseases (synucleinopathies). Yet another study showed that αS modulates dopamine transporter activity (Butler et al., 2015), and thus an abnormal or decreased expression of αS in SZ subjects may be correlated with an underlying cause of the disease. This may also be true for PD subjects.

SZ has been linked to dopaminergic function, in addition to a reduced dopamine reuptake transporter (DAT) expression in SZ brains. Hyperdopaminergic function is also reported in SZ thus, drugs effective in treating SZ have anti-dopaminergic properties. The antipsychotics (APs) (used for the treatment of SZ) block dopamine D2 receptor (DRD2) and thus produce AP-related neurotoxic effects that are mainly resulting from extrapyramidal symptoms (EPS) and tardive dyskinesia (TD).

B. Background Regarding the Experimental Data

As described in Example 1, a study was conducted in patients with Parkinson's disease (PD). PD is a progressive neurodegenerative disorder caused by accumulation of the protein αS within the enteric nervous system (ENS), autonomic nerves and brain. αS abnormalities are seen in SZ and have also has been suggested to be involved in pathogenesis of SZ (Demirel et al., 2017).

While the study described herein assessed patients with PD, many symptoms assessed and contemplated to be resolved by aminosterol treatment are not restored by the replacement of dopamine and are thus not unique to PD but also correlated with SZ. Examples of such symptoms include, but are not limited to, constipation, disturbances in sleep architecture, cognitive impairment or dysfunction, hallucinations, and depression. Other relevant symptoms are described herein. All of all of these symptoms result from impaired function of neural pathways not restored by replacement of dopamine in PD subjects.

A strategy that targets neurotoxic aggregates of αS in the gastrointestinal tract represents a novel approach to the treatment of PD and other neurodiseases including SZ. Treatment and conditions described herein may restore the function of enteric nerve cells and prevent retrograde trafficking to the brain. Such actions may potentially slow progression of the SZ disease in addition to restoring gastrointestinal function.

Not to be bound by theory, it is believed that aminosterols target neurotoxic aggregates of αS in the gastrointestinal tract, and restore function of the enteric nerve cells. The now-functional enteric nerve cells prevent retrograde trafficking of proteins, such as αS, to the brain. In addition to restoring gastrointestinal function, this effect is believed to slow and possibly reverse SZ disease progression.

Constipation serves as symptom of many neurodiseases such as SZ. Not to be bound by theory, based on the data described herein, it is believed that aminosterols improve bowel function by acting locally on the gastrointestinal tract (as supported by the oral bioavailability <0.3%). An orally administered aminosterol such as squalamine, the active ion of ENT-01, stimulates gastro-intestinal motility in mice with constipation due to overexpression of human αS (West et al, manuscript in preparation). Perfusion of an aminosterol such as squalamine through the lumen of an isolated segment of bowel from the PD mouse model results in excitation of IPANs (intrinsic primary afferent neuron), the major sensory neurons of the ENS that communicate with the myenteric plexus, increasing the frequency of propulsive peristaltic contractions and augmenting neural signals projecting to the afferent arm of the vagus.

Systemic absorption of the aminosterol following oral administration was negligible both in this study and in prior studies involving mice, rats and dogs. Prior studies demonstrated that intravenous administration of an aminosterol such as squalamine was not associated with increased gastrointestinal motility, despite reaching systemic blood levels one thousand-fold greater than that achieved by orally administered squalamine. These data suggest that the effect is mediated by local action in the GI tract. The topical action would also explain why adverse events were largely confined to the gastrointestinal tract.

Several exploratory endpoints were incorporated into the PD trial described in Example 1 to evaluate the impact of an aminosterol on neurologic symptoms associated with a neurodisease such as PD. Following aminosterol treatment, the Unified Parkinson's Disease Rating Scale (UPDRS) score, a global assessment of motor and non-motor symptoms, showed significant improvement. Improvement was also seen in the motor component. The improvement in the motor component is unlikely to be due to improved gastric motility and increased absorption of dopaminergic medications, since improvement persisted during the 2-week washout period, i.e., in the absence of study drug (Table 12).

Improvements were also seen in cognitive function (MMSE scores), hallucinations, REM-behavior disorder (RBD) and sleep. Six of the patients enrolled had daily hallucinations or delusions and these improved or disappeared during treatment in five. In one patient the hallucinations disappeared at 100 mg, despite not having reached the colonic prokinetic dose (e.g., fixed escalated aminosterol dose) of 175 mg for this particular patient. The patient remained free of hallucinations for 1 month following cessation of dosing. RBD and total sleep time also improved progressively in a dose-dependent manner.

Interestingly, most indices related to bowel function returned to baseline value by the end of the 2-week wash-out period while improvement in the CNS symptoms persisted. The rapid improvement in certain CNS symptoms is consistent with a mechanism whereby nerve impulses initiated from the ENS following aminosterol administration augment afferent neural signaling to the CNS. This may stimulate the clearance of αS aggregates within the afferent neurons themselves as well as the secondary and tertiary neurons projecting rostrally within the CNS, since it is known that neural stimulation is accompanied by increased neuronal autophagic activity (Shehata et al. 2012). It is believed that after cessation of aminosterol administration, the neurons of the CNS gradually re-accumulate an αS burden either locally or via trafficking from αS re-aggregation within the gut.

Disturbance of the circadian rhythm has been described in neurodiseases such as SZ and PD both clinically and in animal models and might plays a role in the abnormal sleep architecture, dementia, mood and autonomic dysfunction associated with neurodiseases such as PD (Wulff et al., 2012; Breen et al., 2014; Videnovic et al., 2017; Antonio-Rubio et al., 2015; Madrid-Navarro et al., 2018). Circadian rhythm was monitored through the use of a temperature sensor that continuously captured wrist skin temperature (Sarabia et al., 2008), an objective measure of the autonomic regulation of vascular perfusion (Videnovic et al., 2017). Circadian cycles of wrist skin temperature have been shown to correlate with sleep wake cycles, reflecting the impact of nocturnal heat dissipation from the skin on the decrease in core temperature and the onset of sleep (Sarabia et al., 2008; Ortiz-Tuleda et al., 2014). Oral administration of ENT-01 had a significant positive impact on the circadian rhythm of skin temperature in the 12 patients with evaluable data. Not to be bound by theory, it is believed that aminosterols could be affecting neuronal circuits involving the master clock (the suprachiasmatic nucleus) and its autonomic projections and opens the possibility of therapeutic correction of circadian dysfunction.

As described in Example 1, aminosterol dosing is patient specific, as the aminosterol dose is likely related to the extent of neuronal damage, with greater neuronal damage correlating with the need for a higher aminosterol dose to obtain a desired therapeutic result. As described in greater detail herein, aminosterol dosing can range from about 0.01 to about 500 mg/day, with dosage determination described in more detail below.

II. Methods of Treatment

In one aspect of the disclosure, a method of treating, preventing, and/or slowing the onset or progression of schizophrenia (SZ) and/or a related symptom in a subject in need is provided; the method comprising administering to the subject a therapeutically effective amount of at least one aminosterol, or a salt or derivative thereof.

In some embodiments, administration comprises non-oral administration. In some embodiments, administering comprises administration selected from oral, nasal, sublingual, buccal, rectal, vaginal, intravenous, intra-arterial, intradermal, intraperitoneal, intrathecal, intramuscular, epidural, intracerebral, intracerebroventricular, transdermal, or any combination thereof. In some embodiments, administering comprises nasal administration.

The therapeutically effect amount of the at least one aminosterol or a salt or derivative thereof in the methods of the invention can be, for example, about 0.1 to about 20 mg/kg, about 0.1 to about 15 mg/kg, about 0.1 to about 10 mg/kg, about 0.1 to about 5 mg/kg, or about 0.1 to about 2.5 mg/kg body weight of the subject. In another aspect, the therapeutically effect amount of the at least one aminosterol or a salt or derivative thereof in the methods of the invention can be, for example, about 0.001 to about 500 mg/day, about 0.001 to about 250 mg/day, about 0.001 to about 125 mg/day, about 0.001 to about 50 mg/day, about 0.001 to about 25 mg/day, or about 0.001 to about 10 mg/day.

In any embodiment herein, the method results in a decrease in the number of instances in which the subject cannot attain erection, and the decrease in number of instances in which the subject cannot attain erection comprises a reduction in number of instances in which the subject cannot attain erection over a defined period of time.

In any embodiment herein, the method results in a decreased severity of SZ over a defined period of time, wherein the decreased severity of SZ is measured by a medically recognized technique selected from the group consisting of The Clinical Assessment Interview for Negative Symptoms (CAINS), The Brief Negative Symptom Scale (BNSS), Scale for the Assessment of Positive Symptoms (SAPS), the Scale for the Assessment of Negative Symptoms (SANS), the Positive and Negative Symptoms Scale (PANSS), the Negative Symptom Assessment (NSA-16), the Clinical Global Impression Schizophrenia (CGI-SCH), computed tomography (CT), magnetic resonance imaging (MRI), magnetic resonance spectroscopy, functional MRI (fMRI), diffusion tensor imaging, single photon emission computed tomography (SPECT), and positron emission tomography (PET).

In some embodiments, each defined period of time is independently selected from the group consisting of about 1 day to about 10 days, about 10 days to about 30 days, about 30 days to about 3 months, about 3 months to about 6 months, about 6 months to about 12 months, and about greater than 12 months.

Administration may be via any route. Non-limiting examples include oral, nasal, sublingual, buccal, rectal, vaginal, intravenous, intra-arterial, intradermal, intraperitoneal, intrathecal, intramuscular, epidural, intracerebral, intracerebroventricular, transdermal, or any combination thereof. In some embodiments, the administration is non-oral administration. In some embodiments, the administration is nasal administration.

Nasal administration may be accomplished via insufflation of solids, liquids or powders, inhalation of a gas, or via inhalation of a mist comprising the at least one aminosterol in a suitable carrier and optionally excipients. Suitable carriers and excipients are known to the skilled artisan and include buffers such as sodium phosphate, sodium citrate, and citric acid; solubilizers such as glycols, small quantities of alcohol, transcutol (diethylene glycol monoethyl ether), medium chain glycerides, labrasol (saturated polyglycolyzed $C_8$-$C_{10}$ glyceride), surfactants and cyclodextrins; preservatives such as parabens, phenyl ethyl alcohol, benzalkonium chloride, EDTA (ethylene diaminetetraaceticacid), and benzoyl alcohol; antioxidants such as sodium bisulfite, butylated hydroxytoluene, sodium metabisulfite and tocopherol; humectants such as glycerin, sorbitol and mannitol; surfactants such as polysorbet; bioadhesive polymers such as mucoadhesives; and penetration enhancers such as dimethyl sulfoxide (DMSO).

Nasal administration via inhalation of a mist may employ the use of metered-dose spray pumps. Typical volumes of aminosterol-comprising mist, delivered via a single pump of a metered-dose spray pump may be about 20-100 µl, 100-150 µl, or 150-200 µl. Such pumps offer high reproducibility of the emitted dose and plume geometry. The particle size and plume geometry can vary within certain limits and depend on the properties of the pump, the formulation, the orifice of the actuator, and the force applied.

III. Methods of Determining and Compositions Comprising a "Fixed Dose" of an Aminosterol The present application relates to the surprising discovery of a method to determine a "fixed dose" of an aminosterol composition useful in treating, preventing and/or slowing or delaying the onset or progression of schizophrenia and/or a related symptom, where the dose is not age, size, or weight dependent but rather is individually calibrated. The "fixed aminosterol dose" obtained through this method yields highly effective results in treating the schizophrenia symptom(s) based on which the "fixed aminosterol dose" was determined, related symptoms along the "brain-gut" axis, and the underlying SZ. Further, contemplated herein are methods of leveraging this same "fixed dose" method for methods of prevention and/or slowing or delaying the onset of SZ.

A. "Fixed Aminosterol Dose"

A "fixed aminosterol dose," also referred to herein as a "fixed escalated aminosterol dose," which will be therapeutically effective is determined for each patient by establishing a starting dose of an aminosterol composition and a threshold for improvement of a particular SZ symptom. Following determining a starting aminosterol dosage for a particular patient, the aminosterol dose is then progressively escalated by a consistent amount over consistent time intervals until the desired improvement is achieved; this aminosterol dosage is the "fixed escalated aminosterol dosage" for that particular patient for that particular SZ symptom.

In exemplary embodiments, an orally administered aminosterol dose is escalated every about 3 to about 5 days by about 25 mg until the desired improvement is reached. Symptoms evaluated, along with tools for measuring SZ symptom improvement, may be specifically described below, including but not limited to constipation, hallucinations, sleep disturbances (e.g. REM disturbed sleep or circadian rhythm dysfunction), cognitive impairment, or depression.

This therapeutically effective "fixed aminosterol dose" is then maintained throughout treatment and/or prevention. Thus, even if the patient goes "off drug" and ceases taking the aminosterol composition, the same "fixed dose" is taken with no ramp up period following re-initiation of aminosterol treatment.

SZ may arise due to neurodegeneration (Rund 2009). Not to be bound by theory, it is believed that the aminosterol dose is dependent on the severity of nerve damage relating to the symptom establishing the "fixed aminosterol dose" threshold—e.g. for constipation, the dose may be related to the extent of nervous system damage in the patient's gut.

The aminosterol can be administered via any pharmaceutically acceptable means, such as by injection (e.g., IM, IV, or IP), oral, pulmonary, intranasal, etc. Preferably, the aminosterol is administered orally, intranasally, or a combination thereof.

Oral dosage of an aminosterol can range from about 1 to about 500 mg/day or any amount in-between these two values. Other exemplary dosages of orally administered aminosterols include, but are not limited to, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, or about 500 mg/day.

Intranasal dosages of an aminosterol are much lower than oral dosages of an aminosterol. Examples of such intranasal aminosterol low dosages include, but are not limited to, about 0.001 to about 6 mg/day, or any amount in-between these two values. For example, the low dosage of an intranasal administered aminosterol can be about 0.001, about 0.005, about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, or about 6 mg/day.

For intranasal (IN) administration, it is contemplated that the aminosterol dosage may be selected such that it would not provide any pharmacological effect if administered by any other route—e.g., a "subtherapeutic" dosage, and, in addition, does not result in negative effects. For example, Amino sterol 1436 is known to have the pharmacological effects of a reduction in food intake and weight loss. Therefore, in the IN methods of the invention, if the aminosterol is Aminosterol 1436 or a salt or derivative thereof, then if the IN Aminosterol 1436 dosage is administered via another route, such as oral, IP, or IV, then the Aminosterol 1436 dosage will not result in a noticeable reduction in food intake or noticeable weight loss. Similarly, squalamine is known to produce the pharmacological effects of nausea, vomiting and/or reduced blood pressure. Thus, in the IN methods of the invention, if the aminosterol is squalamine or a salt or derivative thereof, then if the IN squalamine dosage is administered via another route, such as oral, IP, or IV, then the squalamine dosage will not result in noticeable nausea, vomiting, and/or a reduction in blood pressure. Suitable exemplary aminosterol dosages are described above.

Dose Escalation:

When determining a "fixed aminosterol dosage" for a particular patient, a patient is started at a lower dose and then the dose is escalated until a positive result is observed for the symptom being evaluated. For example, constipation is exemplified in Example 1. Aminosterol doses can also be de-escalated (reduced) if any given aminosterol dose induces a persistent undesirable side effect, such as diarrhea, vomiting, or nausea.

The starting aminosterol dose is dependent on the severity of the symptom—e.g. for an SZ patient experiencing severe constipation, defined as less than one spontaneous bowel movement (SBM) a week, the starting oral aminosterol dose can be about 150 mg or greater. In contrast, for a patient having moderate constipation, e.g., defined as having more than one SBM a week, the starting aminosterol dose can be about 75 mg. Thus, as an example, a patient experiencing moderate constipation can be started at an aminosterol dosage of about 75 mg/day, whereas a patient experiencing severe constipation can be started at an aminosterol dosage of about 150 mg/day.

In other embodiments, a patient experiencing moderate symptoms (for the symptom being used to calculate a fixed escalated aminosterol dose) can be started at an oral aminosterol dosage of from about 10 mg/day to about 75 mg/day, or any amount in-between these values. For example, the starting oral aminosterol dosage for a moderate symptom can be about 10, about 15, about 20, about 25, about 30, about 35, about 40, about 45, about 60, about 65, about 70, or about 75 mg/day.

In yet further embodiments, when the SZ patient is experiencing severe symptoms (for the symptom being used to calculate the fixed escalated aminosterol dose), the patient can be started at an oral aminosterol dosage ranging from about 75 to about 175 mg/day, or any amount in-between these two values. For example, the starting oral aminosterol dosage for a severe symptom can be about 75, about 80, about 85, about 90, about 95, about 100, about 105, about 110, about 115, about 120, about 125, about 130, about 135, about 140, about 145, about 150 about 155, about 160, about 165, about 170, or about 175 mg/day.

In some embodiments, the starting oral aminosterol dose may be about 125 mg/day or about 175 mg/day; again dependent on the severity of the symptom, such as constipation.

Starting IN aminosterol dosages prior to dose escalation can be, for example, about 0.001 mg to about 3 mg, or any amount in-between these two values. For example, the starting aminosterol dosage for IN administration, prior to dose escalation, can be, for example, about 0.001, about 0.005, about 0.01, about 0.02, about 0.03, about 0.05, about 0.06, about 0.07, about 0.08, about 0.09, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 1.0, about 1.1, about 1.25, about 1.3, about 1.4, about 1.5, about 1.6, about 1.7, about 1.75, about 1.8, about 1.9, about 2.0, about 2.1, about 2.25, about 2.3, about 2.4, about 2.5, about 2.6, about 2.7, about 2.75, about 2.8, about 2.9, or about 3 mg/day.

In exemplary embodiments, the aminosterol dose is given periodically as needed. For example, the aminosterol dose can be given once per day. The aminosterol dose can also be given every other day, 2, 3, 4, or 5× per week, once/week, or 2×/week. In another embodiment, the aminosterol dose can be given every other week, or it can be administered for a first defined period of time of administration, followed by a cessation of administration for a second defined period of time, followed by resuming administration upon recurrence of SZ or a symptom of SZ.

When calculating a fixed escalated aminosterol dose, the dose can be escalated following any suitable period of time. In one embodiment, the aminosterol dose is escalated every about 3 to about 7 days by about a defined amount until a desired improvement is reached. For example, when the symptom being treated/measured is constipation, threshold improvement can be an increase of one SBM per week or at least a total of three bowel movements per week. In other embodiments, the aminosterol dose can be escalated every about 1, about 2, about 3, about 4, about 5, about 6, about 7, about 8, about 9, about 10, about 11, about 12, about 13, or about 14 days. In other embodiments, the aminosterol dose can be escalated about 1×/week, about 2×/week, about every other week, or about 1×/month.

During dose escalation, the aminosterol dosage can be increased by a defined amount. For example, when the aminosterol is administered orally, the dose can be escalated in increments of about 5, about 10, about 15, about 20, about 25, about 30, about 35, about 40, about 45, or by about 50 mg. When the aminosterol is administered intranasally, then the dosage can be increased in increments of about, for example, about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

Exemplary symptoms that can be used as an endpoint to determine aminosterol dosage for a SZ patient's fixed escalated aminosterol dosage are described herein and include, but are not limited to, (a) reduced social engagement, social withdrawal, and/or social isolation; (b) reduced emotional expression; (c) disorganized or irrational behavior; (d) disorganized or irrational thinking; (e) disorganized or irrational speech; (f) aggression or anger; (g) anxiety; (h) compulsive behavior; (i) excitability; (j) repetitive movements; (k) self-harm; (l) delusions; (m) amnesia; (n) emotional instability, including difficulty controlling emotions; (o) hallucinations; (p) depression; (q) constipation; (r) neurodegeneration associated with schizophrenia; (s) sleep problem, sleep disorder, and/or sleep disturbance; (t) cognitive impairment; (u) feelings of fright and/or paranoia; (v) false beliefs; (w) distorted thoughts; (x) lack of emotion or a very limited range of emotions; (y) catatonia; (z) impaired motor behavior and coordination; (aa) inability to make decisions; (bb) forgetting or losing things; (cc) poor executive functioning; (dd) ADHD, trouble focusing, paying attention and/or difficulty concentrating; (ee) difficulty with working memory; (ff) lack of motivation; (gg) reduced energy or apathy; (hh) reduced speech; (ii) loss of pleasure or interest in life; (jj) poor hygiene and grooming habits; (kk) hypertension; (ll) hypotension; (mm) sexual dysfunction, such as impotence and/or loss of libido, and/or (nn) cardiovascular disease.

B. Aminosterols

U.S. Pat. No. 6,962,909, entitled "Treatment of neovascularization disorders with squalamine," discloses various aminosterols, and this disclosure is specifically incorporated by reference with respect to its teaching of aminosterol compounds. Any aminosterol known in the art, including those described in U.S. Pat. No. 6,962,909, can be used in the disclosed compositions. In some embodiments, the aminosterol present in the compositions of the invention is Aminosterol 1436 or a salt or derivative thereof, squalamine or a salt or derivative thereof, or a combination thereof. An exemplary salt is a phosphate salt.

For instance, useful aminosterol compounds comprise a bile acid nucleus and a polyamine, attached at any position on the bile acid, such that the molecule exhibits a net positive charge contributed by the polyamine.

Thus, in some embodiments, the disclosed methods comprise administering a therapeutically effective amount of one or more aminosterols having the chemical structure of Formula I:

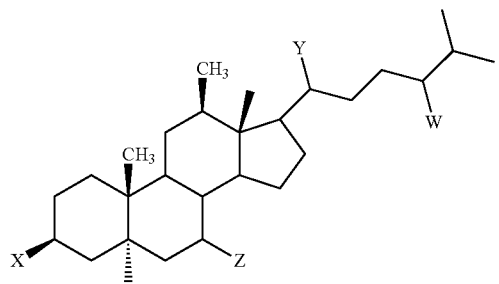

wherein,
W is 24S—$OSO_3$ or 24R—$OSO_3$;
X is 3β-$H_2N$—$(CH_2)_4$—NH—$(CH_2)_3$—NH— or 3α-$H_2N$—$(CH_2)_4$—NH—$(CH_2)_3$—NH—;
Y is 20R—$CH_3$; and
Z is 7α or 7β —OH.

In another embodiment, the aminosterol is one of the naturally occurring aminosterols (1-8) isolated from *Squalus acanthias*:

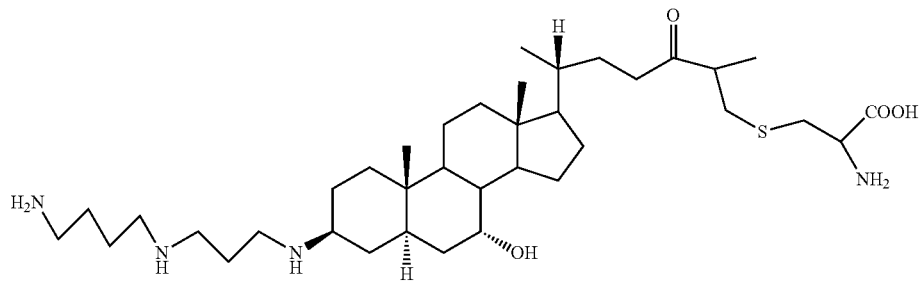

Compound 1

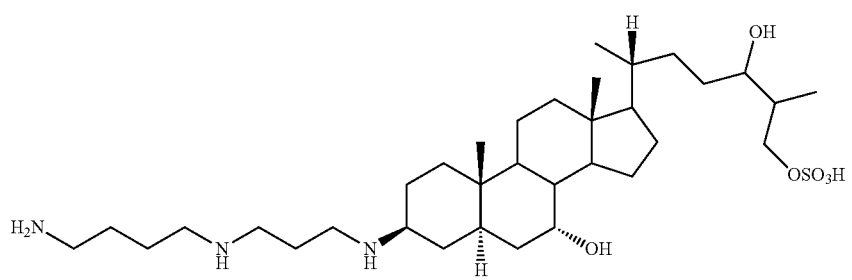

Compound 2

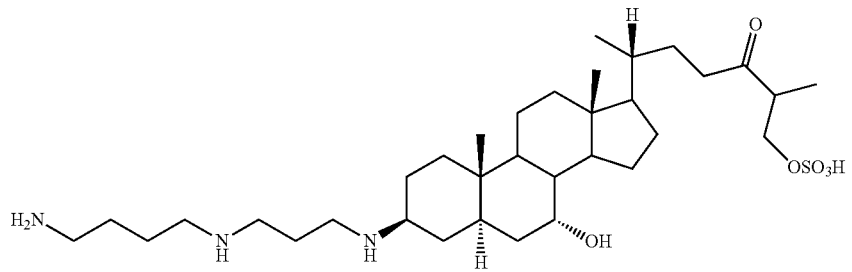

Compound 3

-continued

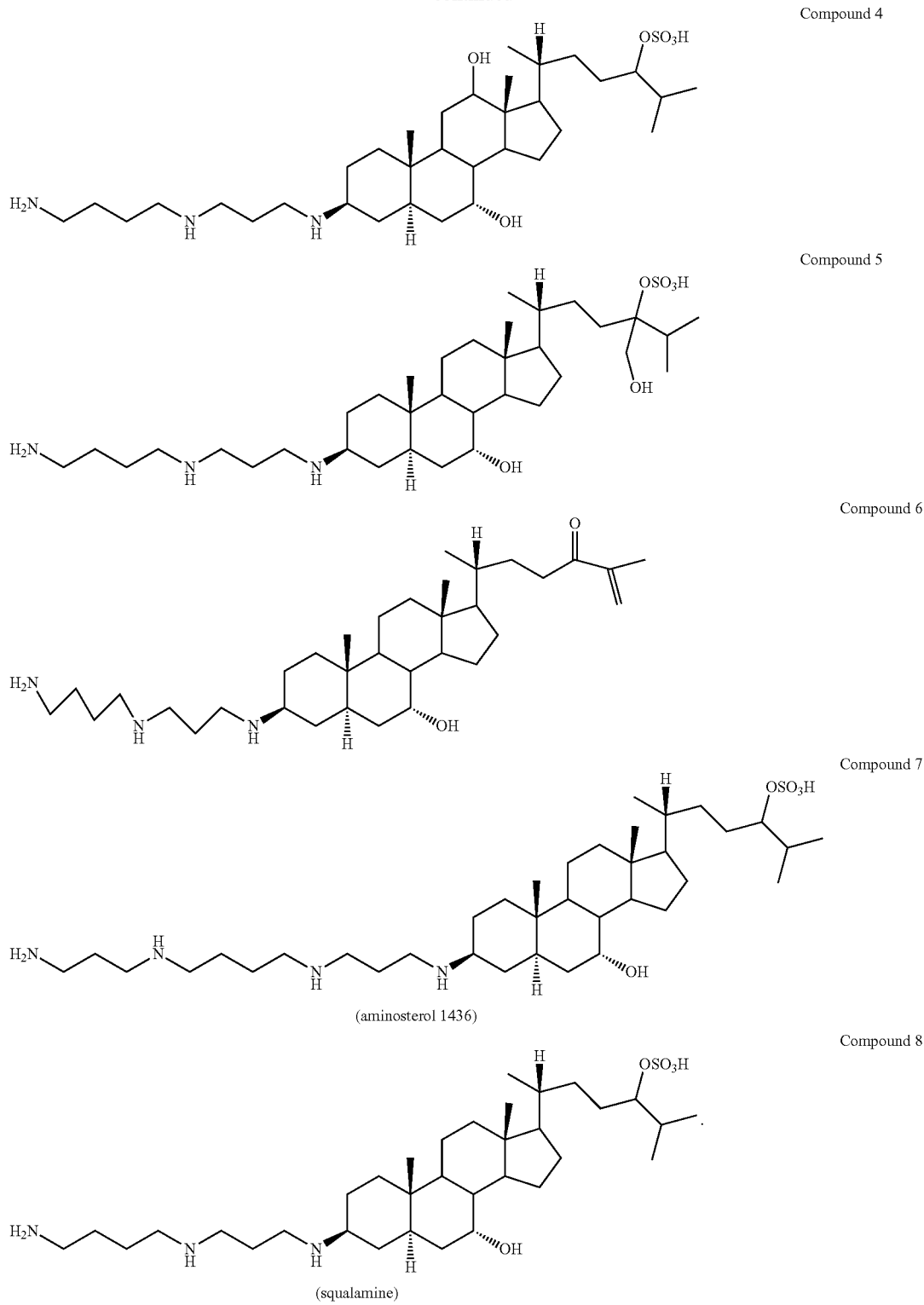

Compound 4

Compound 5

Compound 6

(aminosterol 1436)

Compound 7

Compound 8

(squalamine)

Variants or derivatives of known aminosterols, such as squalamine, Aminosterol 1436, or an aminosterol isolated from *Squalus acanthias*, may be used in the disclosed compositions and methods. In one aspect of the invention, the aminosterol is Amino sterol 1436 or a salt or derivative thereof or squalamine or a salt or derivative thereof.

In one embodiment, the aminosterol is a derivative of squalamine, aminosterol 1436, or another naturally occurring aminosterol modified through medicinal chemistry to improve biodistribution, ease of administration, metabolic stability, or any combination thereof. In another embodiment, the aminosterol is modified to include one or more of the following: (1) substitutions of the sulfate by a sulfonate, phosphate, carboxylate, or other anionic moiety chosen to circumvent metabolic removal of the sulfate moiety and oxidation of the cholesterol side chain; (2) replacement of a hydroxyl group by a non-metabolizable polar substituent, such as a fluorine atom, to prevent its metabolic oxidation or conjugation; and (3) substitution of various ring hydrogen atoms to prevent oxidative or reductive metabolism of the steroid ring system.

In yet another embodiment, the aminosterol comprises a sterol nucleus and a polyamine, attached at any position on the sterol, such that the molecule exhibits a net charge of at least +1, the charge being contributed by the polyamine.

In yet another embodiment, the aminosterol comprises a bile acid nucleus and a polyamine, attached at any position on the bile acid, such that the molecule exhibits a net positive charge being contributed by the polyamine.

In some embodiments, the compositions used in the methods of the invention comprise: (a) at least one pharmaceutical grade aminosterol; and optionally (b) at least one phosphate selected from the group consisting of an inorganic phosphate, an inorganic pyrophosphate, and an organic phosphate. In some embodiments, the aminosterol is formulated as a weakly water soluble salt of the phosphate. In some embodiments, the phosphate is an inorganic polyphosphate, and the number of phosphates can range from about 3 (tripolyphosphate) to about 400, or any number in-between these two values. In other embodiments, the phosphate is an organic phosphate which comprises glycerol 2 phosphates.

In some embodiments, the aminosterol is selected from the group consisting of: (a) squalamine or a pharmaceutically acceptable salt or derivative thereof; (b) a squalamine isomer; (c) a squalamine phosphate salt; (d) Aminosterol 1436 or a pharmaceutically acceptable salt or derivative thereof; (e) an aminosterol 1436 isomer; (f) an aminosterol 1436 phosphate salt; (g) an aminosterol comprising a sterol or bile acid nucleus and a polyamine, attached at any position on the sterol or bile acid, such that the molecule exhibits a net charge of at least +1, the charge being contributed by the polyamine; (h) an aminosterol which is a derivative of squalamine modified through medicinal chemistry to improve biodistribution, ease of administration, metabolic stability, or any combination thereof; (i) an aminosterol modified to include one or more of the following: (i) substitutions of the sulfate by a sulfonate, phosphate, carboxylate, or other anionic moiety chosen to circumvent metabolic removal of the sulfate moiety and oxidation of the cholesterol side chain; (ii) replacement of a hydroxyl group by a non-metabolizable polar substituent, such as a fluorine atom, to prevent its metabolic oxidation or conjugation; and (iii) substitution of various ring hydrogen atoms to prevent oxidative or reductive metabolism of the steroid ring system; (j) an aminosterol that can inhibit the formation of actin stress fibers in endothelial cells stimulated by a ligand known to induce stress fiber formation, having the chemical structure of Formula I (above); (k) a synthetic aminosterol; or (l) any combination thereof.

In some embodiments, the methods of the invention can employ a formulation of Aminosterol 1436 or squalamine as an insoluble salt of phosphate, polyphosphate, or an organic phosphate ester.

Any pharmaceutically acceptable salt of an aminosterol can be used in the compositions and methods of the invention. For example, a phosphate salt or buffer, free base, succinate, phosphate, mesylate or other salt form associated with low mucosal irritation can be utilized in the methods and compositions of the invention.

C. Routes of Administration

It is appreciated that the "fixed aminosterol dose" disclosed herein can be administered via any suitable route of administration, including but not limited to oral or intranasal delivery, injection (IP, IV, or IM) or a combination thereof.

Further, co-administration of the "fixed dose" with injectable (e.g., IP, IV, IM) aminosterol formulations is also contemplated herein. For injectable dosage forms, the dosage form can comprise an aminosterol at a dosage of, for example, about 0.1 to about 20 mg/kg body weight. In other embodiments, the effective daily dosing amount is about 0.1, about 0.5, about 1, about 2, about 3, about 4, about 5, about 6, about 7, about 8, about 9, about 10, about 11, about 12, about 13, about 14, about 15, about 16, about 17, about 18, about 19, or about 20 mg/kg body weight.

The invention also encompasses methods of treatment using a combination of an aminosterol composition administered via one route, e.g., oral, with a second aminosterol composition, comprising the same or a different aminosterol, administered via a different route, e.g., intranasal. For example, in a method of the invention, squalamine can be administered orally and aminosterol 1436 can be administered IN.

D. Dosing Period

The pharmaceutical composition comprising an aminosterol or a derivative or salt thereof can be administered for any suitable period of time, including as a maintenance dose for a prolonged period of time. Dosing can be done on an as needed basis using any pharmaceutically acceptable dosing regimen. Aminosterol dosing can be no more than 1× per day, once every other day, once every three days, once every four days, once every five days, once every six days, once a week, or divided over multiple time periods during a given day (e.g., twice daily).

In other embodiments, the composition can be administered: (1) as a single dose, or as multiple doses over a period of time; (2) at a maintenance dose for an indefinite period of time; (3) once, twice or multiple times; (4) daily, every other day, every 3 days, weekly, or monthly; (5) for a period of time such as about 1, about 2, about 3, or about 4 weeks, about 1, about 2, about 3, about 4, about 5, about 6, about 7, about 8, about 9, about 10, about 11, or about 12 months, about 1 year, about 1.5 years, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, about 23.5, about 24, about 24.5, or about 25 years, or (6) any combination of these parameters, such as daily administration for 6 months, weekly administration for 1 or more years, etc.

Yet another exemplary dosing regimen includes periodic dosing, where an effective dose can be delivered once every about 1, about 2, about 3, about 4, about 5, about 6 days, or once weekly.

In a preferred embodiment, the aminosterol dose is taken in the morning, i.e. on an empty stomach preferably within about two hours of waking up and may be followed by a period without food, such as for example about 60 to about 90 minutes. In other embodiments, the aminosterol dose is taken within about 15 min, about 30 min, about 45 min, about 1 hr, about 1.25 hrs, about 1.5 hrs, about 1.75 hrs, about 2 hrs, about 2.25 hrs, about 2.5 hrs, about 2.75 hrs, about 3 hrs, about 3.25 hrs, about 3.5 hrs, about 3.75 hrs, or about 4 hrs within waking up. In yet further embodiments, the aminosterol dose is followed by about period without food, wherein the period is at least about 30 min, about 45 mins, about 60 mins, about 1.25 hrs, about 1.5 hrs, about 1.75 hrs, or about 2 hrs.

Not to be bound by theory, it is believed that since aminosterols have an impact on circadian rhythms, likely due to ENS signaling thereof, taking the aminosterol dose in the morning enables the synchronization of all the autonomic physiological functions occurring during the day. In other embodiments of the invention, the aminosterol dosage is taken within about 15 mins, about 30 mins, about 45 mins, about 1 hour, about 1.25 hrs, about 1.5 hrs, about 1.75 hrs, about 2 hrs, about 2.25 hrs, about 2.5 hrs, about 2.75 hrs, about 3 hrs, about 3.25 hrs, about 3.5 hrs, about 3.75 hrs, or about 4 hrs of waking up. In addition, in other embodiments of the invention, following the aminosterol dosage the subject has a period of about 15 mins, about 30 mins, about 45 mins, about 1 hours, about 1.25 hrs, about 1.5 hrs, about 1.75 hrs, about 2 hrs, about 2.25 hrs, about 2.5 hrs, about 2.75 hrs, or about 3 hours without food.

In some embodiments, each defined period of time is independently selected from the group consisting of about 1 day to about 10 days, about 10 days to about 30 days, about 30 days to about 3 months, about 3 months to about 6 months, about 6 months to about 12 months, and about greater than 12 months.

E. Composition Components

In some embodiments, a pharmaceutical composition disclosed herein comprises one or more pharmaceutically acceptable carriers, such as an aqueous carrier, buffer, and/or diluent.

In some embodiments, a pharmaceutical composition disclosed herein further comprises a simple polyol compound, such as glycerin. Other examples of polyol compounds include sugar alcohols. In some embodiments, a pharmaceutical composition disclosed herein comprises an aqueous carrier and glycerin at about a 2:1 ratio.

The formulations may conveniently be presented in unit dosage form and may be prepared by any of the methods well known in the art of pharmacy. An exemplary oral dosage form is a tablet or capsule. An exemplary intranasal dosage form is a liquid or powder nasal spray. A nasal spray is designed to deliver drug to the upper nasal cavity, and can be a liquid or powder formulation, and in a dosage form such as an aerosol, liquid spray, or powder.

The aminosterol may be combined or coordinately administered with a suitable carrier or vehicle depending on the route of administration. As used herein, the term "carrier" means a pharmaceutically acceptable solid or liquid filler, diluent or encapsulating material. A water-containing liquid carrier can comprise pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories can be found in the U.S. Pharmacopeia National Formulary, 1857-1859, and (1990). Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acesulfame. Examples of flavoring agents are Magnasweet® (trademark of MAFCO), bubble gum flavor, and fruit flavors, and the like. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Any pharmaceutical used for therapeutic administration can be sterile. Sterility is readily accomplished by for example filtration through sterile filtration membranes (e.g., 0.2 micron membranes). Any pharmaceutically acceptable sterility method can be used in the compositions of the invention.

The pharmaceutical composition comprising an aminosterol derivatives or salts thereof will be formulated and dosed in a fashion consistent with good medical practice, taking into account the clinical condition of the individual patient, the method of administration, the scheduling of administration, and other factors known to practitioners.

F. Kits

Aminosterol formulations or compositions of the invention may be packaged together with, or included in a kit along with instructions or a package insert. Such instructions or package inserts may address recommended storage conditions, such as time, temperature and light, taking into account the shelf-life of the aminosterol or derivatives or salts thereof. Such instructions or package inserts may also address the particular advantages of the aminosterol or derivatives or salts thereof, such as the ease of storage for formulations that may require use in the field, outside of controlled hospital, clinic or office conditions.

The invention also provides a pharmaceutical pack or kit comprising one or more containers filled with one or more aminosterol pharmaceutical compositions disclosed herein. The kits may include, for instance, containers filled with an appropriate amount of an aminosterol pharmaceutical composition, either as a powder, a tablet, to be dissolved, or as a sterile solution. Associated with such container(s) can be a notice in the form prescribed by a governmental agency regulating the manufacture, use or sale of pharmaceuticals or biological products, which notice reflects approval by the agency of manufacture, use or sale for human administration. In addition, the aminosterol or a derivative or salt thereof may be employed in conjunction with other therapeutic compounds.

In other aspects, a kit comprising a nasal spray device as described herein is disclosed. In one aspect, the kit may comprise one or more devices as disclosed herein, comprising a disclosed low dose aminosterol composition, wherein the device is sealed within a container sufficient to protect the device from atmospheric influences. The container may be, for example, a foil, or plastic pouch, particularly a foil pouch, or heat sealed foil pouch. Suitable containers sufficient to adequately protect the device will be readily appreciated by one of skill in the art.

In one aspect, the kit may comprise one or more devices as disclosed herein, wherein the device may be sealed within a first protective packaging, or a second protective packaging, or a third protective packaging, that protects the physical integrity of the product. One or more of the first, second, or third protective packaging may comprise a foil pouch. The kit may further comprise instructions for use of the device. In one aspect, the kit contains two or more devices.

In one aspect, the kit may comprise a device as disclosed herein, and may further comprise instructions for use. In one aspect, the instructions may comprise visual aid/pictorial and/or written directions to an administrator of the device.

G. Patient Populations

The disclosed compositions can be used to treat a range of subjects, including human and non-human animals, including mammals, as well as immature and mature animals, including human children and adults. The human subject to be treated can be an infant, toddler, school-aged child, teenager, young adult, adult, or elderly patient.

In embodiments disclosed herein relating to prevention, particular patient populations may be selected based on being "at risk for" the development of one or more disorders. For example, genetic markers of schizophrenia (e.g. RTN4R) or family history may be used as signs to identify subjects likely to develop schizophrenia. Thus, in some embodiments relating to disorders for which certain genetic or hereditary signs are known, prevention may involve first identifying a patient population at risk based on genetic history or another risk factor. Alternatively, certain symptoms are considered early signs of particular disorders. Thus, in some embodiments, a patient population may be selected for being "at risk" for developing SZ based on age and experiencing constipation. Further genetic or hereditary signs may be used to refine the patient population.

IV. Methods of Prevention and/or Treatment with a "Fixed Dose" of Aminosterol

Aspects of this disclosure relate to methods of treating, preventing and/or slowing or delaying the onset or progression of schizophrenia and/or a related symptom by administration of a "fixed dose" of aminosterol as disclosed herein. As noted herein, one or more of the symptoms disclosed herein can be used to determine the fixed dose during the aminosterol dose escalation process.

Example 1 provides a detailed protocol for determining a "fixed aminosterol dose" based on improvement of one symptom associated with Parkinson's disease (PD), e.g., constipation. This example further details how this "fixed dose" successfully treated not only constipation, but also other non-dopamine related symptoms of PD, which therefore are applicable to treatment of schizophrenia.

As dopaminergic activity distinguishes PD from other neurodegenerative disorders and these data relate to symptoms that do not relate to this distinguishing feature, this dosing regime is believed to be extrapolatable both to other symptoms and other disorders including schizophrenia.

Not to be bound by theory, it is believed that establishing a patient-specific "fixed dose" based on hitting a threshold improvement in any of the symptoms listed below and administering this therapeutically effective fixed dose will successfully treat the initial symptom and one or more of the other symptoms. Further, to the extent that these symptoms are tied to an underlying disorder, administration of the therapeutically effective fixed dose is also believed to offer a means of treating, preventing, and/or delaying onset and/or progression of the underlying SZ disorder.

A. Schizophrenia

Diagnosis of SZ involves ruling out other mental health disorders and determining that symptoms are not due to substance abuse, medication or a medical condition. Determining a diagnosis of schizophrenia may include physical exam, imaging, psychiatric evaluation, and consulting the Diagnostic and Statistical Manual of Mental Disorders (DSM) or International Statistical Classification of Diseases and Related Health Problems (ICD-10).

If signs of disturbance are present for more than a month but less than six months, the diagnosis of SZ disorder is applied. Psychotic symptoms lasting less than a month may be diagnosed as brief psychotic disorder, and various conditions may be classed as psychotic disorder not otherwise specified. Schizoaffective disorder is diagnosed if symptoms of mood disorder are substantially present alongside psychotic symptoms. As, such embodiments of the present invention referring to "schizophrenia" may also intend schizophreniform disorder, schizoaffective disorder, and schizotypal personality disorder.

Psychotic symptoms may be present in several other mental disorders, including bipolar disorder, and borderline personality disorder. Delusions ("non-bizarre") are also present in delusional disorder, and social withdrawal in social anxiety disorder, avoidant personality disorder and schizotypal personality disorder. Schizophrenia cannot be diagnosed if symptoms of mood disorder are substantially present, or if symptoms of pervasive developmental disorder are present unless prominent delusions or hallucinations are also present. Schizophrenia is further complicated with obsessive-compulsive disorder (OCD), and it can be difficult to distinguish obsessions that occur in OCD from the delusions of SZ. In children hallucinations must be separated from typical childhood fantasies.

A urine drug screen must be performed to determine if the cause for symptoms could be drug intoxication or drug-induced psychosis. For example, a few people withdrawing from benzodiazepines experience a severe withdrawal syndrome which may last a long time and can resemble SZ. A general medical and neurological examination may also be needed to rule out medical illnesses which may rarely produce psychotic schizophrenia-like symptoms, such as metabolic disturbance, systemic infection, syphilis, HIV infection, epilepsy, and brain lesions. Stroke, multiple sclerosis, hyperthyroidism, hypothyroidism, and dementias such as Alzheimer's disease, Huntington's disease, frontotemporal dementia, and the Lewy body dementias may also be associated with schizophrenia-like psychotic symptoms. It may be necessary to rule out a delirium, which can be distinguished by visual hallucinations, acute onset and fluctuating level of consciousness, and indicates an underlying medical illness. Investigations are not generally repeated for relapse unless there is a specific medical indication or possible adverse effects from antipsychotic medication.

Brain imaging, such as CT and MRI scans, are currently used to rule out brain abnormalities. Structural alterations have been identified in SZ, most commonly enlarged ventricles, and decreased grey matter volume in the cortex and hippocampus. Studies using functional MRI have also shown that altered connectivity and activity present in schizophrenia.

Blood-based biomarkers those are obtained from plasma or serum samples. Since the prevalence of metabolic syndromes is increased in SZ patients, makers of those syndromes have been common targets of research. Differences between patients and controls have been found in insulin levels, insulin resistance, and glucose tolerance. These effects are generally small, however, and often present only in a subset of patients, which results from the heterogeneity of the disease.

In another embodiment, administration of a therapeutically effective fixed dose of an aminosterol composition to a SZ subject results in improvement of one or more symptoms of schizophrenia or on one or more clinically accepted scoring metrics, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In one embodiment of the invention, the progression or onset of SZ is slowed or prevented over a defined period of time, following administration of a fixed aminosterol dose according to the invention, to a subject in need, as measured by a medically-recognized technique. For example, the progression or onset of schizophrenia can be slowed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

The period of time over which the progression or onset of SZ is measured can be for example, one or more months or one or more years, e.g., about 6 months, about 1 year, about 18 months, about 2 years, about 36 months, about 3, about 4, about 5, about 6, about 7, about 8, about 9, about 10, about 11, about 12, about 13, about 14, about 15, about 16, about 17, about 18, about 19, or about 20 years, or any amount of months or years in between the values of about 6 months to about 20 years or more.

In another embodiment of the invention, SZ may be positively impacted by administration of a fixed aminosterol dose according to the invention. A "positive impact" includes for example slowing advancement of the SZ condition, improving one or more SZ symptoms, etc.

B. Schizophrenia Symptoms

I. Constipation

While often dismissed as strictly a gastrointestinal symptom, constipation is believed to be an early indicator of neurodegenerative disease to the extent that ENS degeneration can be indicative of later CNS degeneration. Indeed, not to be bound by theory, but constipation is observed in patients with SZ. Accordingly, method embodiments disclosed herein relate to the treatment of constipation or the treatment and/or prevention of an underlying disorder associated with constipation.

Constipation is defined as a lower than normal frequency of bowel movements in a fixed duration of time (e.g. less than 3 bowel movements per week). Constipation not only constitutes a major economic burden, but it also significantly affects the quality of life of the individual, contributing to social isolation and depression. Furthermore, the severity of the symptoms correlates negatively with patient reported quality of life.

Example 1 describes several tools used to measure and evaluate the effect of aminosterol treatment on constipation, including for example:

(1) Rome-IV Criteria for Constipation (7 criteria, with constipation diagnosis requiring two or more of the following: (i) straining during at least 25% of defecations, (ii) lumpy or hard stools in at least 25% of defecations, (iii) sensation of incomplete evacuation for at least 25% of defecations, (iv) sensation of anorectal obstruction/blockage for at least 25% of defecations; (v) manual maneuvers to facilitate at least 25% of defecations; (vi) fewer than 3 defecations per week; and (vii) loose stools are rarely present without the use of laxatives;

(2) Constipation—Ease of Evacuation Scale (from 1-7, with 7=incontinent, 4=normal, and 1=manual disimpaction);

(3) Bristol Stool Chart, which is a patient-friendly means of categorizing stool characteristics (assessment of stool consistency is a validated surrogate of intestinal motility) and stool diary;

(4) Unified Parkinson's Disease Scale (UPSRS), section 1.11 (Constipation Problems);

(5) Patient Assessment of Constipation Symptoms (PAC-SYM); and (5) Patient Assessment of Constipation Quality of Life (PAC-QOL).

Examples of characteristics of constipation that can be positively affected by the method of the invention include, but are not limited to, frequency of constipation, duration of constipation symptoms, bowel movement frequency, stool consistency, abdominal pain, abdominal bloating, incomplete evacuation, unsuccessful attempts at evacuation, pain with evacuation, and straining with evacuation. Potentially all of these characteristics can be positively impacted by the methods of the invention. Further, assessments of these characteristics are known in the art, e.g. spontaneous bowel movements (SBMs)/week, stool consistency (Bristol Stool Form Scale) (Lewis and Heaton 1997; Heaton et al. 1992), ease of passage (Ease of Evacuation Scale) (Andresen et al. 2007), rescue medication use and symptoms and quality of life related to bowel function (PAC-SYM (Frank et al. 1999) and PAC-QOL (Marquis et al. 2005)).

The methods of using a therapeutically effective fixed dose of an aminosterol composition according to the invention to treat and/or prevent constipation associated with schizophrenia preferably results in an increase in the number of spontaneous bowel movements per week and/or an improvement in other stool conditions. The increase can be, for example, an increase of between 1 to 3 spontaneous bowel movements in a week, or, optionally, full restoration of regular bowel function.

Figure 1A:
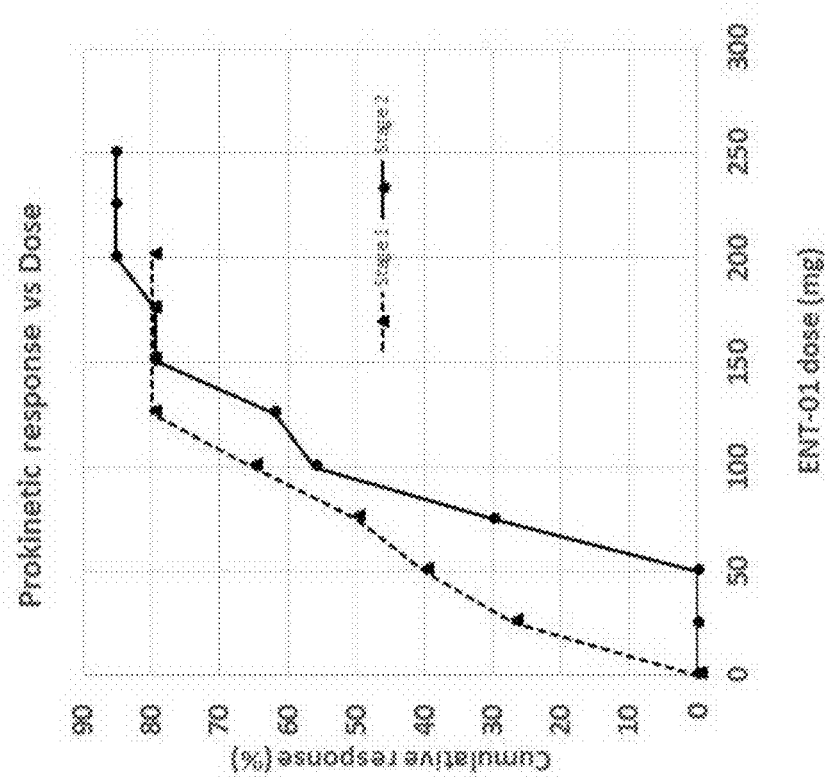

Data detailed in Example 1 shows that 80% of subjects responded to aminosterol treatment with improved bowel function (see FIG. 1A), with the cumulative response rate increasing in a dose-dependent fashion from 25% at 25 mg to a maximum of 80% at 200 mg (Stage 1, FIG. 1A). In Stage 2 of the study, the response rate increased in a dose-dependent fashion from 26% at 75 mg to 85.3% at 250 mg (FIG. 1A). The dose required for a bowel response was patient-specific and varied from 75 mg to 250 mg. The median efficacious dose was 100 mg.

The average CSBM/week increased from 1.2 at baseline to 3.8 at fixed dose (216% improvement) and SBM increased from 2.6 at baseline to 4.5 at fixed dose (73% improvement). Use of rescue medication decreased from 1.8/week at baseline to 0.3 at fixed dose (83% decrease). Consistency based on the Bristol stool scale also improved, increasing from mean 2.7 to 4.1 (52% improvement) and ease of passage increased from 3.2 to 3.7 (16% improvement). Subjective indices of wellbeing (PAC-QOL) and constipation symptoms (PAC-SYM) also improved during treatment.

The dose that proved efficacious in inducing a bowel response was strongly related to constipation severity at baseline (FIG. 1B); patients with baseline constipation of <1 CSBM/week required higher doses for a response (mean 192 mg) than patients with ≥1 CSBM/week (mean 120 mg).

In one embodiment of the invention, treatment of a SZ subject having constipation with an aminosterol in a method described herein results in an improvement of one or more characteristics of constipation associated with SZ. The improvement can be, for example, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375 or about 400%. Examples of constipation characteristics that can be improved by the methods of the invention include, but are not limited to, frequency of constipation, duration of constipation symptoms, bowel movement frequency, stool consistency, abdominal pain, abdominal bloating, incomplete evacuation, unsuccessful attempts at evacuation, pain with evacuation, and straining with evacuation. Measurement of a constipation characteristic can be done using any clinically recognized scale or tool.

One surprising discovery that resulted from the experiments described herein related to aminosterol dosing. It was surprisingly discovered that the dose of aminosterol required to obtain a positive impact on a symptom being evaluated, referred to herein as a "fixed escalated aminosterol dose," is patient specific. Moreover, it was discovered that the fixed escalated aminosterol dose is not dependent upon age, size, or weight but rather is individually calibrated. Further, it was discovered that the severity of constipation correlates with a higher required "fixed escalated aminosterol dose." It is theorized that the aminosterol dose required to obtain a positive effect in a subject for the symptom being evaluated correlates with the extent of neuronal damage. Thus, it is theorized that greater neuronal damage correlates with a higher required aminosterol dose to obtain a positive effect in a subject for the symptom being evaluated. The observation that the aminosterol dose required to achieve a desired response increases with constipation severity supports the hypothesis that the greater the burden of αS impeding neuronal function, the higher the dose of aminosterol required to restore normal bowel function.

Moreover, the data described in Example 1 confirms the hypothesis that gastrointestinal dysmotility in PD results from the progressive accumulation of αS in the ENS, and that aminosterol treatment can restore neuronal function by displacing αS and stimulating enteric neurons. These results demonstrate that the ENS in PD is not irreversibly damaged and can be restored to normal function.

In calibrating the fixed aminosterol dose for a specific SZ patient, the starting dose is varied based upon the severity of the constipation (when constipation is used as the schizophrenia symptom to be evaluated). Thus, for subjects with severe constipation, e.g., subjects with 1 or less CSBM or SMB per week, oral aminosterol dosing is started at about 100 to about 175 mg or more (or any amount in-between these values as described herein). For subjects with less severe constipation, e.g., more than 1 CSBM or SBM per week, oral aminosterol dosing is started at about 25 to about 75 mg (or any amount in-between these values as described herein). Dosing for both patients is then escalated by defined amounts over a defined period of time until the fixed escalated dose for the patient is identified. Amino sterol doses can also be de-escalated (reduced) if any given aminosterol dose induces a persistent undesirable side effect, such as diarrhea, vomiting, or nausea.

For example, for SZ patients with severe constipation, a starting oral aminosterol dosage can be from 75 mg up to about 300 mg/day, or any amount in-between these two values. In other embodiments, the starting oral aminosterol dosage for severely constipated patients can be, for example, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, or about 300 mg/day. A "fixed escalated" oral aminosterol dose for a severely constipated patient is likely to range from about 75 mg up to about 500 mg. As described in Example 1, a positive effect was defined as a dose that resulted in a CSBM within 24 hours of dosing on at least 2 of 3 days at a given dose.

For SZ patients with less severe constipation, oral aminosterol dosing is started at about 10 to about 75 mg/day, or any amount in-between these two values as described herein. For example, starting oral aminosterol dosage for patients with moderate to mild constipation can be about 1, about 5, about 10, about 15, about 20, about 25, about 30, about 35, about 40, about 45, about 50, about 55, about 60, about 65, about 70, up to less than or equal to about 75 mg/day. A fixed escalated oral aminosterol dose for a mild or moderately constipated patient is likely to range from about 5 mg up to about 350 mg/day, or any amount in-between these two values as described herein.

2. Hallucinations

Another symptom that can be associated with SZ is hallucinations. A hallucination is a sensory impression or perception of an object or event, in any of the 5 senses (sight, touch, sound, smell, or taste) that has no basis in external stimulation. Hallucinations can have debilitating impact on the subject's health and life by causing harm to self or others, by making it difficult for the subject to function normally in everyday situations, and by causing sleep disruption. Examples of hallucinations include "seeing" someone not there (visual hallucination), "hearing" a voice not heard by others (auditory hallucination), "feeling" something crawling up your leg (tactile hallucination), "smelling" (olfactory), and "tasting" (gustatory). Other examples of hallucination types include hypnagogic hallucination (a vivid, dreamlike hallucination occurring at sleep onset), hypnopompic hallucination (a vivid, dreamlike hallucination occurring on awakening), kinesthetic hallucination (a hallucination involving the sense of bodily movement), and somatic hallucination, a hallucination involving the perception of a physical experience occurring within the body.

Hallucinations can be the result of SZ. In a preferred embodiment, the aminosterol compositions of the invention reverse the dysfunction of the schizophrenia and treat the hallucination.

Further still, hallucinations may be caused by a sensory loss associated with schizophrenia. The sensory loss can be, for example, visual, auditory, gustatory, tactile, or olfactory. In a preferred embodiment, the fixed dose aminosterol compositions of the invention reverse the dysfunction of the sensory loss and treat the hallucination.

The methods of using a therapeutically effective fixed dose of an aminosterol composition according to the invention to treat and/or prevent hallucinations associated with schizophrenia preferably result in a decrease in hallucinations. The decrease can be, for example, a reduction in occurrences of hallucinations by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The methods of the invention may also result in the subject being hallucination-free. The hallucination can comprise, for example, a visual, auditory, tactile, gustatory or olfactory hallucination. The improvement can be measured using any clinically recognized assessment or tool.

Example 1 describes several tools used to measure and evaluate the effect of aminosterol treatment on hallucinations, including for example:

(1) The University of Miami Parkinson's Disease Hallucinations Questionnaire (UM-PDHQ);

(2) Unified Parkinson's Disease Scale (UPSRS), section 1.2 (Hallucinations and Psychosis); and (3) direct questioning.

As described in Example 1, the PDHQ score improved from 1.3 at baseline to 0.9 during wash-out. Hallucinations were reported by 5 patients at baseline and delusions in 1 patient. Both hallucinations and delusions improved or disappeared in 5 of 6 patients during treatment and did not return for 4 weeks following discontinuation of aminosterol treatment in 1 patient and 2 weeks in another. In one patient the hallucinations disappeared at 100 mg, despite not having reached the colonic prokinetic dose at 175 mg. Further, unlike stool-related indices, the improvement in many CNS symptoms persisted during wash-out.

3. Sleep Disturbance/Sleep Problems Associated with Schizophrenia (e.g., REM Disturbed Sleep or Circadian Rhythm Dysfunction)

Sleep disturbances can be associated with SZ. Normal sleep is critically important for the proper functioning of many organ systems, the most important of which is the brain. Disturbances in normal sleep patterns are closely associated with the normal aging process, with the development of cognitive impairment, with impaired memory deposition and consolidation and with the occurrence of neurodevelopmental, neuroaffective and neurodegenerative disorders. The alternating pattern of sleep and wakefulness occurring every 24 hours is known as the circadian rhythm. The rhythm is set by the "Zeitgeber" (time setter), an entity known as the suprachiasmatic nucleus (SCN) and located in the hypothalamus. The SCN is normally "entrained" or synchronized by the external light-dark cycle. This relationship between external light and dark and the sleep wake cycle synchronized to it by the SCN can be over ridden during periods of hunger by neural signals emanating in the gut and relayed to the hypothalamus. The circadian sleep-wake cycle can also shift in response to changes in external light-dark cycles, such as the desynchronization that occurs during travel from one time zone to another (jet-lag). Under such circumstances, a progressive adjustment occurs until the SCN is resynchronized with the external light-dark cycle. A similar "phase-shift" and adjustment occurs in night-shift workers.

Under normal circumstances, the properly functioning SCN, synchronized to the external light-dark cycle and to neural signals emanating from the enteric nervous system, will regulate the sleep-wake cycle by sending neural and chemical signals to the surrounding structures and to portions of the brain stem involved in sleep and wakefulness. An individual with a properly functioning hypothalamus and brain stem will go to bed and fall asleep within minutes, remain asleep throughout the night, wake up in the morning and remain awake and alert throughout the day. During the night, the asleep individual will experience several cycles of sleep, beginning with light sleep, progressing through rapid eye movement sleep (REM-sleep) to deep sleep and back. Each complete sleep period lasts about 90 minutes. Periods of REM-sleep are closely associated with dreaming. During REM-sleep, neural signals emanating from certain parts of the brain stem ensure that skeletal muscles become "atonic" or are paralyzed, such that the individual can't "act out" their dreams.

Certain diseases and conditions may impair the normal functioning of the "Zeitgeber" or circadian clock, including SZ. These conditions may be reversible, such as desynchronization resulting from schizophrenia. In contrast, damage to the nerves carrying light-dark related information from the retina to the SCN (conditions which may lead to blindness), or damage to the enteric nerves and neural structures which relay messages from the intestine to the SCN (conditions which may lead to neurodegenerative disorders) can cause permanent dysfunction of the circadian rhythm and abnormal sleep behavior.

Dysfunction of the circadian rhythm manifests first and foremost by abnormal sleep patterns. Such abnormalities typically are mild at onset and worsen progressively over time. A common symptom of sleep disorder is a delay in the onset of sleep. This delay can be as long as several hours, and the individual may not be able to fall asleep until the early hours of the morning. Another common symptom is sleep fragmentation, meaning that the individual awakens several times during the course of the night. Once awakened, the individual may not be able to get back to sleep, and each awake fragment may last an hour or more, further reducing "total sleep time," which is calculated by subtracting total time of the awake fragments from total time spent in bed. Total sleep time also diminishes with age, from about 14 to about 16 hours a day in newborns, to about 12 hours by one year of age, to about 7 to about 8 hours in young adults, progressively declining to about 5 to about 6 hours in elderly individuals. Total sleep time can be used to calculate an individual's "sleep age" and to compare it to their chronologic age. Significant discrepancies between sleep age and chronologic age are a reflection of the severity of the sleep disorder. "Sleep efficiency," defined as the percentage of the time spent in bed asleep is another index that can be used to determine the severity of the sleep disorder. Sleep efficiency is said to be abnormal when the percentage is below about 70%.

Sleep disorders and/or sleep disturbances include but are not limited to REM-behavior disorders, disturbances in the circadian rhythm, delayed sleep onset, sleep fragmentation, and hallucinations. Other sleep disorders or disturbances that can be treated and/or prevented according to the disclosed methods include but are not limited to hypersomnia (i.e., daytime sleepiness), parasomnias (such as nightmares, night terrors, sleepwalking, and confusional arousals), periodic limb movement disorders (such as Restless Leg Syndrome), jet lag, narcolepsy, advanced sleep phase disorder, non-24 hour sleep-wake syndrome.

Individuals with severe sleep disorders also typically suffer from day-time sleepiness. This can manifest as daytime "napping" for an hour or two, to "dosing off" for a few minutes during a film or to "micro-sleep" episodes lasting seconds to minutes, and of which the individual may or may not be aware. Narcolepsy is a rare and extreme form of day-time sleepiness, with the sudden onset of sleep causing the individual to fall down. Another form of sleep disturbance involves periods of loud snoring alternating with periods of "sleep apnea" (arrested breathing), a condition known as "sleep-disordered breathing." "REM-behavior disorder" (RBD) or "REM-disturbed sleep", is yet another sleep disturbance which occurs as a result of dysfunctional neural communication between the enteric nervous system, structures responsible for sleep in the brain stem and the SCN. In individuals with RBD, neural signaling which causes the paralysis (atonia) of muscles under voluntary control is impaired or altogether absent. As a consequence, "acting-out" of dreams occurs. This can range at one end of the spectrum from an increase in muscle tone detectable by electromyography (EMG) and accompanied by small movements of the hands and feet during REM sleep, to violent thrashing of arms and legs, kicking or punching a bed partner, speaking out loud or screaming, at the other end of the spectrum. Episodes of RBD can occur several times a night or very infrequently, once every few months. They can also be clustered, several occurring within a week, followed by periods of normal sleep. Unless the condition can be treated with a medication that restores normal functioning of the circadian rhythm and improves sleep patterns, individuals with RBD progress to neurodegenerative disorders.

Sleep disturbances include but are not limited to RBD, circadian rhythm dysfunction, delayed sleep onset, restless leg syndrome, daytime sleepiness, and sleep fragmentation.

Sleep is increasingly recognized as important to public health, with sleep insufficiency linked to motor vehicle crashes, industrial disasters, and medical and other occupational errors. Unintentionally falling asleep, nodding off while driving, and having difficulty performing daily tasks because of sleepiness all may contribute to these hazardous outcomes. Persons experiencing sleep insufficiency are also more likely to suffer from chronic diseases such as hypertension, diabetes, depression, and obesity, as well as from cancer, increased mortality, and reduced quality of life and productivity. Sleep insufficiency may be caused by broad scale societal factors such as round-the-clock access to technology and work schedules, but sleep disorders such as insomnia or obstructive sleep apnea also play an important role. An estimated 50-70 million US adults have a sleep or wakefulness disorder.

A "normal" or "restful" sleep period is defined as a sleep period uninterrupted by wakefulness. Alternatively, a said period can be defined by the recommended or appropriate amount of sleep for the subject's age category, e.g., (i) infants 0-3 months=about 11 to about 19 hours; (ii) infants about 4 to about 11 months=about 12 to about 18 hours; (iii) toddlers about 1 to about 2 years=about 9 to about 16 hours; (iv) preschoolers about 3 to about 5 years=about 10 to about 14 hours; (v) school-aged children about 6 to about 13 years=about 7 to about 12 hours; (v) teenagers about 14 to about 17 years=about 7 to about 11 hours; (vi) young adults about 18 to about 25 years=about 6 to about 11 hours; (vii) adults about 26 to about 64 years=about 6 to about 10 hours; and (viii) older adults ≥65 years=about 5 to about 9 hours. Thus, for treating sleep disturbance in a subject, the treatment can result in a restful sleep period of at least about 4, about 5, about 6, about 7, about 8, about 9, about 10, about 11, or about 12 hours.

How much sleep is needed by a subject varies between individuals but generally changes with age. The National Institutes of Health suggests that school-age children need at least 10 hours of sleep daily, teens need 9-10 hours, and adults need 7-8 hours. According to data from the National Health Interview Survey, nearly 30% of adults reported an average of ≤6 hours of sleep per day in 2005-2007. Further, in 2009, only 31% of high school students reported getting at least 8 hours of sleep on an average school night. Similar recommendations are provided by the National Sleep Foundation:

TABLE 1

| Age | Recommended | May be appropriate | Not recommended |
| --- | --- | --- | --- |
| Newborns 0-3 months | 14 to 17 hours | 11 to 13 hours 18 to 19 hours | Less than 11 hours More than 19 hours |
| Infants 4-11 months | 12 to 15 hours | 10 to 11 hours 16 to 18 hours | Less than 10 hours More than 18 hours |
| Toddlers 1-2 years | 11 to 14 hours | 9 to 10 hours 15 to 16 hours | Less than 9 hours More than 16 hours |
| Preschoolers 3-5 years | 10 to 13 hours | 8 to 9 hours 14 hours | Less than 8 hours More than 14 hours |
| School-aged Children 6-13 years | 9 to 11 hours | 7 to 8 hours 12 hours | Less than 7 hours More than 12 hours |
| Teenagers 14-17 years | 8 to 10 hours | 7 hours 11 hours | Less than 7 hours More than 11 hours |
| Young Adults 18-25 years | 7 to 9 hours | 6 hours 10 to 11 hours | Less than 6 hours More than 11 hours |
| Adults 26-64 years | 7 to 9 hours | 6 hours 10 hours | Less than 6 hours More than 10 hours |
| Older Adults ≥65 years | 7 to 8 hours | 5 to 6 hours 9 hours | Less than 5 hours More than 9 hours |

There are several different scientifically acceptable ways to measure a sleep period uninterrupted by wakefulness. First, electrodes attached to the head of a subject can measure electrical activity in the brain by electroencephalography (EEG). This measure is used because the EEG signals associated with being awake are different from those found during sleep. Second, muscle activity can be measured using electromyography (EMG), because muscle tone also differs between wakefulness and sleep. Third, eye movements during sleep can be measured using electro-oculography (EOG). This is a very specific measurement that helps to identify Rapid Eye Movement or REM sleep. Any of these methods, or a combination thereof, can be used to determine if a subject obtains a restful sleep period following administration of at least one aminosterol or a salt or derivative thereof to the subject.

Further, circadian rhythm regulation can be monitored in a variety of ways, including but not limited to monitoring wrist skin temperature as described by Sarabia et al. 2008. Similarly symptoms of RBD can be monitored using a daily diary and RBD questionnaire (Stiasny-Kolster et al. 2007).

In some embodiments, administration of a therapeutically effective fixed dose of an aminosterol composition to a SZ patient with disturbed sleep results in improvement in frequency of normal or restful sleep as determined by a clinically recognized assessment scale for one or more types of sleep dysregulation, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

In some embodiments, (a) the sleep disorder or sleep disturbance comprises a delay in sleep onset, sleep fragmentation, REM-behavior disorder, sleep-disordered breathing including snoring and apnea, day-time sleepiness, microsleep episodes, narcolepsy, circadian rhythm dysfunction, REM disturbed sleep, or any combination thereof; (b) the sleep disorder or sleep disturbance comprises REM-behavior disorder, which comprises vivid dreams, nightmares, and acting out the dreams by speaking or screaming, or fidgeting or thrashing of arms or legs during sleep; (c) treating the sleep problem, sleep disorder, or sleep disturbance prevents or delays the onset and/or progression of the schizophrenia; (d) the method results in a positive change in the sleeping pattern of the subject; wherein the positive change is defined as: (i) an increase in the total amount of sleep obtained of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or (ii) a percent decrease in the number of awakenings during the night selected from the group consisting of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%; and/or (f) as a result of the method the subject obtains the total number of hours of sleep recommended by a medical authority for the age group of the subject.

Example 1 describes several tools used to measure and evaluate the effect of aminosterol treatment on sleep, including for example:

(1) Sleep Diary (participants completed a sleep diary on a daily basis throughout the study. The diaries included time into bed and estimated time to sleep as well as wake time and duration during the night);

(2) I-Button Temperature Assessment. The I-Button is a small, rugged self-sufficient system that measures temperature and records the results in a protected memory section. The Thermochron I-Button DS1921H (Maxim Integrated, Dallas, Tex.) was used for skin temperature measurement. I-Buttons were programmed to sample every 10 mins., and attached to a double-sided cotton sport wrist band using Velcro, with the sensor face of the I-Button placed over the inside of the wrist, on the radial artery of the dominant hand. Subjects removed and replaced the data logger when necessary (i.e., to have a bath or shower). The value of skin temperature assessment in sleep research is that the endogenous skin warming resulting from increased skin blood flow is functionally linked to sleep propensity. From the collected data, the mesor, amplitude, acrophase (time of peak temperature), Rayleight test (an index of interdaily stability), mean waveforms are calculated);

(3) Unified Parkinson's Disease Rating Scale (UPDRS), sections 1.7 (sleep problems), 1.8 (daytime sleepiness) and 1.13 (fatigue);

(4) Parkinson's Disease Fatigue Scale (PFS-16);

(5) REM Sleep Behavior Disorder Screening Questionnaire; and (6) Parkinson's Disease Sleep Scale.

Figure 3:
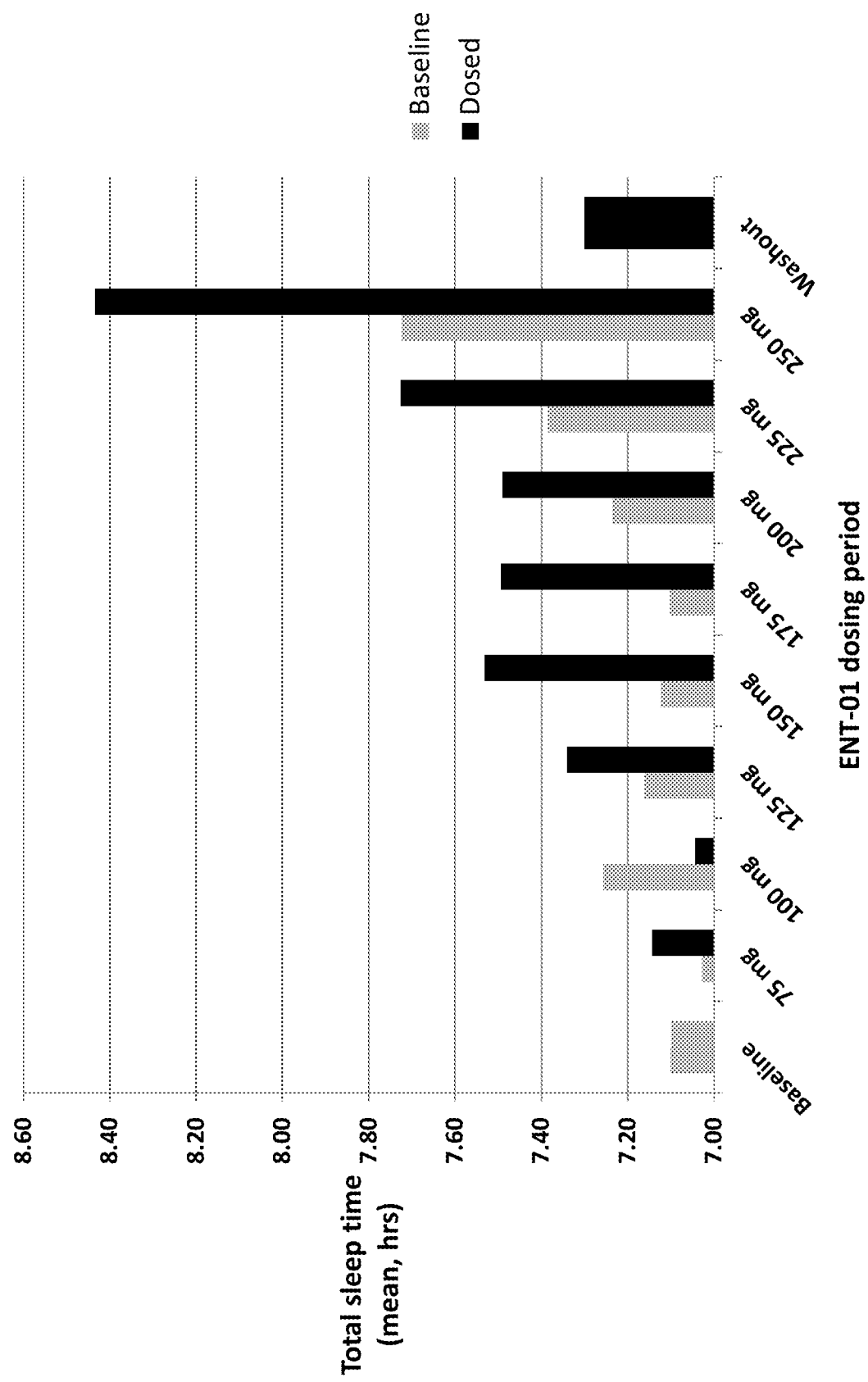
FIG. 3 is a chart of total sleep time in relation to squalamine dose. Total sleep time was obtained from the sleep diary by subtracting awake time during the night from total time spent in bed. Total sleep time per night was logged for each patient at baseline, each dosing period and at washout, and the means were determined. The light grey bar represents the baseline value for each cohort at a given dose level and the dark grey bar represents the value for the same cohort at the stated dose of squalamine (ENT-01). The number of patients represented at each value are: Baseline, 33; 75 mg, 21; 100 mg, 28; 125 mg, 18; 150 mg, 15; 175 mg, 12; 200 mg, 7; 225 mg, 3; 250 mg, 2; washout, 33. P values were as follows: 75 mg, p=0.4; 100 mg, p=0.1; 125 mg, p=0.3; 150 mg, p=0.07; 175 mg, p=0.03; 200 mg, p=0.3; 225 mg, p=0.5; 250 mg, p=0.3; wash-out, p=0.04 (paired t test).
Figure 4:
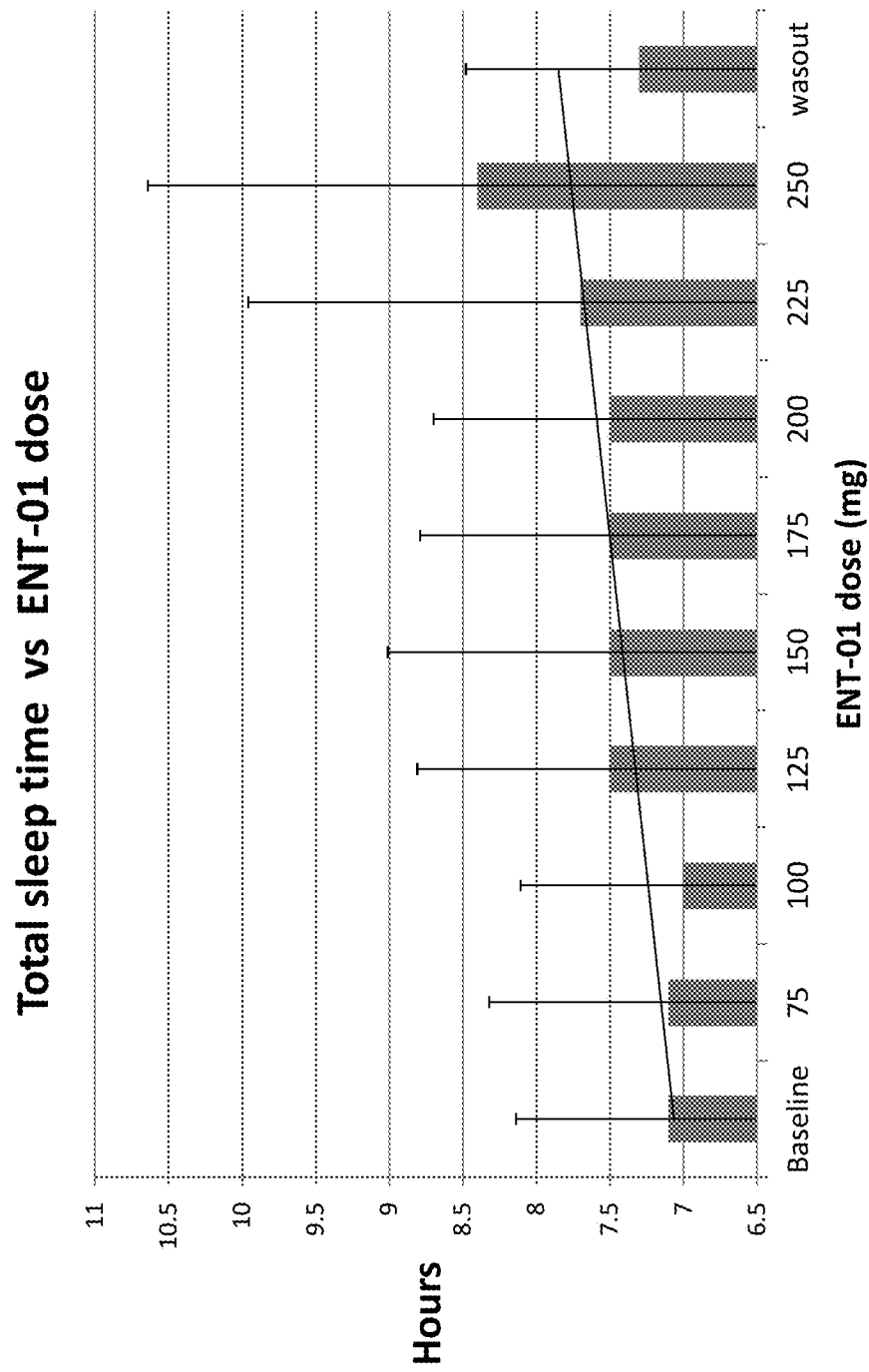
FIG. 4 shows total sleep time vs the dose of squalamine (ENT-01), with total sleep time increasing progressively from baseline to 250 mg.
Figure 5:
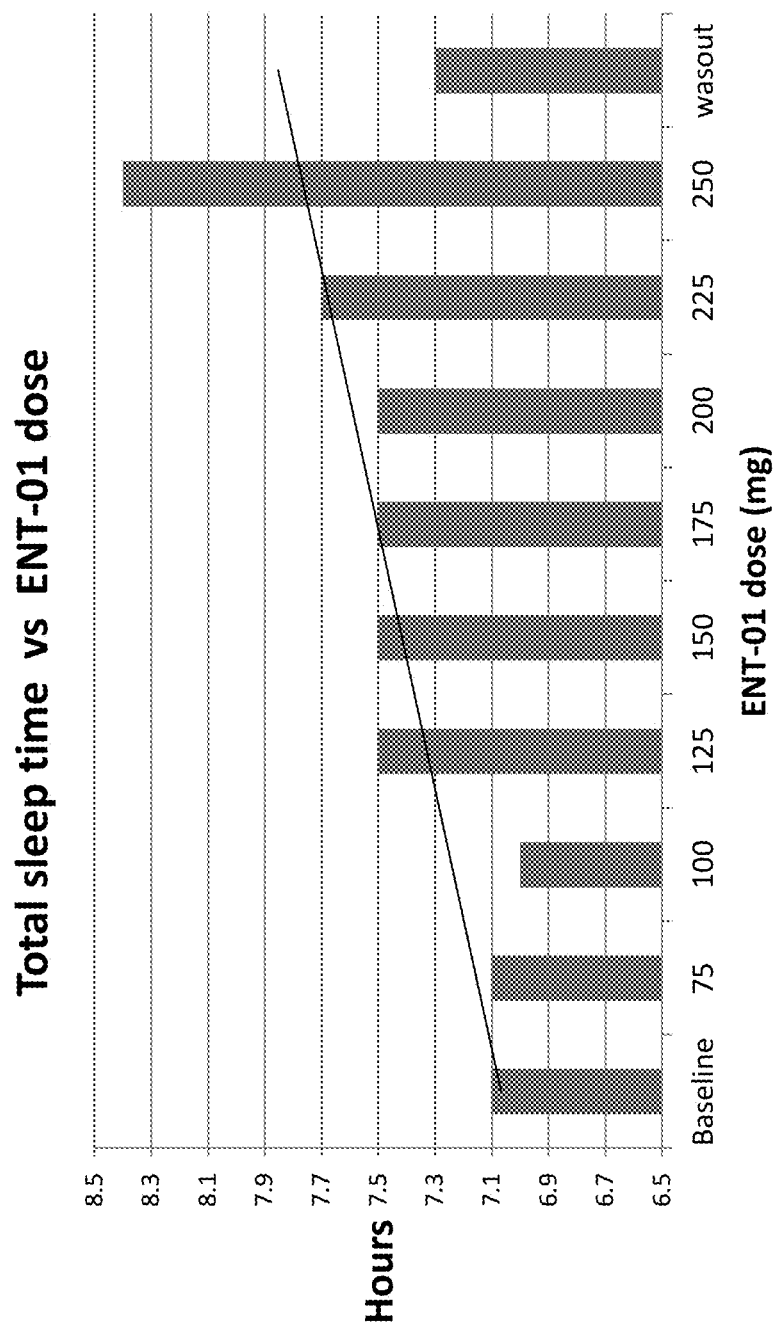
FIG. 5 shows total sleep time vs the dose of squalamine (ENT-01), with total sleep time increasing progressively from baseline to 250 mg.
Figure 6:
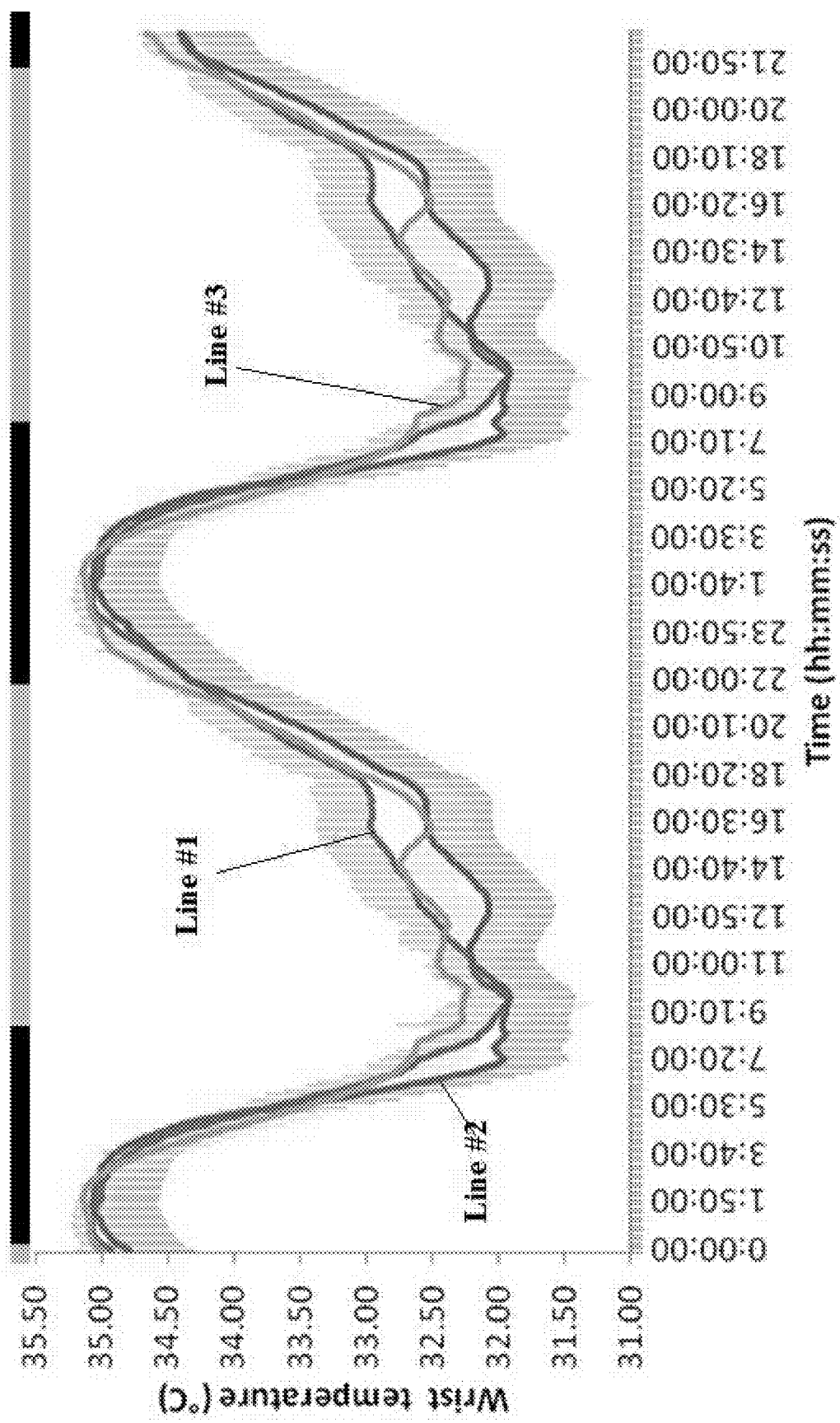
FIG. 6 shows the effect of squalamine (ENT-01) on circadian rhythm. The figure depicts the mean waveform of temperature under three conditions per patient: baseline (Line #1), treatment with highest drug dose (Line #2), and washout (Line #3). Each mean waveform is double plotted for better visualization. Low temperatures indicate higher activation, while higher values are associated with drowsiness and sleepiness. The top black bar indicates a standard rest period from 23:00 to 07:00 h.
Figure 7A:
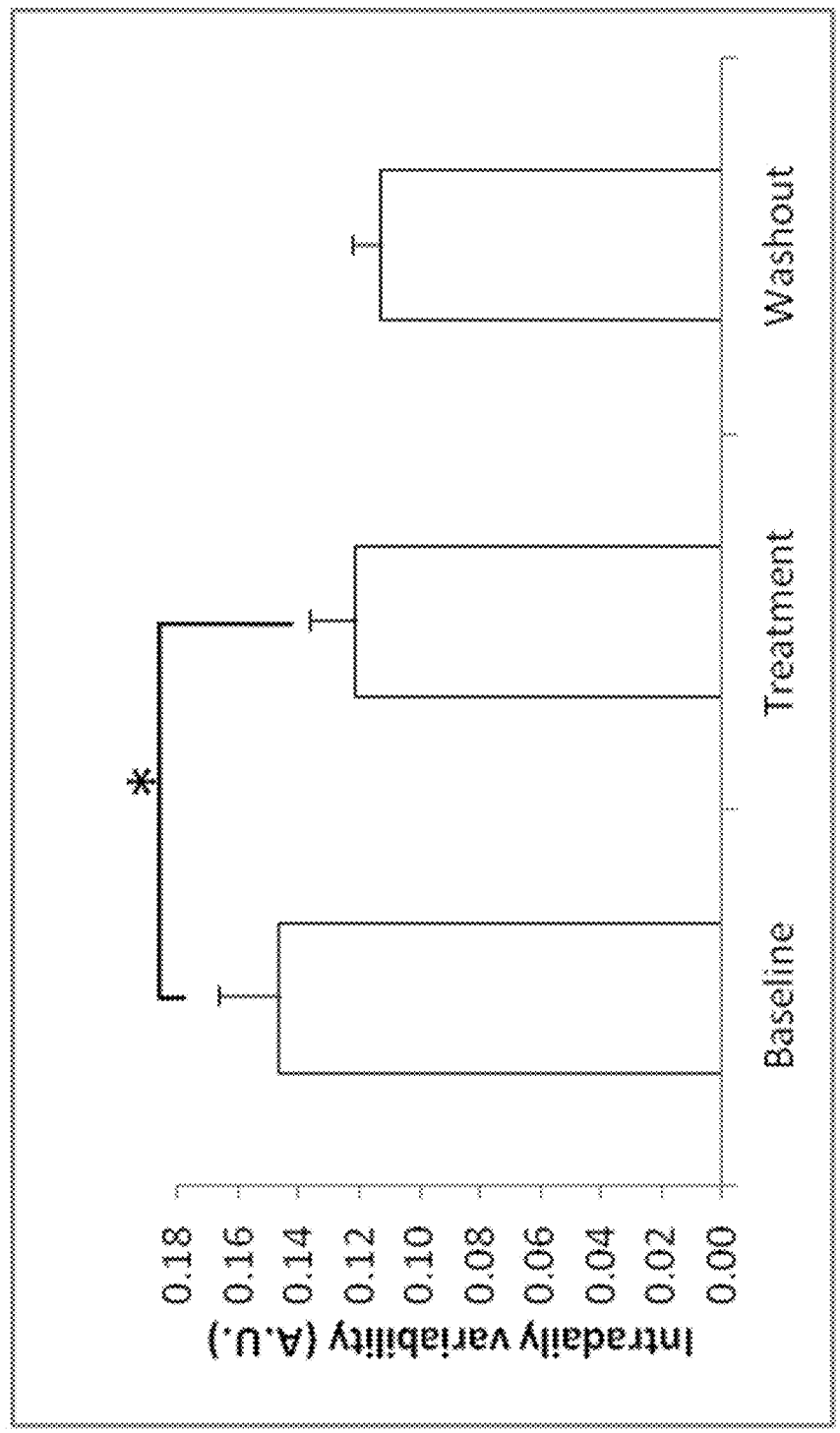
FIGS. 7A-F show the effect of squalamine (ENT-01) on circadian rhythm. The figures depict the results of circadian non-parametric analysis of wrist skin temperature rhythm throughout each condition (baseline, treatment with highest dose of squalamine (ENT-01) and washout). The following parameters were measured: Inter-daily variability (FIG. 7A), inter-daily stability (IS) (FIG. 7B), relative amplitude (RA) (FIG. 7C), circadian function index (FIG. 7D), M5V (FIG. 7E), which refers to the five consecutive hours with the highest temperature or high somnolence, and L10V (FIG. 7F), which indicates the mean of the ten consecutive hours with lowest temperature or high activation. The circadian function index (CFI) is an integrated score that ranges from 0 (absence of circadian rhythm) to 1 (robust circadian rhythm). Student's paired t-test, *p<0.05, p<01, *p<0.001.Values expressed as mean±SEM (n=12 in each condition).
Figure 7B:
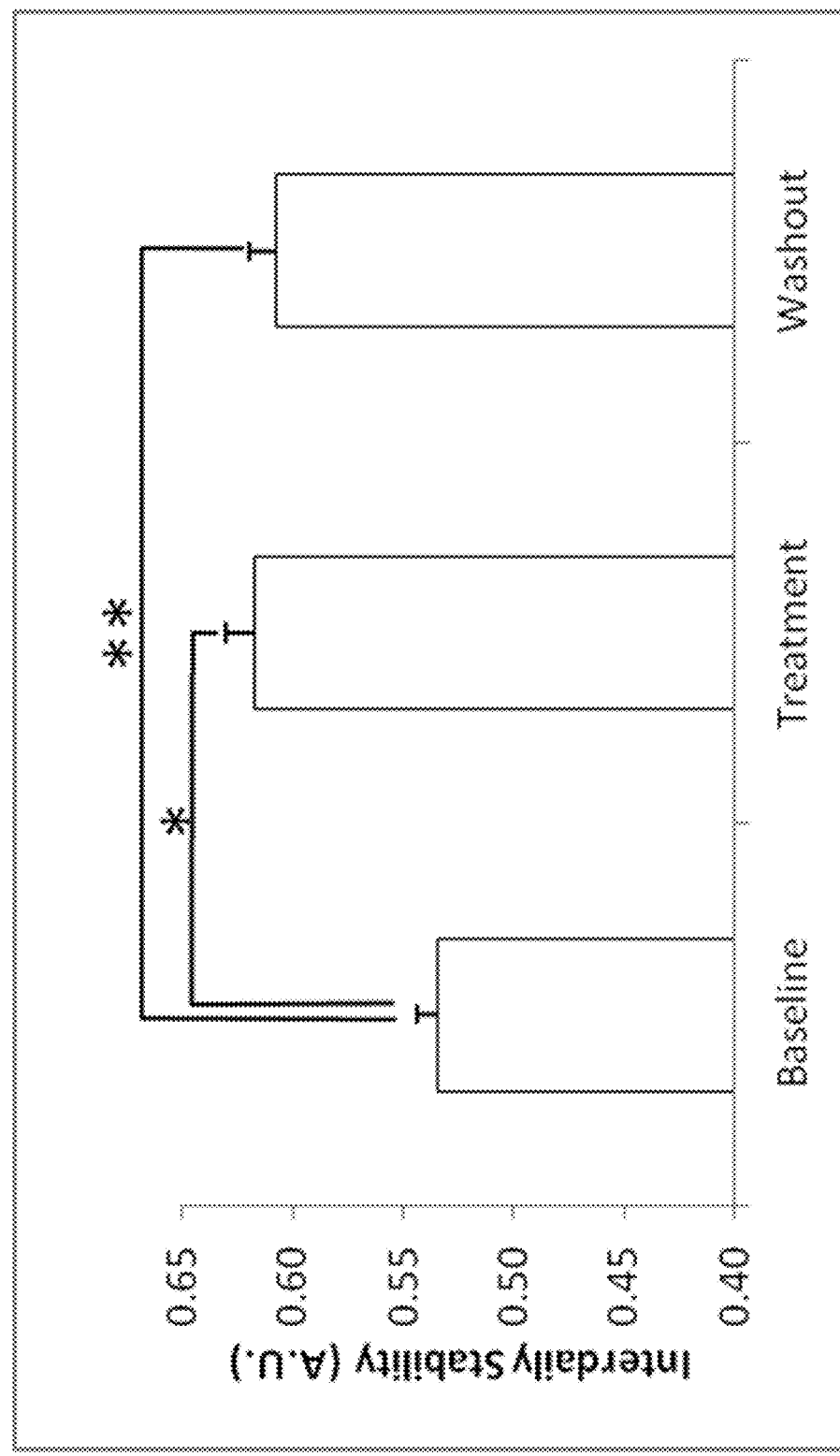
Figure 7C:
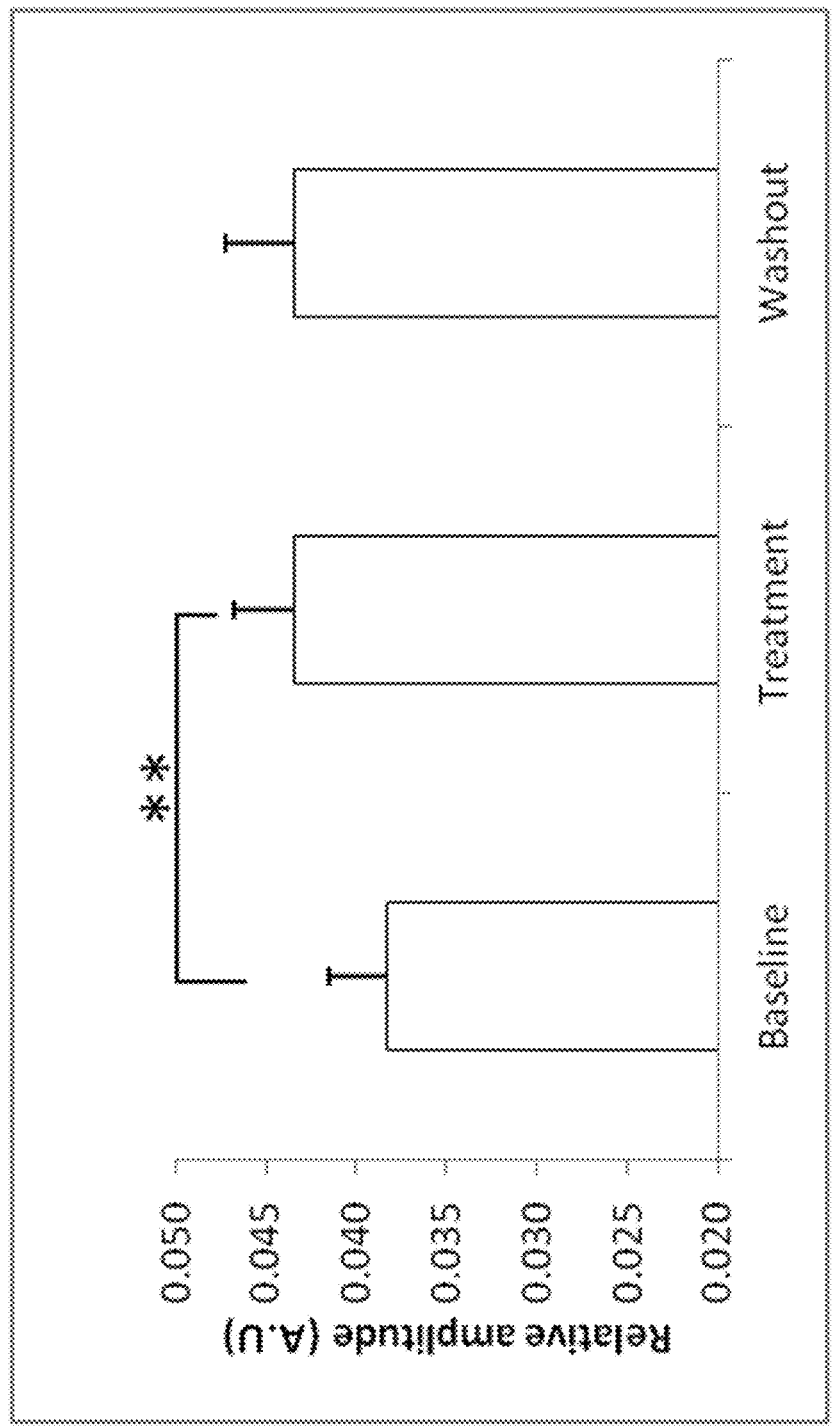
Figure 7D:
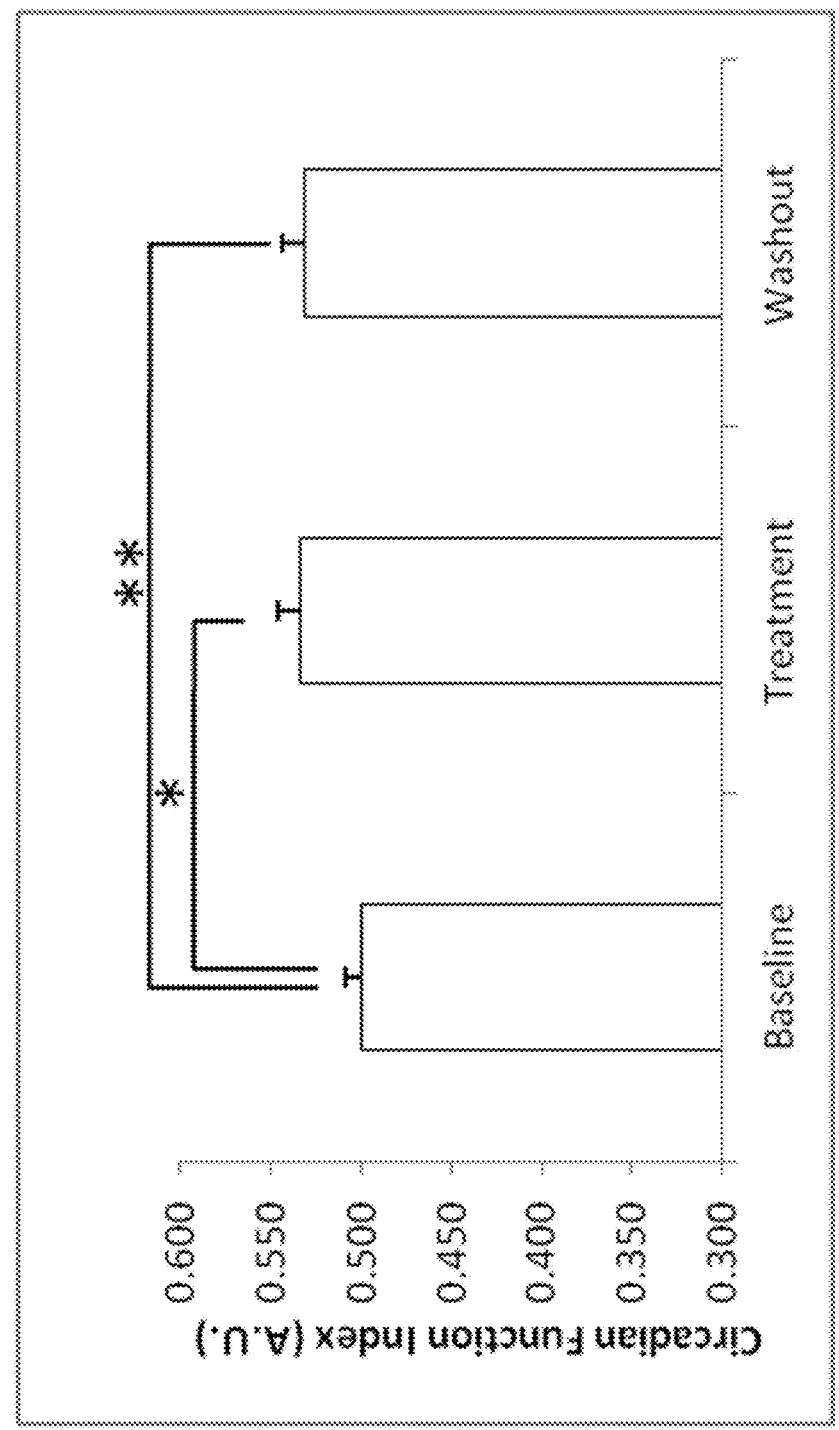
Figure 7E:
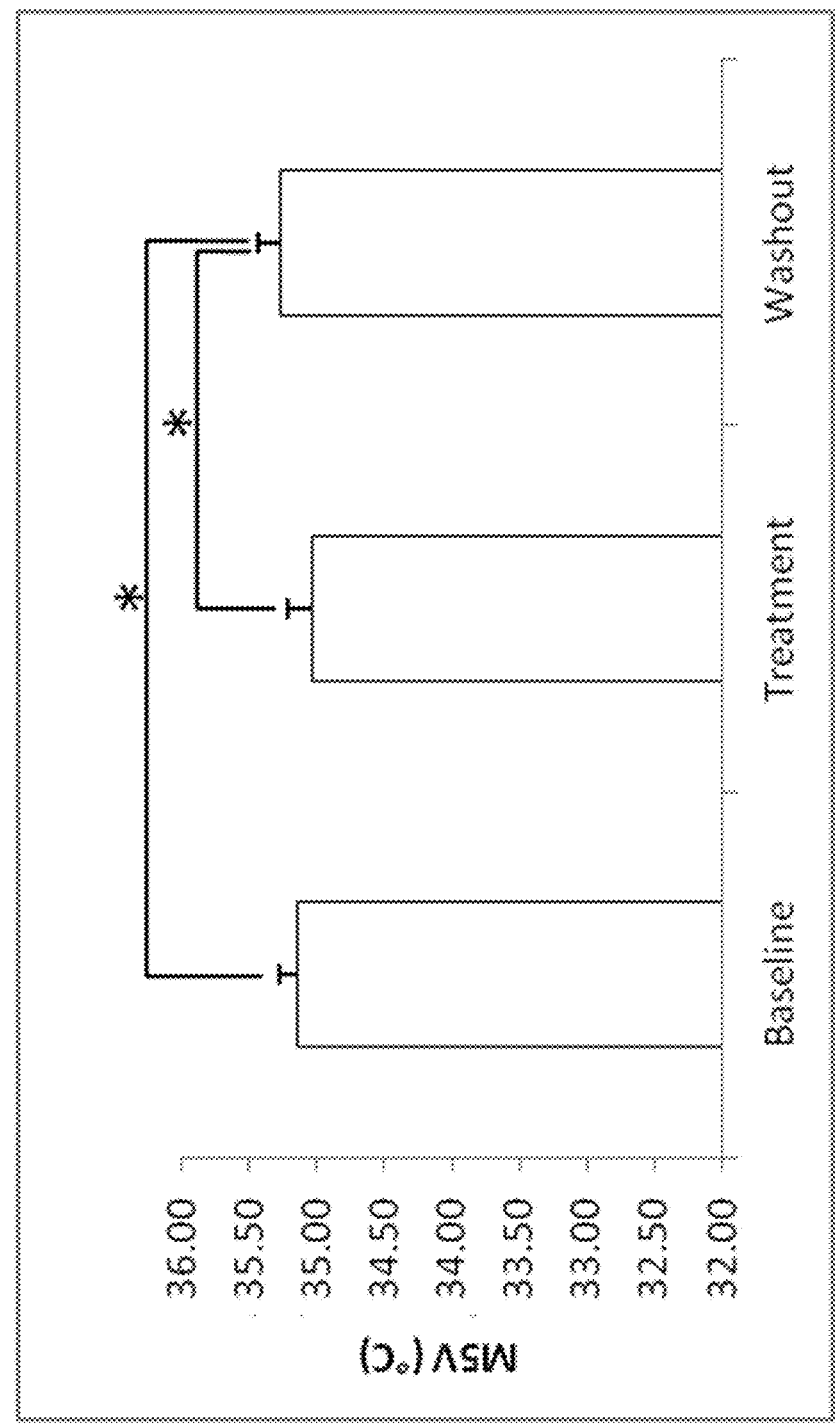
Figure 7F:
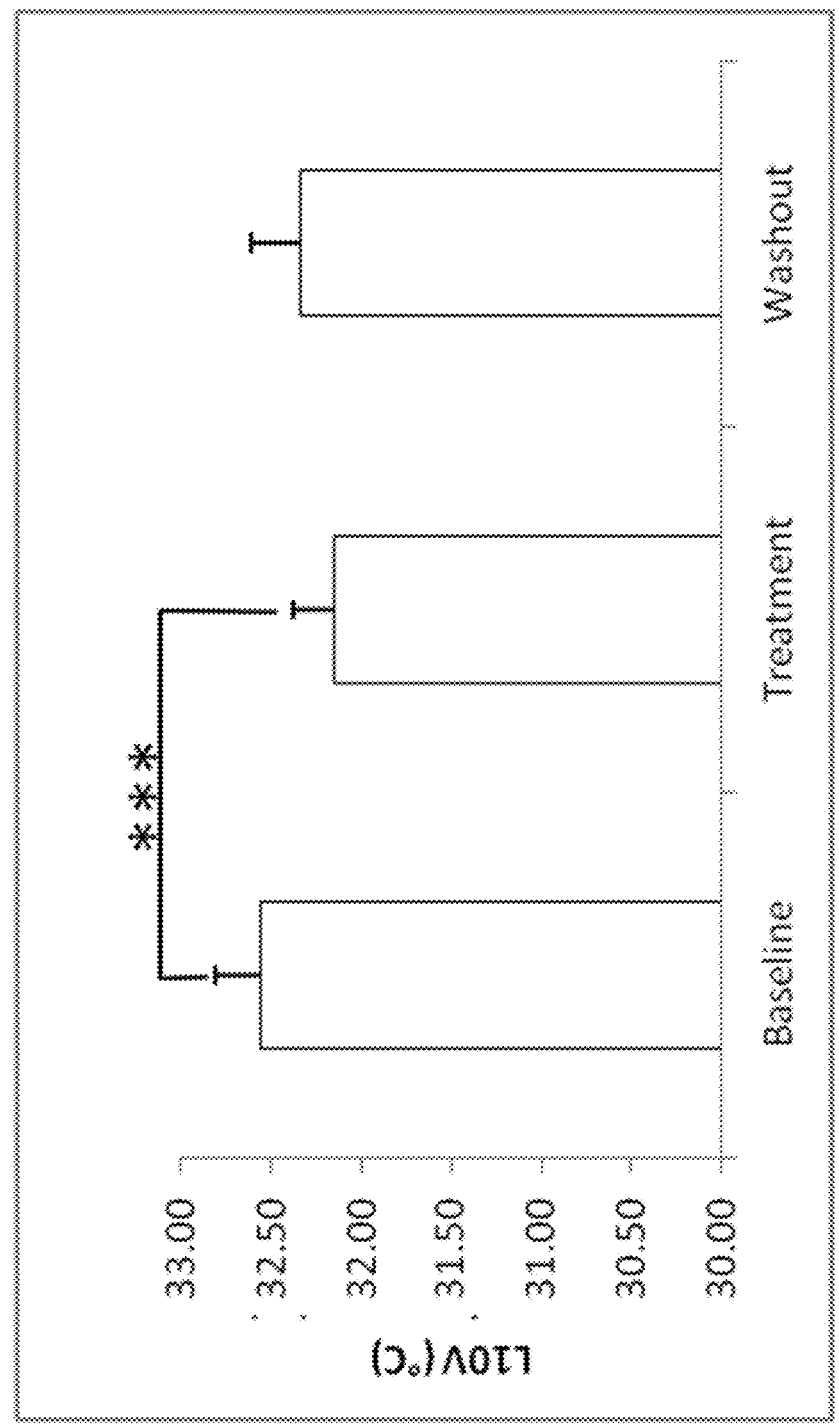
Figure 8:
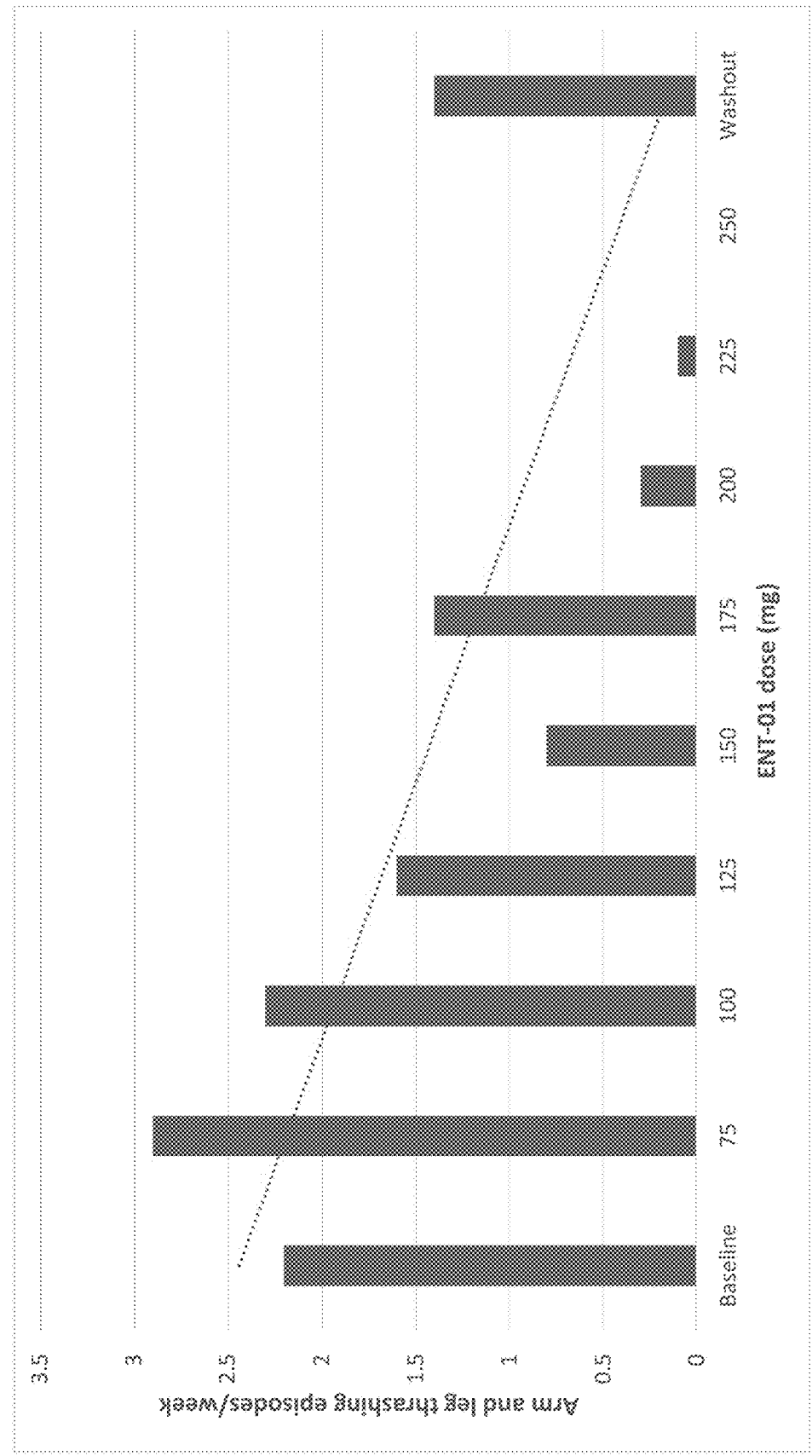
FIG. 8 shows REM-behavior disorder in relation to squalamine (ENT-01) dose, with arm and leg thrashing episodes (mean values) calculated using sleep diaries. The frequency of arm or leg thrashing reported in the sleep diary diminished progressively from 2.2 episodes/week at baseline to 0 at maximal dose.

The data detailed in Example 1 described how circadian system status was evaluated by continuously monitoring wrist skin temperature (Thermochron iButton DS1921H; Maxim, Dallas) following published procedures (Sarabia et al. 2008). Further, an analysis was done with respect to the sleep data, the body temperature data, and fatigue data. The frequency of arm or leg thrashing reported in the sleep diary diminished progressively from 2.2 episodes/week at baseline to 0 at maximal dose (100% improvement). Total sleep time increased progressively from 7.1 hours at baseline to 8.4 hours at 250 mg (an 18% increase) and was consistently higher than baseline beyond 125 mg (FIGS. 3, 4 and 5). FIG. 8 shows REM-behavior disorder in relation to squalamine (ENT-01) dose, with arm and leg thrashing episodes (mean values) calculated using sleep diaries. The frequency of arm or leg thrashing reported in the sleep diary diminished progressively from 2.2 episodes/week at baseline to 0 at maximal dose. Unlike stool-related indices, the improvement in many CNS symptoms persisted during wash-out.

Circadian rhythm of skin temperature was evaluable in 12 patients (i.e., those who had recordings that extended from baseline through washout). Circadian system functionality was evaluated by continuously monitoring wrist skin temperature using a temperature sensor (Thermochron iButton DS1921H; Maxim, Dallas, Tex.) (Sarabia et al. 2008). Briefly, this analysis includes the following parameters: (i) the inter-daily stability (the constancy of 24-hour rhythmic pattern over days, IS); (ii) intra-daily variability (rhythm fragmentation, IV); (iii) average of 10-minute intervals for the 10 hours with the minimum temperature (L10); (iv) average of 10-minute intervals for the 5 hours with the maximum temperature (M5) and the relative amplitude (RA), which was determined by the difference between M5 and L10, divided by the sum of both. Finally, the Circadian Function Index (CFI) was calculated by integrating IS, IV, and RA. Consequently, CFI is a global measure that oscillates between 0 for the absence of circadian rhythmicity and 1 for a robust circadian rhythm.

A comparison was performed of circadian rhythm parameters during the baseline, fixed dose and washout periods. Aminosterol administration improved all markers of healthy circadian function, including increasing rhythm stability, relative amplitude, and circadian function index, while reducing rhythm fragmentation. The improvement persisted for several of these circadian parameters during the washout period. (FIG. 7). Improvements were also seen in REM-behavior disorder (RBD) and sleep. RBD and total sleep time also improved progressively in a dose-dependent manner.

4. Cognitive Impairment

Another symptom associated with SZ is cognitive impairment. Cognitive impairment, including mild cognitive impairment (MCI), is characterized by increased memory or thinking problems exhibited by a subject as compared to a normal subject of the same age. In 2002, an estimated 5.4 million people (22.%) in the United States over age 70 had cognitive impairment without dementia. Plassman et al. 2009.

Cognitive impairment may entail memory problems including a slight but noticeable and measurable decline in cognitive abilities, including memory and thinking skills. When MCI primarily affects memory, it is known as "amnestic MCI." A person with amnestic MCI may forget information that would previously have been easily recalled, such as appointments, conversations, or recent events, for example. When MCI primarily affects thinking skills other than memory, it is known as "nonamnestic MCI." A person with nonamnestic MCI may have a reduced ability to make sound decisions, judge the time or sequence of steps needed to complete a complex task, or with visual perception, for example.

Mild cognitive impairment is a clinical diagnosis. A combination of cognitive testing and information from a person in frequent contact with the subject is used to fully assess cognitive impairment. A medical workup includes one or more of an assessment by a physician of a subject's medical history (including current symptoms, previous illnesses, and family history), assessment of independent function and daily activities, assessment of mental status using brief tests to evaluate memory, planning, judgment, ability to understand visual information, and other key thinking skills, neurological examination to assess nerve and reflex function, movement, coordination, balance, and senses, evaluation of mood, brain imaging, or neuropsychological testing. Diagnostic guidelines for MCI have been developed by various groups, including the Alzheimer's Association partnered with the National Institute on Aging (NIA), an agency of the U.S. National Institutes of Health (NIH). Jack et al. 2011; McKhann et al. 2011; Albert et al. 2011. Recommendations for screening for cognitive impairment have been issued by the U.S. Preventive Services Task Force. *Screening for Cognitive Impairment in Older Adults*, U.S. Preventive Services Task Force (March 2014). For example, the Mini Mental State Examination (MMSE) may be used. Palsetia et al. (2018); Kirkevold, O. & Selbaek, G. (2015). With the MMSE, a score of 24 or greater (out of 30) may indicate normal cognition, with lower scores indicating severe (less than or equal to 9 points), moderate (10-18 points), or mild (19-23 points) cognitive impairment. Other screening tools include the Informant Questionnaire on Cognitive Decline in the Elderly (IQCODE), in which an average score of 3 indicates no cognitive decline and a score greater than 3 indicates some decline. Jorm, A. F. 2004. Alternatively, the 7-Minute Screener, Abbreviated Mental Test Score (AMTS), Cambridge Cognitive Examination (CAMCOG), Clock Drawing Test (CDT), General Practitioner Assessment of Cognition (GPCOG), Mini-Cog, Memory Impairment Screen (MIS), Montreal Cognitive Assessment (MoCA), Rowland Universal Dementia Assessment (RUDA), Self-Administered Gerocognitive Examination (SAGE), Short and Sweet Screening Instrument (SAS-SI), Short Blessed Test (SBT), St. Louis Mental Status (SLUMS), Short Portable Mental Status Questionnaire (SPMSQ), Short Test of Mental Status (STMS), or Time and Change Test (T&C), among others, are frequently employed in clinical and research settings. Cordell et al. 2013. Numerous examinations may be used, as no single tool is recognized as the "gold standard," and improvements in score on any standardized examination indicate successful treatment of cognitive impairment, whereas obtaining a score comparable to the non-impaired population indicates total recovery.

In some embodiments, administration of a therapeutically effective fixed dose of an aminosterol composition to a SZ patient in need results in improvement of cognitive impairment as determined by a clinically recognized assessment scale, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

As detailed in Example 1, cognitive impairment and the improvement following aminosterol treatment were assessed using several tools:

(1) Mini Mental State Examination (MMSE);
(2) Trail Making Test (TMT) Parts A and B; and
(3) Unified Parkinson's Disease Rating Scale (UPDRS), sections 1.1 (cognitive impairment).

Assessments were made at baseline and at the end of the fixed dose and washout periods for Example 1, and an analysis was done with respect to the cognition symptoms. The results showed that the total UPDRS score was 64.4 at baseline, 60.6 at the end of the fixed dose period and 55.7 at the end of the wash-out period (a 13.5% improvement). Part 1 of the UPDRS (which includes section 1.1, cognitive impairment) had a mean baseline score of 11.6, a fixed aminosterol dose mean score of 10.6, and a wash-out mean score of 9.5, demonstrating an almost 20% improvement (UPDRS cognitive impairment is rated from 1=slight improvement to 4=severe impairment, so lower scores correlate with better cognitive function). In addition, MMSE improved from 28.4 at baseline to 28.7 during treatment and to 29.3 during wash-out (the MMSE has a total possible score of 30, with higher scores correlating with better cognitive function). Unlike stool-related indices, the improvement in many CNS symptoms persisted during wash-out.

5. Depression

Another symptom associated with SZ is depression. Clinical depression is characterized by a sad, blue mood that goes above and beyond normal sadness or grief. Major depression is an episode of sadness or apathy along with other symptoms that lasts at least two consecutive weeks and is severe enough to interrupt daily activities. Depressive events feature not only negative thoughts, moods, and behaviors but also specific changes in bodily functions (like, eating, sleeping, energy and sexual activity, as well as potentially developing aches or pains). One in 10 people will have a depression in their lifetime. Doctors clinically diagnose depression; there is no laboratory test or X-ray for depression.

Increasingly sophisticated forms of brain imaging, such as positron emission tomography (PET), single-photon emission computed tomography (SPECT), and functional magnetic resonance imaging (fMRI), permit a much closer look at the working brain than was possible in the past. An fMRI scan, for example, can track changes that take place when a region of the brain responds during various tasks. A PET or SPECT scan can map the brain by measuring the distribution and density of neurotransmitter receptors in certain areas. Use of this technology has led to a better understanding of which brain regions regulate mood and how other functions, such as memory, may be affected by depression. Areas that play a significant role in depression are the amygdala, the thalamus, and the hippocampus.

Research shows that the hippocampus is smaller in some depressed people. For example, in one fMRI study published in *The Journal of Neuroscience*, investigators studied 24 women who had a history of depression. On average, the hippocampus was 9% to 13% smaller in depressed women as compared with those who were not depressed. The more bouts of depression a woman had, the smaller the hippocampus. Stress, which plays a role in depression, may be a key factor, since experts believe stress can suppress the production of new neurons (nerve cells) in the hippocampus.

Researchers are exploring possible links between sluggish production of new neurons in the hippocampus and low moods. An interesting fact about antidepressants supports this theory. These medications immediately boost the concentration of chemical messengers in the brain (neurotransmitters). Yet people typically don't begin to feel better for several weeks or longer. Experts have long wondered why, if depression were primarily the result of low levels of neurotransmitters, people don't feel better as soon as levels of neurotransmitters increase. The answer may be that mood only improves as nerves grow and form new connections, a process that takes weeks. In fact, animal studies have shown that antidepressants do spur the growth and enhanced branching of nerve cells in the hippocampus. So, the theory holds, the real value of these medications may be in generating new neurons (a process called neurogenesis), strengthening nerve cell connections, and improving the exchange of information between nerve circuits.

Thus, in one embodiment of the invention, encompassed are methods of treating, preventing, and/or slowing the onset or progression of depression in SZ subjects comprising administering therapeutically effective fixed dose of an aminosterol composition according to the invention. In some embodiments, the depression is associated with schizophrenia. While not wishing to be bound by theory, it is theorized that the aminosterol compositions of the invention trigger neurogenesis, which functions to combat depression.

In some embodiments, the methods of the invention produce an improvement in a SZ subject's clinical depression. An improvement in a subject's depression can be measured using any clinically-recognized measurement. For example, improvement can be measured using a depression rating scale. In one embodiment of the invention, following treatment a subject experiences an about 5, about 10, about 15, about 20, about 25, about 30, about 35, about 40, about 45, about 50, about 55, about 60, about 65, about 70, about 75, about 80, about 85, about 90, about 95 or an about 100% improvement. The improvement can be measured using any clinically recognized tool or assessment.

As detailed in Example 1, depression and/or mood and the improvement following aminosterol treatment were assessed using several tools:

(1) Beck Depression Inventory (BDI-II);
(2) Unified Parkinson's Disease Rating Scale (UPDRS), sections 1.3 (depressed mood), 1.4 (anxious mood), 1.5 (apathy), and 1.13 (fatigue); and
(3) Parkinson's Disease Fatigue Scale (PFS-16).

Assessments were made at baseline and at the end of the fixed dose and washout periods. An analysis was done with respect to depression and mood scores. Total UPDRS score was 64.4 at baseline, 60.6 at the end of the fixed dose period and 55.7 at the end of the wash-out period, demonstrating a 13.5% improvement, and Part 1 of the UPDRS (which includes mood and depression scores) went from a mean score of 11.6 at baseline, to a mean of 10.6 during the fixed aminosterol dose period, with a mean score of 9.5 during the washout period, demonstrating an improvement of 18%. In addition, BDI-II scores decreased from 10.9 at baseline to 9.9 during treatment and 8.7 at wash-out, showing an improvement in depression scoring of 20%. Unlike stool-related indices, the improvement in many CNS symptoms persisted during wash-out.

6. Neurodegeneration

Schizophrenia may arise due to neurodegeneration (Rund 2009). Patients often display a deteriorating progression with SZ rather than static levels of disease. Early treatment with antipsychotic medications may arrest this progression. A longer duration of untreated psychosis predicts a poorer outcome, suggesting that there are possible adverse neurotoxic effects of untreated psychosis. Long duration of untreated psychosis predicted worse response to medications, higher relapse risk, and mixed association with other outcome measures. This indicates that a pathological process is occurring in the brain, against which drugs played a protective role. It is also seen that patients appear to take longer to recover and show less complete recovery over successive episodes of this illness. Longitudinal neuroimaging studies using techniques like MRI have been done. Longitudinal studies show changes that occur in the brain after the illness has begun, thereby representing the effect of the schizophrenia on the brain (Gupta et al., 2010).

Excess glutamate leading to apoptosis, followed by calcium release and oxidative damage has been seen in schizophrenia. NMDA receptor hypofunction is a theory proposed on the basis of the observation that antagonism of NMDA receptors with drugs like ketamine causes psychotic symptoms (Olney et al., 1995). GABA interneuron-mediated inhibition of pyramidal neurons has also been seen to be reduced (Benes et al., 1991).

Levels of antioxidant enzymes such as superoxide dismutase (SOD), reduced glutathione (GSH), and catalase, and nonenzymatic antioxidants such as ascorbate, albumin, and selenium have been found to be reduced in schizophrenia. Positive symptoms of schizophrenia correlate inversely with levels of superoxide dismutase whereas negative symptoms correlate inversely with levels of reduced glutathione. Haloperidol treatment led to an increase in SOD activity. Oxidative stress is a prominent finding in any type of degenerative process and hence, these changes support a degenerative hypothesis (Gupta et al., 2010).

In some embodiments of the present method, the SZ symptom to be evaluated is neurodegeneration correlated with SZ, and wherein: (a) treating the neurodegeneration prevents and/or delays the onset and/or progression of the SZ; (b) the method results in treating, preventing, and/or delaying the progression and/or onset of neurodegeneration in the subject; (c) progression or onset of the neurodegeneration is slowed, halted, or reversed over a defined period of time following administration of the fixed escalated dose of the aminosterol or a salt or derivative thereof, as measured by a medically-recognized technique; and/or (d) the neurodegeneration is positively impacted by the fixed escalated dose of the aminosterol or a salt or derivative thereof, as measured by a medically-recognized technique.

In some embodiments, (a) the positive impact and/or progression of neurodegeneration is measured quantitatively or qualitatively by one or more techniques selected from the group consisting of electroencephalogram (EEG), neuroimaging, functional MRI, structural MRI, diffusion tensor imaging (DTI), [18F]fluorodeoxyglucose (FDG) PET, agents that label amyloid, [18F]F-dopa PET, radiotracer imaging, volumetric analysis of regional tissue loss, specific imaging markers of abnormal protein deposition, multimodal imaging, and biomarker analysis; and/or (b) the progression or onset of neurodegeneration is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique.

V. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein the term "aminosterol" refers to an amino derivative of a sterol. Non-limiting examples of suitable aminosterols for use in the composition and methods disclosed herein are Aminosterol 1436, squalamine, aminosterols isolated from *Squalus acanthias*, and isomers, salts, and derivatives each thereof.

The term "administering" as used herein includes prescribing for administration as well as actually administering, and includes physically administering by the subject being treated or by another.

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

As used herein, the phrase "therapeutically effective" or "effective" in context of a "dose" or "amount" means a dose or amount that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

The terms "treatment," "treating," or any variation thereof includes reducing, ameliorating, or eliminating (i) one or more specified symptoms and/or (ii) one or more symptoms or effects of a specified disorder. The terms "prevention," "preventing," or any variation thereof includes reducing, ameliorating, or eliminating the risk of developing (i) one or more specified symptoms and/or (ii) one or more symptoms or effects of a specified disorder

EXAMPLES

Example 1

This example describes an exemplary method of treating and/or preventing symptoms of Parkinson's disease (PD) in a clinical trial setting. The methods used in Example 1 to determine the dose of aminosterol may be used to determine the aminosterol dose in subsequent examples relating to schizophrenia or symptoms of schizophrenia.

Overview: The subjects of the trial all had PD and experienced constipation, which is a characteristic of PD. The primary objectives of the trial involving patients with PD and constipation were to evaluate the safety and pharmacokinetics of oral squalamine (ENT-01) and to identify the dose required to improve bowel function, which was used as a clinical endpoint.

Several non-constipation PD symptoms were also assessed as endpoints, including, for example, (1) sleep problems, including daytime sleepiness; (2) non-motor symptoms, such as (i) depression (including apathy, anxious mood, as well as depression), (ii) cognitive impairment (e.g., using trail making test and the UPDRS), (iii) hallucinations (e.g., using The University of Miami Parkinson's Disease Hallucinations Questionnaire (UM-PDHQ) and the UPDRS, (iv) dopamine dysregulation syndrome (UPDRS), (v) pain and other sensations, (vi) urinary problems, (vii) light headedness on standing, and (viii) fatigue (e.g., using Parkinson's Disease Fatigue Scale 9PFS-1t and the UPDRS); (3) motor aspects of experiences of daily living, such as (i) speech, (ii) saliva and drooling, (iii) chewing and swallowing, (iv) eating tasks, (v) dressing, (vi) hygiene, (vii) handwriting; (viii) doing hobbies and other activities, (ix) turning in bed, (x) tremor, (xi) getting out of bed, a car, or a deep chair, (xii) walking and balance, (xiii) freezing; (4) motor examination, such as (i) speech, (ii) facial expression, (iii) rigidity, (ix) finger tapping, (v) hand movements, (vi) pronation-supination movements of hands, (vii) toe tapping, (viii) leg agility, arising from chair, (ix) gait, (x) freezing of gait, (xi) postural stability, (xii) posture, (xiii) global spontaneity of movement (body bradykinesia), (xiv) postural tremor of the hands, (xv) kinetic tremor of the hands, (xvi) rest tremor amplitude, (xvii) constancy of rest tremor; (5) motor complications, such as (i) time spent with dyskinesias, (ii) functional impact of dyskinesias, (iii) time spent in the off state, (iv) functional impact of fluctuations, (v) complexity of motor fluctuations, and (vi) painful off-state dystonia.

Active Agent & Dosing:

Squalamine (ENT-01; Enterin, Inc.) was formulated for oral administration in the trial. The active ion of ENT-01, squalamine, an aminosterol originally isolated from the dogfish shark, has been shown to reverse gastrointestinal dysmotility in several mouse models of PD. In addition, ENT-01 has been shown to inhibit the formation of aggregates of αS both in vitro, and in a *C. elegans* model of PD in vivo (Perni et al. 2017). In the *C. elegans* model, squalamine produced a complete reversal of muscle paralysis.

ENT-01 is the phosphate salt of squalamine. For this study it has been formulated as a small 25 mg coated tablet. Dosing ranged from 25 mg to 250 mg, with dosages greater than 25 mg requiring multiple pills (e.g., 50 mg=two 25 mg pills). Dosing instructions=take 60 mins before breakfast with 8 oz. water. The dose was taken by each patient upon awakening on an empty stomach along with 8 oz. of water simultaneously to dopamine. The subject was not allowed to ingest any food for at least 60 minutes after study medication. The compound is highly charged and will adsorb to foodstuffs, so it was administered prior to feeding.

The phosphate salt of squalamine (ENT-01) is weakly soluble in water at neutral pH but readily dissolves at pH<3.5 (the pH of gastric fluid). Squalamine, as the highly water soluble dilactate salt has been extensively studied in over three Phase 1 and eight Phase 2 human clinical trials as an intravenous agent for the treatment of cancer and diabetic retinopathy. The compound is well tolerated in single and repeat intravenous administration, alone or in combination with other agents, to doses of at least 300 mg/m$^2$).

In the current clinical trial, squalamine (ENT-01) was administered orally to subjects with PD who have long standing constipation. Although this trial was the first in man oral dosing study of ENT-01, humans have long been exposed to low doses of squalamine (milligram to microgram) in the various commercial dogfish shark liver extracts available as nutraceuticals (e.g., Squalamax). In addition, following systemic administration squalamine is cleared by the liver and excreted as the intact molecule (in mice) into the duodenum through the biliary tract. Drug related GI toxicology has not been reported in published clinical trials involving systemic administration of squalamine.

Squalamine (ENT-01) has limited bioavailability in rats and dogs. Based on measurement of portal blood concentrations following oral dosing of radioactive ENT-01 to rat's absorption of ENT-01 from the intestine is low. As a consequence, the principal focus of safety is on local effects on the gastrointestinal tract. However, squalamine (ENT-01) appears to be well tolerated in both rats and dogs.

The starting dose in the Stage 1 segment of the trial was 25 mg (0.33 mg/kg for a 75 kg subject). The maximum single dose in Stage 1 was 200 mg (2.7 mg/kg for a 75 kg subject). The maximum dose evaluated in Stage 2 of the trial was 250 mg/day (3.3 mg/kg/day for a 75 kg subject), and the total daily dosing exposure lasted no longer than 25 days.

The daily dosing range in the clinical trial was from 25 mg (14.7 mg/m$^2$) to 250 mg (147 mg/m$^2$). Oral dosing of squalamine (ENT-01), because of its low oral bioavailability, is not anticipated to reach significant plasma concentrations in human subjects. In preclinical studies, squalamine (ENT-01) exhibited an oral bioavailability of about 0.1% in both rats and dogs. In Stage 1 of this phase 2 study, oral dosing up to 200 mg (114 mg/m$^2$) yielded an approximate oral bioavailability of about 0.1%, based on a comparison of a pharmacokinetic data of the oral dosing and the pharmacokinetic data measured during prior phase 1 studies of IV administration of squalamine.

Study Protocol: The multicenter Phase 2 trial was conducted in two Stages: a dose-escalation toxicity study in Stage 1 and a dose range-seeking and proof of efficacy study in Stage 2.

PD symptoms were assessed using a number of different tools:

(1) Numeric Rating Scales for Pain and Swelling (scale of 0-10, with 0=no pain and 10=worst pain ever experienced);

(2) Rome-IV Criteria for Constipation (7 criteria, with constipation diagnosis requiring two or more of the following: (i) straining during at least 25% of defecations, (ii) lumpy or hard stools in at least 25% of defecations, (iii) sensation of incomplete evacuation for at least 25% of defecations, (iv) sensation of anorectal obstruction/blockage for at least 25% of defecations; (v) manual maneuvers to facilitate at least 25% of defecations; (vi) fewer than 3 defecations per week; and (vii) loose stools are rarely present without the use of laxatives;

(3) Constipation—Ease of Evacuation Scale (from 1-7, with 7=incontinent, 4=normal, and 1=manual disimpaction);

(4) Bristol Stool Chart, which is a patient-friendly means of categorizing stool characteristics (assessment of stool consistency is a validated surrogate of intestinal motility) and Stool Diary;

(5) Sleep Diary (participants completed a sleep diary on a daily basis throughout the study. The diaries included time into bed and estimated time to sleep as well as wake time and duration during the night);

(6) I-Button Temperature Assessment. The I-Button is a small, rugged self-sufficient system that measures temperature and records the results in a protected memory section. The Thermochron I-Button DS1921H (Maxim Integrated, Dallas, Tex.) was used for skin temperature measurement. I-Buttons were programmed to sample every 10 mins., and attached to a double-sided cotton sport wrist band using Velcro, with the sensor face of the I-Button placed over the inside of the wrist, on the radial artery of the dominant hand. Subjects removed and replaced the data logger when necessary (i.e., to have a bath or shower). The value of skin temperature assessment in sleep research is that the endogenous skin warming resulting from increased skin blood flow is functionally linked to sleep propensity. From the collected data, the mesor, amplitude, acrophase (time of peak temperature), Rayleight test (an index of interdaily stability), mean waveforms are calculated);

(7) Non-motor Symptoms Questionnaire (NMSQ);

(8) Beck Depression Inventory (BDI-II);

(9) Unified Parkinson's Disease Rating Scale (UPDRS), which consists of 42 items in four subscales (Part I=Non-Motor Aspects of Experiences of Daily Living (nM-EDL) (1.1 cognitive impairment, 1.2 hallucinations and psychosis, 1.3 depressed mood, Part II=Motor Aspects of Experiences of Daily Living (M-EDL), Part III=Motor Examination, and Part IV=Motor Complications;

(10) Mini Mental State Examination (MMSE);

(11) Trail Making Test (TMT) Parts A and B;

(12) The University of Miami Parkinson's Disease Hallucinations Questionnaire (UM-PDHQ);

(13) Parkinson's Disease Fatigue Scale (PFS-16);

(14) Patient Assessment of Constipation Symptoms (PAC-SYM);

(15) Patient Assessment of Constipation Quality of Life (PAC-QOL);

(16) REM Sleep Behavior Disorder Screening Questionnaire; and

(17) Parkinson's Disease Sleep Scale.

Exploratory end-points, in addition to constipation, included for example, (i) depression assessed using the Beck Depression Inventory (BDI-II) (Steer et al. 2000) and Unified Parkinson's Disease Rating Scale (UPDRS); (ii) cognition assessed using the Mini Mental State Examination (MMSE) (Palsteia et al. 2018), Unified Parkinson's Disease Rating Scale (UPDRS), and Trail Making Test (TMT); (iii) sleep and REM-behavior disorder (RBD) using a daily sleep diary, I-Button Temperature Assessment, a REM sleep behavior disorder (RBD) questionnaire (RBDQ) (Stiasny-Kolster et al. 2007), and the UPDRS; (iv) hallucinations assessed using the PD hallucinations questionnaire (PDHQ) (Papapetropoulos et al. 2008), the UPDRS, and direct questioning; (v) fatigue using the Parkinson's Disease Fatigue Scale (PFS-16) and the UPDRS; (vi) motor functions using the UPDRS; and (vii) non-motor functions using the UPDRS.

Assessments were made at baseline and at the end of the fixed dose and washout periods. Circadian system status was evaluated by continuously monitoring wrist skin temperature (Thermochron iButton DS1921H; Maxim, Dallas) following published procedures (Sarabia et al. 2008).

Based on these data, it is believed that administration of squalamine (ENT-01), a compound that can displace αS from membranes in vitro, reduces the formation of neurotoxic αS aggregates in vivo, and stimulates gastrointestinal motility in patients with PD and constipation. The observation that the dose required to achieve a prokinetic response increases with constipation severity supports the hypothesis that the greater the burden of αS impeding neuronal function, the higher the dose of squalamine (ENT-01) required to restore normal bowel function.

Study Design:

A multicenter Phase 2 trial was conducted in two Stages: a dose-escalation toxicity study in Stage 1 and a dose range-seeking and proof of efficacy study in Stage 2. The protocol was reviewed and approved by the institutional review board for each participating center and patients provided written informed consent.

Following successful screening, all subjects underwent a 14-day run-in period where the degree of constipation was assessed through a validated daily log (Zinsmeister et al. 2013) establishing baseline CSBMs/week. Subjects with an average of <3 CSBMs/week proceeded to dosing.

In Stage 1, ten (10) PD patients received a single escalating dose of squalamine (ENT-01) every 3-7 days beginning at 25 mg and continuing up to 200 mg or the limit of tolerability, followed by 2-weeks of wash-out. Duration of this part of the trial was 22-57 days. The 10 subjects in the sentinel group were assigned to Cohort 1 and participated in 8 single dosing periods. Tolerability limits included diarrhea or vomiting. A given dose was considered efficacious in stimulating bowel function (prokinetic) if the patient had a complete spontaneous bowel movement (CSBM) within 24 hours of dosing.

Each dose period was staggered, so that subjects 1-2 were administered a single dose of the drug at the lowest dose of 25 mg. Once 24 hours have elapsed, and provided there are no safety concerns, the patient was sent home and brought back on day 4-8 for the next dose. During the days the subjects are home, they completed the daily diaries and e-mailed them to the study coordinators. Subjects 3-10 were dosed after the first 2 subjects have been observed for 72 hours, i.e. on Day 4. Subjects 1-2 were also brought back on Day 4-8 and given a single dose of 50 mg. Once another 24 hours have elapsed and provided there are no safety concerns, the patients were all sent home and instructed to return on Day 7 for the next dosing level. This single dosing regimen was continued until each subject was given a single dose of 200 mg or has reached a dose limiting toxicity (DLT). DLT was the dose which induces repeated vomiting, diarrhea, abdominal pain or symptomatic postural hypotension within 24 hours of dosing.

In Stage 2, 34 patients were evaluated. First, 15 new PD patients were administered squalamine (ENT-01) daily, beginning at 75 mg, escalating every 3 days by 25 mg to a dose that had a clear prokinetic effect (CSBM within 24 hours of dosing on at least 2 of 3 days at a given dose), or the maximum dose of 175 mg or the tolerability limit. This dose was then maintained ("fixed dose") for an additional 3-5 days. After the "fixed dose", these patients were randomly assigned to either continued treatment at that dose or to a matching placebo, for an additional 4-6 days prior to a 2-week wash-out.

A second cohort of 19 patients received squalamine (ENT-01) escalating from 100 mg/day to a maximum of 250 mg/day without subsequent randomization to squalamine (ENT-01) or placebo. Criteria for dose selection and efficacy were identical to those used in the previous cohort.

Patient Population:

Patients were between 18 and 86 years of age and diagnosed with PD by a clinician trained in movement disorders following the UK Parkinson's Disease Society Brain Bank criteria (Fahn et al. 1987). Patients were required to have a history of constipation as defined by <3 CSBMs/week and satisfy the Rome IV criteria for functional constipation (Mearin et al. 2016) at screening, which requires 2 or more of the following: Straining during at least 25% of defecations; lumpy or hard stools in at least 25% of defecations; sensation of incomplete evacuation in at least 25% of defecations; sensation of anorectal obstruction/blockage in at least 25% of defecations; and/or manual maneuvers to facilitate at least 25% of defecations.

Baseline characteristics of patients are shown in Table 2. Patients in Stage 2 had somewhat longer duration of Parkinson's disease and higher UPDRS scores than participants in Stage 1.

TABLE 2

Baseline Characteristics of Dosed Patients

| Characteristic | Stage 1** (n = 10) | Stage 2*** (n = 34) | Total (n = 44) |
|---|---|---|---|
| Sex- no. (%) | | | |
| Male | 5 (50) | 25 (73.5) | 30 (68.1) |
| Female | 5 (50) | 9 (26.5) | 14 (31.8) |
| White race-no. (%) | 8 (80) | 34 (100) | 42 (95.54) |
| Age-yr | | | |
| Mean | 65.0 | 74.5 | 72.5 |
| Range | 58-70.5 | 60.6-84.2 | 58-84.2 |
| Age at PD diagnosis-yr | | | |
| Mean | 61.1 | 67.7 | 66.2 |
| Range | 54.2-69 | 50.6-82.5 | 50.6-82.5 |
| Duration of PD-yr | | | |
| Mean | 4.2 | 6.8 | 6.2 |
| Range | 1-11 | 0.3-17.3 | 0.3-17.3 |
| Duration of constipation-yr | | | |
| Mean | 25.8 | 16.8 | 18.9 |
| Range | 1-65 | 0.5-66.0 | 0.5-66.0 |
| UPDRS score | | | |
| Mean | 53.4 | 63.2 | 61.3 |
| Range | 33-88 | 24-122 | 24.0-122.0 |
| Hoehn and Yahr-Stage | | | |
| Mean | 2.0 | 2.4 | 2.3 |
| Range | 2.0 | 1.0-5.0 | 1.0-5.0 |
| Constipation severity*- CSBM/wk- no. (%) | | | |
| 0-1 | 8 (80) | 14 (41.2) | 22 (50) |
| 1.1-2 | 2 (20) | 17 (50) | 19 (43.2) |
| 2.1-3 | 0 | 3 (8.8) | 3 (6.8) |

*At baseline. Baseline value is the average number of CSBMs per week calculated at the end of the 2-week run-in period.
**In Stage 1, 10 patients received single escalating doses every 3-7 days starting at 25 mg and escalating up to dose limiting toxicity (DLT) or 200 mg, whichever came first, followed by a 2-week wash-out period.
***In Stage 2, 15 patients received daily doses starting at 75 mg and escalating every 3 days up to prokinetic dose (dose producing CSBMs on at least 2 of 3 days) or 175 mg, whichever came first, followed by an additional 2-4 days at that dose ("fixed dose" period) and were then randomized to treatment at the "fixed-dose" or placebo for 4-6 days. Wash-out lasted 2 weeks. The remaining 19 patients were escalated from 100 mg to prokinetic dose or 250 mg, whichever came first, followed by an additional 2-4 days at that dose and then a 2-week wash-out period.

Figure 2:
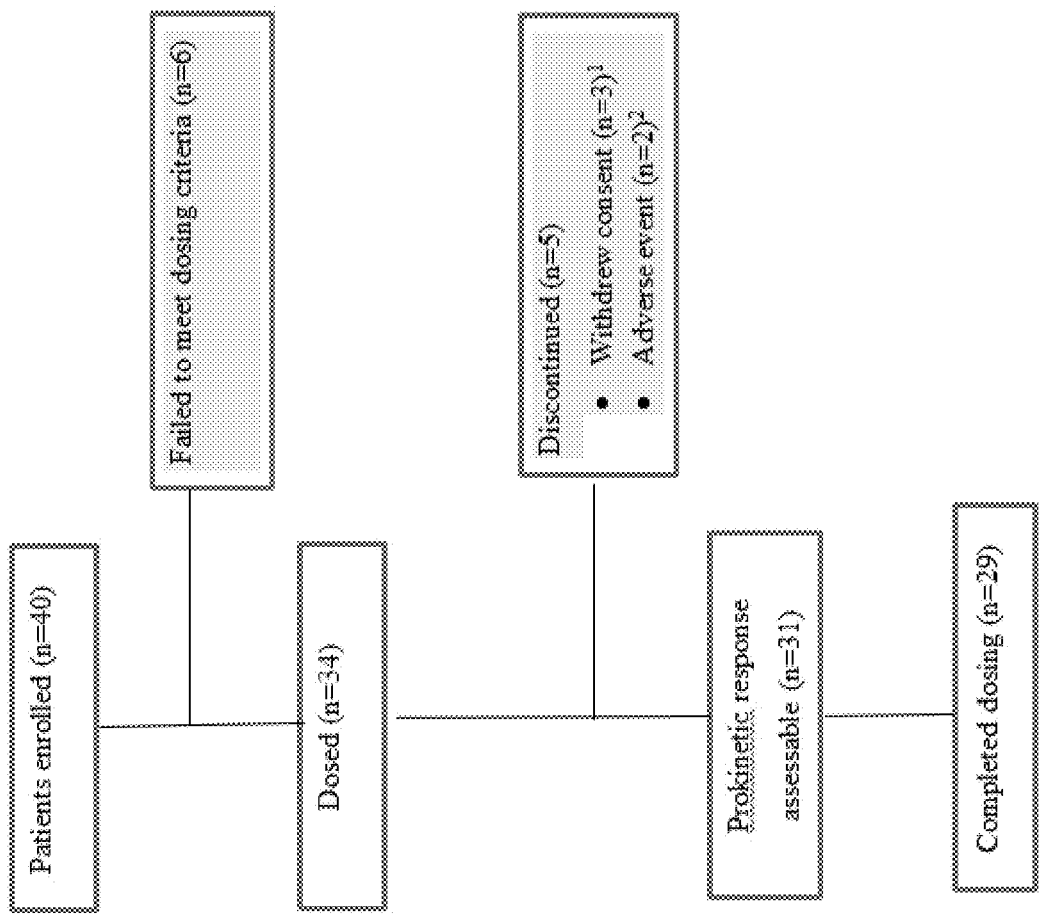
FIG. 2 is a schematic (flowchart) showing patient disposition in Stage 2 of the clinical study. (1) Patients first enrolled (n=40); (2) 6 patients failed to meet dosing criteria and were excluded; (3) 34 patients were dosed; (4) 5 patients were discontinued; 3 patients withdrew consent (with 1 patient lost to follow up and 2 patients withdrew because of diarrhea); and 2 patients discontinued because of an adverse event (recurrent dizziness after medication); (5) 31 patients had an assessable prokinetic response; and (6) 29 patients completed dosing.

Safety and Adverse Event (AE) Profile:

Fifty patients were enrolled and 44 were dosed. In Stage 1, 10 patients were dosed, 1 (10%) withdrew prior to completion and 9 (90%) completed dosing. In stage 2, 6 (15%) patients had ≥3 CSBM/week at the end of the run-in period and were excluded, 34 patients were dosed and bowel response was assessable in 31 (91%). Two patients (5.8%) were terminated prior to completion because of recurrent dizziness, and 3 others withdrew during dosing (8.8%): 2 because of diarrhea and 1 because of holiday. Fifteen patients were randomized. Study-drug assignments and patient disposition are shown in Table 3 and FIG. 2.

TABLE 3

Study drug assignments and adherence to treatment

|  | Stage 1 | Stage 2 |
| --- | --- | --- |
| Enrolled | 10 | 40 |
| Failed prior to dosing | 0 | 6 |
| Dosed | 10 | 34 |
| 25-200 mg | 10 |  |
| 75-175 mg |  | 19 |
| 100-250 mg |  | 15 |
| Terminated (%) | 0 (0) | 2* (5.8) |
| Withdrew (%) | 1 (10) | 3 (8.8) |
| Completed dosing (%) | 9 (90) | 31** (91) |
| Randomized |  | 15 |
| Treatment |  | 6 |
| Placebo |  | 9 |

*The 2 patients who were terminated
**29 patients completed dosing but an additional 2 who withdrew had an assessable prokinetic end-point.

Most AEs were confined to the GI tract (88% in Stage 1 and 63% in Stage 2). The most common AE was nausea which occurred in 4/10 (40%) patients in Stage 1 and in 18/34 (52.9%) in Stage 2 (Table 2). Diarrhea occurred in 4/10 (40%) patients in Stage 1 and 15/34 (44%) in Stage 2. One patient withdrew because of recurrent diarrhea. Other GI related AEs included abdominal pain 11/44 (32%), flatulence 3/44 (6.8%), vomiting 3/44 (6.8%), worsening of acid reflux 2/44 (4.5%), and worsening of hemorrhoids 1/44 (2.2%). One patient had a lower GI bleed (Serious adverse event, SAE) during the withdrawal period. This patient was receiving aspirin, naproxen and clopidogrel at the time of the bleed, and colonoscopy revealed large areas of diverticulosis and polyps. This SAE was considered unrelated to study medication. The only other noteworthy AE was dizziness 8/44 (18%). Dizziness was graded as moderate in one patient who was receiving an alpha-adrenergic blocking agent (Terazosin). This patient was withdrawn from the study and recovered spontaneously. All other AEs resolved spontaneously without discontinuation of squalamine (ENT-01). The relationship between dose and AEs is shown in Table 4.

TABLE 4

All adverse events (n, %)

|  | Stage 1 (n = 10) | Stage 2 (n = 40) |
| --- | --- | --- |
| Enrolled |  |  |
| Dosed | 10 | 34 |
| GI: Nausea | | |
| Mild | 4 (40) | 18 (52) |
| Moderate | 0 | 1 (2.9) |
| Diarrhea | | |
| Mild | 1 (10) | 12 (35) |
| Moderate | 3 (30) | 2 (5.8) |
| Severe | 0 | 1 (2.9) |
| Vomiting | | |
| Mild | 1 (10) | 2 (5.8) |
| Moderate | 0 | 0 |
| Abdominal pain | | |
| Mild | 2 (20) | 4 (11.7) |
| Moderate | 3 (30) | 2 (5.8) |
| Flatulence | | |
| Mild | 2 (20) | 1 (3) |
| Moderate | 0 | 0 |
| Loss of appetite* | | |
| Mild | 1 (10) | 0 |
| Moderate | 0 | 0 |
| Worsening acid reflux | | |
| Mild | 0 | 4 (11.7) |
| Moderate | 0 | 0 |
| Worsening hemorrhoid | | |
| Mild | 0 | 1 (3) |
| Moderate | 0 | 0 |
| Lower GI bleed** | | |
| Severe | 0 | 1 (2.5) |
| Non-GI: Dizziness | | |
| Mild | 0 | 7 (20.5) |
| Moderate | 0 | 1 (2.9) |
| Blood in urine* | | |
| Mild | 1 (10) | 0 |
| Moderate | 0 | 0 |
| Headache | | |
| Mild | 1 (10) | 3 (8.8) |
| Moderate | 0 | 0 |
| Urinary retention | | |
| Mild | 0 | 1 (3) |
| Moderate | 0 | 0 |
| Urinary tract infection | | |
| Mild | 0 | 1 (3) |
| Moderate | 0 | 2 (5.8) |
| Increased urinary frequency | | |
| Mild | 0 | 2 (5.8) |
| Moderate | 0 | 0 |
| Skin lesions-rash | | |
| Mild | 0 | 3 (8.8) |
| Moderate | 0 | 0 |
| Eye infection | | |
| Mild | 0 | 1 (3) |
| Moderate | 0 | 0 |
| Difficulty falling asleep | | |
| Mild | 0 | 1 (3) |
| Moderate | 0 | 0 |

*Unrelated to ENT-01
**colonic diverticulosis, polyp, patient on aspirin, Plavix and naproxen. Unrelated to ENT-01

TABLE 5

Common adverse events by dose

| Dose (mg) | Stage 1 | | | Stage 2 | | |
|---|---|---|---|---|---|---|
| | Diarrhea | Nausea | Vomiting | Diarrhea | Nausea | Dizziness* |
| 0 | 0 | 0 | 0 | 1 | 0 | 2 |
| 25 | 1 | 0 | 0 | — | — | — |
| 50 | 1 | 0 | 0 | — | — | — |
| 75 | 1 | 0 | 0 | 7 | 3 | 8 |
| 100 | 0 | 1 | 1 | 10 | 12 | 7 |
| 125 | 1 | 2 | 1 | 3 | 4 | 8 |
| 150 | 1 | 0 | 0 | 2 | 11 | 2 |
| 175 | 1 | 1 | 0 | 1 | 12 | 0 |
| 200 | 0 | 2 | 0 | 3 | 6 | — |
| 225 | — | — | — | 3 | 1 | |
| 250 | — | — | — | 2 | — | |

*lightheadedness included

TABLE 6

Dose limiting toxicity criteria

| | |
|---|---|
| Diarrhea | Increase 4-6 stools/day over baseline |
| Vomiting | 3-5 episodes in 24 hours |
| Abdominal pain | Moderate pain limiting daily activities |
| Postural hypotension | Moderately symptomatic and limiting daily activities or BP < 80/40 |

No formal sample size calculation was performed for Stage 1. The number of subjects (n=10) was based on feasibility and was considered sufficient to meet the objectives of the study; which was to determine the tolerability of the treatment across the range of tested doses. For Stage 2, assuming the highest proportion of spontaneous resolution of constipation with no treatment to be 0.10, 34 evaluable subjects who have measurements at both baseline and at the end of the fixed dose period provided 80% power to detect the difference between 0.10 (proportion expected if patients are not treated) and a squalamine (ENT-01) treated proportion of 0.29.

No randomization was performed for Stage 1. During the randomization period of Stage 2, subjects were randomly allocated in equal proportion (1:1) to 1 of 2 double-blind treatment groups in a block size of 4: (1) squalamine (ENT-01) at the identified fixed dose level, or (2) placebo at the identified fixed dose level.

Adverse events were coded using the current version of MedDRA. Severity of AEs were assessed by investigators according to CTCAE (v4.03): Grade 1 is labeled as Mild, Grade 2 as Moderate, and Grade 3 and above as Severe. AEs that have a possible, probable or definite relationship to study drug were defined to be related to the study drug while others were defined as "not related". The number (percentage) of subjects who experienced an AE during escalation and fixed dosing periods were summarized by dose level and overall for each stage. The denominator for calculating the percentages were based on the number of subjects ever exposed to each dose and overall.

Effect on Bowel Function:

Cumulative responder rates of bowel function are shown in FIG. 1A. In Stage 1 (single dose), cumulative response rate increased in a dose-dependent fashion from 25% at 25 mg to a maximum of 80% at 200 mg.

In Stage 2 (daily dosing), the response rate increased in a dose-dependent fashion from 26% at 75 mg to 85.3% at 250 mg. The dose required for a bowel response was patient-specific and varied from 75 mg to 250 mg. Median efficacious dose was 100 mg. Average CSBM/week increased from 1.2 at baseline to 3.8 at fixed dose ($p=2.3\times10^{-8}$) and SBM increased from 2.6 at baseline to 4.5 at fixed dose ($p=6.4\times10^{-6}$) (Table 7). Use of rescue medication decreased from 1.8/week at baseline to 0.3 at fixed dose ($p=1.33\times10^{-5}$). Consistency based on the Bristol stool scale also improved, increasing from mean 2.7 to 4.1 (p=0.0001) and ease of passage increased from 3.2 to 3.7 (p=0.03). Subjective indices of wellbeing (PAC-QOL) and constipation symptoms (PAC-SYM) also improved during treatment (p=0.009 and p=0.03 respectively).

TABLE 7

Stool related indices Stage 2 (Dosed patients, n = 34)

| | Baseline (mean, SD) | Fixed dose (mean, SD) | P-value |
|---|---|---|---|
| CSBM* | 1.2 (0.90) | 3.8 (2.40) | $2.3 \times 10^{-8}$ |
| SBM* | 2.6 (1.45) | 4.5 (2.21) | $6.4 \times 10^{-6}$ |
| Suppository use* | 1.8 (1.92) | 0.3 (0.67) | $1.33 \times 10^{-5}$ |
| Consistency*** | 2.7 (1.20) | 4.1 (2.13) | 0.0001 |
| Ease of passage** | 3.2 (0.73) | 3.7 (1.19) | 0.03 |
| PAC-QOL total | 1.4 (0.49) | 1.2 (0.59) | 0.009 |
| PAC-SYM | 1.3 (0.45) | 1.1 (0.49) | 0.03 |

*weekly average;
**Ease of evacuation scale, where 1-manual disimpaction and 7 = incontinent;
***Bristol stool scale 1-7, where 1 = separate hard lumps and 7 = liquid consistency The dose that proved efficacious in inducing a bowel response was strongly related to constipation severity at baseline (p=0.00055) (FIG. 1B); patients with baseline constipation of <1 CSBM/week required higher doses for a response (mean 192 mg) than patients with ≥1 CSBM/week (mean 120 mg).

While the improvement in most stool-related indices did not persist beyond the treatment period, CSBM frequency remained significantly above baseline value (Table 8).

TABLE 8

Reversal of stool indices to baseline during the wash-out period (Stage 2)

| | Baseline (Mean, SD) | Fixed dose (Mean, SD) | Wash-out (Mean, SD) | P-value (wash-out vs. baseline) |
|---|---|---|---|---|
| CSBM | 1.2 (0.90) | 3.8 (2.4) | 1.8 (1.19) | 0.01 |
| SBM | 2.6 (1.45) | 4.5 (2.21) | 3.2 (1.80) | 0.16 |
| Ease | 3.2 (0.73) | 3.7 (1.19) | 3.3 (0.81) | 0.78 |
| Consistency | 2.7 (1.20) | 4.1 (2.13) | 2.8 (1.39) | 0.85 |
| Rescue meds | 1.8 (1.92) | 0.3 (0.67) | 1.0 (1.40) | 0.13 |
| PAQ-QOL | 1.4 (0.49) | 1.2 (0.59) | 1.2 (0.63) | 0.04 |
| PAQ-SYM | 1.3 (0.45) | 1.1 (0.49) | 1.1 (0.60) | 0.11 |

The primary efficacy outcome variable was whether or not a subject was a "success" or "failure". This is an endpoint based on subject diary entries for the "fixed dose" period prior to the endpoint assessment defined as average complete stool frequency increase by 1 or more over baseline, or 3 or more complete spontaneous stools/week. The subject was deemed a "success" if s/he met one or more of the criteria listed above, otherwise the subject was deemed a "failure". The primary analysis was based on all subjects with a baseline assessment and an assessment at the end of the "fixed-dose" period and was a comparison of the proportion of successes with 0.10 (the null hypothesis corresponding to no treatment effect).

The proportion of subjects for whom the drug was a success was estimated with a binomial point estimate and corresponding 95% confidence interval. A secondary analysis compared the proportions of subjects who are deemed a success at the end of the randomized fixed-dose period between those randomized to the squalamine (ENT-01) arm and those randomized to the placebo arm. A Fisher's exact test was used to compare the proportions of subjects who were deemed a success at the end of randomization period between the two randomized arms Subgroup Analysis:

Fifteen patients were randomized to treatment (n=6) or placebo (n=9) after the fixed dose period. During the 4-6 days of randomized treatment, the mean CSBM frequency in the treatment group remained higher than baseline as compared to those receiving placebo who returned to their baseline values (Table 9).

TABLE 9

CSBM frequency in the randomized cohort

| CSBM/week | Baseline | Fixed dose | Randomized | Washout |
|---|---|---|---|---|
| Treatment (n = 6) | 0.8 | 3.2 | 2.4 | 0.9 |
| Placebo (n = 9) | 1.6 | 3.3 | 1.4 | 1.6 |

CSBM increased in both groups during the treatment period and remained high in the treatment group during the randomized period but fell to baseline values in the placebo group.

Pharmacokinetics:

PK data were collected on the 10 patients enrolled in Stage 1 and 10 patients enrolled in Stage 2 to determine the extent of systemic absorption. In Stage 1, PK data were obtained at each visit, pre-medication, at 1, 2, 4, 8 and 24 hours (Table 10). In Stage 2, PK was measured on days 1 and 6 of the randomization period pre-medication, at 1, 2, 4 and 8 hours (Table 11). Based on the pharmacokinetic behavior of intravenously administered squalamine determined in prior clinical studies it is estimated that squalamine (ENT-01) exhibited oral bio-availability of less than 0.3% (Bhargava et al. 2001; Hao et al. 2003).

TABLE 10

Pharmacokinetics of orally administered squalamine (ENT-01) in Stage 1.
Stage 1

| Dose (mg) | # of patients | $C_{max}$ (ng/ml) | $T_{max}$ (hour) (Median Value) | $T_{1/2}$ (hours) (n) | $AUC_{0-8\,hr}$ (ng*hour/ml) | $AUC_{0-16\,hr}$ (ng*hour/ml) |
|---|---|---|---|---|---|---|
| 25 | 9 | 2.84 | 1.0 | 2.6 (3) | 10.8 | 19.6 |
| 50 | 10 | 3.73 | 2.0 | 3.4 (3) | 18.5 | 33.1 |
| 75 | 9 | 4.33 | 2.0 | 2.8 (2) | 18.4 | 29.8 |
| 100 | 9 | 6.18 | 2.0 | 3.9 (5) | 29.6 | 51.5 |
| 125 | 9 | 9.63 | 2.0 | 3.9 (4) | 43.1 | 77.7 |
| 150 | 7 | 6.27 | 2.0 | 5.6 (4) | 31.5 | 64.0 |
| 175 | 7 | 10.3 | 2.0 | 9.1 (6) | 49.7 | 91.2 |
| 200 | 6 | 15.1 | 2.0 | 9.0 (5) | 78.3 | 157 |

TABLE 11

Pharmacokinetics of orally administered squalamine (ENT-01) in Stage 2.
Stage 2

| Dose (mg) | # of patients (2 visits each) | $C_{max}$ (ng/ml) | $T_{max}$ (hour) (Median Value) | $T_{1/2}$ (hours) (n) | $AUC_{0-8\,hr}$ (ng*hour/ml) |
|---|---|---|---|---|---|
| 75 | 1 | 10.0 | 3.0 | 5.5 (1) | 59.0 |
| 100 | 4 | 17.7 | 1.0 | 4.8 (5) | 70.3 |
| 125 | | | | | |
| 150 | | | | | |
| 175 | 5 | 11.8 | 2.0 | 10 (6) | 66.8 |

The mean $C_{max}$, $T_{max}$ and $T_{1/2}$ and AUC of the squalamine ion following squalamine (ENT-01) oral dosing for Stage 1 patients. The PK analyses are only approximate, as the lower limit of the validated concentration range was 10 ng/ml; most of the measured concentrations fell below that value. The mean $C_{max}$, $T_{max}$ and $T_{1/2}$ and AUC of the squalamine ion following squalamine (ENT-01) oral dosing for Stage 2 patients. The PK analyses are only approximate, as the lower limit of the validated concentration range was 0.5 ng/ml.

CNS Symptoms in Stage 2:

An exploratory analysis was done with respect to the sleep data, the body temperature data, mood, fatigue, hallucinations, cognition and other motor and non-motor symptoms of PD. Continuous measurements within a subject were compared with a paired t-test and continuous measurements between subject groups were compared with a two-group t-test. Categorical data were compared with a chi-squared test or a Fisher's exact test if the expected cell counts are too small for a chi-squared test.

CNS Symptoms:

CNS symptoms were evaluated at baseline and at the end of the fixed dose period and the wash-out period (Table 12). Total UPDRS score was 64.4 at baseline, 60.6 at the end of the fixed dose period and 55.7 at the end of the wash-out period (p=0.002); similarly, the motor component of the UPDRS improved from 35.3 at baseline to 33.3 at the end of fixed dose to 30.2 at the end of wash-out (p=0.006). MMSE improved from 28.4 at baseline to 28.7 during treatment and to 29.3 during wash-out (p=0.0006). BDI-II decreased from 10.9 at baseline to 9.9 during treatment and 8.7 at wash-out (p=0.10). PDHQ improved from 1.3 at baseline to 1.8 during treatment and 0.9 during wash-out (p=0.03). Hallucinations were reported by 5 patients at baseline and delusions in 1 patient. Both hallucinations and delusions improved or disappeared in 5 of 6 patients during treatment and did not return for 4 weeks following discontinuation of squalamine (ENT-01) in 1 patient and 2 weeks in another. The frequency of arm or leg thrashing reported in the sleep diary diminished progressively from 2.2 episodes/week at baseline to 0 at maximal dose. Total sleep time increased progressively from 7.1 hours at baseline to 8.4 hours at 250 mg and was consistently higher than baseline beyond 125 mg (FIGS. 3, 4, and 5). Unlike stool-related indices, the improvement in many CNS symptoms persisted during wash-out.

TABLE 12

Effect of Squalamine (ENT-01) on neurological symptoms (n = 34)

| UPDRS | Baseline (Mean, SD) | Fixed dose (Mean, SD) | P-value | Wash-out (Mean, SD) | P-value |
|---|---|---|---|---|---|
| Part 1 (NMS) | 11.6 (6.51) | 10.6 (6.18)) | 0.28 | 9.5 (5.27) | 0.06 |
| Part 2 (Daily living) | 14.9 (8.11) | 14.7 (9.02) | 0.77 | 14.1 (8.21) | 0.40 |
| Part 3 (Motor) | 35.3 (14.35) | 33.3 (15.20) | 0.13 | 30.2 (13.23) | 0.005 |
| Total | 64.4 (23.72) | 60.6 (25.60) | 0.09 | 55.7 (23.69) | 0.002 |
| MMSE | 28.4 (1.75) | 28.7 (1.9) | 0.21 | 29.3 (1.06) | 0.0006 |
| PDHQ | 1.3 (2.99) | 1.8 (3.34) | 0.45 | 0.9 (2.33) | 0.03 |
| BDI-II | 10.9 (7.12) | 9.9 (6.45) | 0.14 | 8.7 (5.19) | 0.10 |

UPDRS: Unified Parkinson's Disease Severity Score;
NMS: Non-motor symptoms;
BDI: Beck Depression Index-II;
MMSE: Mini-mental State exam.
PDHQ: Parkinson's Disease Hallucination Questionnaire Circadian rhythm of skin temperature was evaluable in 12 patients (i.e., those who had recordings that extended from baseline through washout). Circadian system functionality was evaluated by continuously monitoring wrist skin temperature using a temperature sensor (Thermochron iButton DS1921H; Maxim, Dallas, Tex.) (Sarabia et al. 2008). A nonparametric analysis was performed for each participant to characterize DST as previously described (Sarabia et al. 2008; Ortiz-Tudela et al. 2010).

Briefly, this analysis includes the following parameters: (i) the inter-daily stability (the constancy of 24-hour rhythmic pattern over days, IS); (ii) intra-daily variability (rhythm fragmentation, IV); (iii) average of 10-minute intervals for the 10 hours with the minimum temperature (L10); (iv) average of 10-minute intervals for the 5 hours with the maximum temperature (M5) and the relative amplitude (RA), which was determined by the difference between M5 and L10, divided by the sum of both. Finally, the Circadian Function Index (CFI) was calculated by integrating IS, IV, and RA. Consequently, CFI is a global measure that oscillates between 0 for the absence of circadian rhythmicity and 1 for a robust circadian rhythm (Ortiz-Tudela et al. 2010).

A comparison was performed of circadian rhythm parameters during the baseline, fixed dose and washout periods. ENT-01 administration improved all markers of healthy circadian function, increasing rhythm stability (IS, p=0.026), relative amplitude (RA, p=0.001) and circadian function index (CFI, p=0.016), while reducing rhythm fragmentation (IV, p=0.031). The improvement persisted for several of these circadian parameters during wash-out period (IS, p=0.008 and CFI, p=0.004). (FIG. 7).

Conclusions:

This Phase 2 trial involving 50 patients with PD assessed the safety of orally administered ENT-01, and the effect on bowel function and neurologic symptoms of PD. In addition, the study aimed to identify a dose of ENT-01 that normalizes bowel function in each patient. The study achieved the objectives of identifying safety and pharmacodynamics responses of ENT-01 in PD. In addition, the study is the first proof of concept demonstration that directly targeting αS pharmacologically can achieve beneficial GI, autonomic and CNS responses.

The effective dose ranged between 75 mg and 250 mg, with 85% of patients responding within this range. This dose correlated positively with constipation severity at baseline consistent with the hypothesis that gastrointestinal dysmotility in PD results from the progressive accumulation of αS in the ENS, and that squalamine (ENT-01) can restore neuronal function by displacing αS and stimulating enteric neurons. These results demonstrate that the ENS in PD is not irreversibly damaged and can be restored to normal function.

Several exploratory endpoints were incorporated into the trial to evaluate the impact of ENT-01 on neurologic symptoms associated with PD. The UPDRS score, a global assessment of motor and non-motor symptoms, showed significant improvement. Improvement was also seen in the motor component. The improvement in the motor component is unlikely to be due to improved gastric motility and increased absorption of dopaminergic medications, since improvement persisted during the 2-week wash-out period, i.e., in the absence of study drug (Table 12).

Improvements were also seen in cognitive function (MMSE scores), hallucinations, REM-behavior disorder (RBD) and sleep. Six of the patients enrolled had daily hallucinations or delusions and these improved or disappeared during treatment in five. In one patient the hallucinations disappeared at 100 mg, despite not having reached the colonic prokinetic dose at 175 mg. The patient remained free of hallucinations for 1 month following cessation of dosing. RBD and total sleep time also improved progressively in a dose-dependent manner.

The prokinetic effect of the aminosterol squalamine appears to occur through local action of the compound on the ENS, since squalamine, the active zwitterion, is not significantly absorbed into the systemic circulation.

Example 2—Constipation

This prophetic example describes an exemplary method of (i) treating constipation associated with schizophrenia and/or (ii) treating and/or preventing schizophrenia in which constipation is a known symptom in a subject.

Schizophrenia patients are selected based on the constipation criteria described in Example 1. The patients are then subdivided into a control subgroup and a treatment subgroup. A "fixed dose" of an aminosterol or a salt or derivative thereof for each of the patients in the treatment subgroup is determined using the method described in Example 1 and in the application supra. Treatment and wash-out periods mirror Example 1. Schizophrenia patients are monitored for changes in the severity or occurrence of the symptoms. Schizophrenia patients are also monitored for changes in other symptoms associated with schizophrenia.

Schizophrenia patients having more severe constipation, e.g., less than 1 spontaneous bowel movement per week, are started at a dose of 75 mg or more. Schizophrenia patients having less severe constipation, e.g., 1 or more SBM/week, are started at a lower dose of aminosterol, e.g., a starting dose of less than 75 mg, for example a dose of 25 mg/day. Thus, the starting aminosterol dose is dependent upon constipation severity. The full aminosterol dosing range is from about 1 to about 500 mg. Once a fixed aminosterol dose has been identified for a schizophrenia patient, the schizophrenia subject is started at that same dose following drug cessation and reintroduction of drug dosing; e.g., there is no need to ramp up dosing once a fixed aminosterol dose for a patient has been identified.

Example 3—Hallucinations

This prophetic example describes an exemplary method of (i) treating hallucinations associated with schizophrenia and/or (ii) treating and/or preventing schizophrenia in which hallucinations are a known symptom in a subject.

Schizophrenia patients are selected based on having hallucinations. The patients are then subdivided into a control subgroup and a treatment subgroup. A "fixed dose" of an aminosterol or a salt or derivative thereof for each of the patients in the treatment subgroup is determined using the method described in Example 1, using the improvement of hallucination symptoms as an endpoint. Treatment and wash-out periods mirror Example 1. Schizophrenia patients are monitored for changes in the severity or occurrence of the symptoms.

Example 4—Depression

This prophetic example describes an exemplary method of (i) treating depression in schizophrenia patients and/or (ii) treating and/or preventing schizophrenia in which depression is a known symptom (a depression associated disorder, for example schizophrenia) in a schizophrenia subject having depression.

Schizophrenia patients are selected based on having depression. The patients are then subdivided into a control subgroup and a treatment subgroup. A "fixed dose" of an aminosterol or a salt or derivative thereof for each of the schizophrenia patients in the treatment subgroup is determined using the method described in Example 1, using the improvement of depression symptoms as an endpoint. Treatment and wash-out periods mirror Example 1. Schizophrenia patients are monitored for changes in the severity or occurrence of the symptoms.

Example 5—Circadian Rhythm Dysfunction

This prophetic example describes an exemplary method of (i) treating circadian rhythm dysfunction in a schizophrenia subject and/or (ii) treating and/or preventing schizophrenia in which circadian rhythm dysfunction is a known symptom (a circadian rhythm dysfunction associated disorder, for example schizophrenia) in a schizophrenia subject having circadian rhythm dysfunction.

Schizophrenia patients are selected based on having circadian rhythm dysfunction. The patients are then subdivided into a control subgroup and a treatment subgroup. A "fixed dose" of an aminosterol or a salt or derivative thereof for each of the schizophrenia patients in the treatment subgroup is determined using the method described in Example 1, using either the improvement of circadian rhythm dysfunction symptoms as an endpoint. Treatment and wash-out periods mirror Example 1. Patients are monitored for changes in the severity or occurrence of the symptoms.

Example 6—Schizophrenia

This prophetic example describes an exemplary method of treating and/or preventing schizophrenia in a subject in need thereof.

Schizophrenia patients are selected based on being diagnosed with schizophrenia, i.e., having schizophrenia, or exhibiting known risk factors of schizophrenia, i.e., at risk for developing schizophrenia. Patients are grouped based on having schizophrenia or at risk for developing schizophrenia. The groups are then subdivided into a control subgroup and a treatment subgroup. A "fixed dose" of an aminosterol or a salt or derivative thereof for each of the patients in the treatment subgroup is determined using the method described in Example 1, using either the improvement of constipation or another symptom of schizophrenia as an endpoint. Treatment and wash-out periods mirror Example 1. Patients are monitored for changes in the severity or occurrence of the symptoms. Patients having schizophrenia are monitored for changes in other symptoms associated with the disorder. Patients at risk for developing schizophrenia are monitored for the development of schizophrenia.

Example 7—Cognitive Impairment

This prophetic example describes an exemplary method of (i) treating cognitive impairment in schizophrenia subjects/or (ii) treating and/or preventing schizophrenia in which cognitive impairment is a known symptom.

Schizophrenia patients are selected based on having cognitive impairment. The patients are then subdivided into a control subgroup and a treatment subgroup. A "fixed dose" of an aminosterol or a salt or derivative thereof for each of the patients in the schizophrenia treatment subgroup is determined using the method described in Example 1, using the improvement of cognitive impairment symptoms as an endpoint. Treatment and wash-out periods mirror Example 1. Patients are monitored for changes in the severity or occurrence of the symptoms. Schizophrenia patients are also monitored for changes in other symptoms associated with schizophrenia.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

REFERENCES

Aarsland et al., "Neuropsychiatric symptoms in patients with Parkinson's disease and dementia: frequency, profile and associated care giver stress,"*J. Neurol. Neurosurg. Psychiatry*, 78:36-42 (2007).

Albert et al., "The Diagnosis of Mild Cognitive Impairment Due to Alzheimer's Disease: Recommendations from the National Institute on Aging—Alzheimer's Association Workgroups on Diagnostic Guidelines for Alzheimer's Disease," *Alzheimer's & Dementia*, 7(3):270-279 (2011).

Andresen et al., "Effect of 5 days linaclotide on transit and bowel function in females with constipation-predominant irritable bowel syndrome," *Gastroenterology*, 133:761-8 (2007).

Antonio-Rubio et al., "Abnormal thermography in Parkinson's disease," *Parkinsonism Relat. Disord.*, 21:852-7 (2015).

Auyeung et al., "Ten year survival and outcomes in a prospective cohort of new onset Chinese Parkinson's disease patients," *J. Neurol. Neurosurg. Psychiatry*, 83:607-11 (2012).

Benes F M, McSparren J, Bird E D, SanGiovanni J P, Vincent S L. "Deficits in small interneurons in prefrontal and cingulate cortices of schizophrenic and schizoaffective patients." Arch Gen Psychiatry. 1991; 48:996-1001.

Berg et al., "MDS Research Criteria for Prodromal Parkinson's Disease," *Mov. Disord.*, 30:1600-1611 (2015).

Bhargava et al., "A phase I and pharmacokinetic study of squalamine, a novel antiangiogenic agent, in patients with advanced cancers," *Clin. Cancer Res.*, 7:3912-9 (2001).

Braak et al., "Idiopathic Parkinson's disease: possible routes by which vulnerable neuronal types may be subject to neuroinvasion by an unknown pathogen," *J. Neural. Transm.* (Vienna), 110:517-36 (2003).

Braak et al., "Staging of brain pathology related to sporadic Parkinson's disease," *Neurobiol. Aging*, 24:197-211 (2003).

Braak et al., "Gastric alpha-synuclein immunoreactive inclusions in Meissner's and Auerbach's plexuses in cases staged for Parkinson's disease-related brain pathology," *Neuroscience Letters*, 396:67-72 (2006).

Breen et al., "Sleep and circadian rhythm regulation in early Parkinson disease," *JAMA Neurol.*, 71:589-95 (2014).

Breen, D. P. & Lang, A. E., "Tracking the Course of Prodromal Parkinson's Disease," *Brain*, 140:259-262 (2017).

Butler et al., "Dopamine Transporter Activity is Modulated by α-Synuclein," *J. of Biol. Chem.*, 290:29542-29554 (2015).

Chang et al., "A Meta-Analysis of Genome-Wide Association Studies Identifies 17 New Parkinson's Disease Risk Loci," *Nat. Genet.*, 49:1511-1516 (2017).

Cordell et al., "Alzheimer's Association Recommendations for Operationalizing the Detection of Cognitive Impairment During the Medicare Annual Wellness Visit in a Primary Care Setting," *Alzheimer's & Dementia*, 9(2): 141-150 (2013).

Darweesh et al., "Trajectories of Prediagnostic Functioning in Parkinson's Disease," *Brain*, 140:429-441 (2017).

Demirel, et al., "Decreased Expression of α-Synuclein, Nogo-A and UCH-L1 in Patients with Schizophrenia: A Preliminary Serum Study," *Psychiatry Investig.* 2017 May; 14(3): 344-349.

Diederich et al., "Hallucinations in Parkinson disease," *Nat. Rev. Neurol.*, 5:331-42 (2006).

Fahn S E R, Members of the UPDRS Development Committee. UNIFIED PARKINSON'S DISEASE RATING SCALE. Florham Park, N.J.: Macmillan Health Care Information (1987).

Frank et al., "Psychometric validation of a constipation symptom assessment questionnaire," *Scand. J. Gastroenterol.*, 34:870-7 (1999).

Friedman J H, Akbar U., "Psychosis in Parkinson's disease: unexplained observations in a seemingly simple model," *Expert Rev. of Neurotherapeutics*, 16:595-6 (2016).

Gjerstad et al., "Excessive daytime sleepiness in Parkinson disease: is it the drugs or the disease?" *Neurology*, 67:853-8 (2006).

Goetz C G, Stebbins G T., "Risk factors for nursing home placement in advanced Parkinson's disease," *Neurology*, 43:2227-9 (1993).

Gupta et al., "What is schizophrenia: A neurodevelopmental or neurodegenerative disorder or a combination of both? A critical analysis" *Indian J Psychiatry.* 2010 January-March; 52(1): 21-27.

Hao et al., "A Phase I and pharmacokinetic study of squalamine, an aminosterol angiogenesis inhibitor," *Clin. Cancer Res.*, 9:2465-71 (2003).

Heaton et al., "Defecation frequency and timing, and stool form in the general population: a prospective study," *Gut*, 33:818-24 (1992).

Holmqvist et al., "Direct evidence of Parkinson pathology spread from the gastrointestinal tract to the brain in rats," *Acta Neuropathol.*, 128:805-20 (2014).

Hughes et al., "Accuracy of clinical diagnosis of idiopathic Parkinson's disease: a clinico-pathological study of 100 cases," *J. Neurol. Neurosurg. Psychiatry*, 55:181-4 (1992).

Hughes et al., "Associations of Probable REM Sleep Behavior Disorder, Constipation, and Hyposmia with PD" (2017), in *Movement Disorder Society: Proceedings of the International Congress of Parkinson's Disease and Movement Disorders*; Marsili et al., 2018. Diagnostic Criteria for Parkinson's Disease: From James Parkinson to the Concept of Prodromal Disease. *Front. Neurol.*, Online 23 Mar. 2018.

Jack et al., "Introduction to the Recommendations from the National Institute on Aging—Alzheimer's Association Workgroups on Diagnostic Guidelines for Alzheimer's Disease," *Alzheimer's & Dementia*, 7(3):257-262 (2011).

Jennings et al., "Hyposmic and Dopamine Transporter-Deficit Prodromal Cohort," *JAMA Neurol.*, 74:933-940 (2017).

Jorm, A. F., "The Informant Questionnaire on Cognitive Decline in the Elderly (IQCODE): A Review," *International Psychogeriatrics*, 16:1-19 (2004).

Kirkevold, O. & Selbaek, G., "The Agreement Between the MMSE and IQCODE Tests in a Community-Based Sample of Subjects Aged 70 Years or Older Receiving In-Home Nursing: An Explorative Study," *Dement Geriatr. Cogn. Dis. Extra*, 5(1):32-41 (2015).

*Learning About Parkinson's Disease*, NIH Nat'l Human Genome Research Inst., *Parkinson Disease*, NIH U.S. Nat'l Library of Med.: Genetics Home Reference.

Lewis S J, Heaton K W., "Stool form scale as a useful guide to intestinal transit time," *Scand. J. Gastroenterol.*, 32:920-4 (1997).

Lin et al., "Risk of Parkinson's disease following severe constipation: a nationwide population-based cohort study," *Parkinsonism Relat. Disord.*, 20:1371-5 (2014).

Madrid-Navarro et al., "Multidimensional Circadian Monitoring by Wearable Biosensors in Parkinson's Disease," *Front. Neurol.*, 9:157 (2018).

Mahlknecht et al., "Prodromal Parkinson's Disease as Defined per MDS Research Criteria in the General Elderly Community," *Mov. Disord.*, 31:1405-1408 (2016).

Marquis et al., "Development and validation of the Patient Assessment of Constipation Quality of Life questionnaire," *Scand. J. Gastroenterol.*, 40:540-51 (2005).

Marsili et al., "Diagnostic Criteria for Parkinson's Disease: From James Parkinson to the Concept of Prodromal Disease," *Front. Neurol.*, Online 23 Mar. 2018.

Mearin et al., "Bowel Disorders," *Gastroenterology*, 150(6): 1393-1407 (2016).

McKhann et al., "The Diagnosis of Dementia Due to Alzheimer's Disease: Recommendations from the National Institute on Aging—Alzheimer's Association Workgroups on Diagnostic Guidelines for Alzheimer's Disease," *Alzheimer's & Dementia*, 7(3):263-269 (2011).

S. Morairty, "Detecting Neurodegenerative Diseases Before Damage Is Done," SRI International (Jul. 26, 2013).

Olney J W, Farber N B. "Glutamate receptor dysfunction and schizophrenia." *Arch Gen Psychiatry* 1995; 52:998-1007.

Ondo et al., "Daytime sleepiness and other sleep disorders in Parkinson's disease," *Neurology*, 57:1392-6 (2001).

Ondo et al., "Placebo-controlled trial of lubiprostone for constipation associated with Parkinson disease," *Neurology*, 78:1650-4 (2012).

Ortiz-Tudela et al., "Ambulatory circadian monitoring (ACM) based on thermometry, motor activity and body position (TAP): a comparison with polysomnography," *Physiol. Behav.*, 126:30-8 (2014).

Pagano, G., "Imaging in Parkinson's Disease," *Clin. Med.*, 16:371-375 (2016).

Palsetia et al., "The Clock Drawing Test versus Mini-mental Status Examination as a Screening Tool for Dementia: A Clinical Comparison," *Indian J. Psychol. Med.*, 40:1-10 (2018).

Papapetropoulos et al., "A questionnaire-based (U M-PDHQ) study of hallucinations in Parkinson's disease," *BMC Neurol.*, 8:21 (2008).

Perni et al., "A natural product inhibits the initiation of alpha-synuclein aggregation and suppresses its toxicity," *PNAS, USA*, 114:E1009-E17 (2017).

Phillips et al., "Alpha-synuclein-immunopositive myenteric neurons and vagal preganglionic terminals: autonomic pathway implicated in Parkinson's disease?" *Neuroscience*, 153:733-50 (2008).

Plassman et al., "Prevalance of Cognitive Impairment Without Dementia in the United States," *Ann. Intern. Med.*, 148(6):427-434 (2009).

Postuma et al., "The New Definition and Diagnostic Criteria of Parkinson's Disease," *Lancet Neurol.*, 15:546-548 (2016).

Postuma et al., "The New Definition and Diagnostic Criteria of Parkinson's Disease," *Lancet Neurol.* 15:546-548 (2016).

Rocca et al., "The Role of T1-Weighted Derived Measures of Neurodegeneration for Assessing Disability Progression in Multiple Sclerosis," *Front Neurol.*, 8:433 (Sep. 4, 2017).

Rund. "Is schizophrenia a neurodegenerative disorder?" *Nord J Psychiatry.* 2009; 63(3):196-201.

Sarabia et al., "Circadian rhythm of wrist temperature in normal-living subjects A candidate of new index of the circadian system," *Physiol. Behav.*, 95:570-80 (2008).

Shehata et al., "Neuronal stimulation induces autophagy in hippocampal neurons that is involved in AMPA receptor degradation after chemical long-term depression," *J. Neurosci.*, 32:10413-22 (2012).

Jon Stoessl, "Neuroimaging in the early diagnosis of neurodegenerative disease," *Transl. Neurodegener.*, 1: 5 (2012).

Steer et al., "Use of the Beck Depression Inventory-II with depressed geriatric inpatients," *Behav. Res. Ther.*, 38:311-8 (2000).

Stiasny-Kolster et al., "The REM sleep behavior disorder screening questionnaire—a new diagnostic instrument," *Movement disorders: Official J. of the Movement Dis. Soc.*, 22:2386-93 (2007).

Stolzenberg et al., "A Role for Neuronal Alpha-Synuclein in Gastrointestinal Immunity," *J. Innate Immun.*, 9:456-63 (2017).

Sumitomo et al., "A mouse model of 22q11.2 deletions: Molecular and behavior signatures of Parkinson's disease and schizophrenia," *Science Advances*, 4(8):eaar6637 (15 Aug. 2018).

Svensson et al., "Does vagotomy reduce the risk of Parkinson's disease: The authors reply" *Ann. Neurol.*, 78:1012-3 (2015).

Tang et al., "Loss of mTOR-Dependent Macroautophagy Causes Autistic-like Synaptic Pruning Deficits," *Neuron*, 83(5):1131-1143 (2014).

Videnovic A, Golombek D., "Circadian Dysregulation in Parkinson's Disease," *Neurobiol. Sleep Circadian Rhythms*, 2:53-8 (2017).

West et al., "Squalamine increases vagal afferent firing frequency in aging mice," J. of the Canadian Association of Gatroenterology, 1 (2018).

Wimo et al., "The worldwide economic impact of dementia 2010," *Alzheimer's Dement.*, 9: 1-11 (2013).

Wulff et al., "Sleep and circadian rhythm disruption in schizophrenia" *Br J Psychiatry.* 2012 April; 200(4): 308-316.

Zahodne et al., "Mood and motor trajectories in Parkinson's disease: multivariate latent growth curve modeling," *Neuropsychology*, 26:71-80 (2012).

Zinsmeister et al., "Pharmacodynamic and clinical endpoints for functional colonic disorders: statistical considerations," *Dig. Dis. Sci.*, 58:509-18 (2013).

What is claimed is:

1. A method of ameliorating the progression of schizophrenia (SZ) in a subject in need as measured by the amelioration of a symptom of SZ, wherein the subject has been diagnosed with SZ, and wherein the method comprises administering to the subject a therapeutically effective amount of at least one aminosterol or a salt thereof, wherein the aminosterol comprises:
   (a) squalamine or a pharmaceutically acceptable salt thereof; and/or
   (b) a squalamine phosphate salt; and/or
   (c) aminosterol 1436 or a pharmaceutically acceptable salt thereof; and/or
   (d) an aminosterol 1436 phosphate salt.

2. The method of claim 1, wherein the at least one aminosterol or a salt thereof is administered via a route selected from oral, nasal, sublingual, buccal, rectal, vaginal, intravenous, intra-arterial, intradermal, intraperitoneal, intrathecal, intramuscular, epidural, intracerebral, intracerebroventricular, transdermal, or any combination thereof.

3. The method of claim 1, wherein:
   (a) the at least one aminosterol or a salt thereof is administered nasally; and/or
   (b) the administration comprises non-oral administration.

4. The method of claim 1, wherein the therapeutically effective amount of the at least one aminosterol or a salt thereof:
   (a) comprises about 0.1 to about 20 mg/kg body weight of the subject; or
   (b) comprises about 0.001 to about 500 mg/day; or
   (c) comprises about 0.001 to about 6 mg/day administered intranasal.

5. The method of claim 1, wherein:
   (a) the subject is a human; and/or
   (b) the aminosterol or a salt thereof is taken on an empty stomach, optionally within two hours of the subject waking; or
   (c) no food is consumed or taken after about 60 to about 90 minutes of taking the aminosterol or a salt thereof; or (d) the aminosterol or a salt thereof is a pharmaceutically acceptable grade of at least one aminosterol or a pharmaceutically acceptable salt thereof.

6. The method of claim 1, wherein the aminosterol or the salt thereof is squalamine or a pharmaceutically acceptable salt thereof.

7. A method of ameliorating the progression of schizophrenia (SZ) in a subject in need as measured by the amelioration of a symptom of SZ, wherein the subject has been diagnosed with SZ, and wherein the method comprises administering to the subject a therapeutically effective amount of at least one aminosterol or a salt thereof, wherein the therapeutically effective amount is determined by a method comprising:
   (a) identifying a SZ symptom to be evaluated;
   (b) identifying a starting dose of the aminosterol or a salt thereof for the subject; and
   (c) administering an escalating dose of the aminosterol or a salt thereof to the subject over a first defined period of time until the therapeutically effective amount for the SZ symptom being evaluated is identified,
   wherein the therapeutically effective amount is the aminosterol dose where improvement or resolution of the SZ symptom is observed, and fixing the aminosterol dose at the therapeutically effective amount for that particular SZ symptom in that particular subject; and optionally
   (d) wherein the first defined period of time is selected from the group consisting of about 1 day to about 10 days, about 10 days to about 30 days, about 30 days to about 3 months, about 3 months to about 6 months, about 6 months to about 12 months, and greater than 12 months, and wherein the aminosterol is:
      (i) squalamine or a pharmaceutically acceptable salt thereof; and/or
      (ii) a squalamine phosphate salt; and/or
      (iii) aminosterol 1436 or a pharmaceutically acceptable salt thereof; and/or
      (iv) an aminosterol 1436 phosphate salt.

8. The method of claim 7, wherein the aminosterol or a salt thereof is administered orally, intranasally, or a combination thereof.

9. The method of claim 8, wherein the aminosterol or a salt thereof is administered orally and:
   (a) the starting dose of the aminosterol or a salt thereof ranges from 1 mg up to about 175 mg/day; and/or
   (b) the dose of the aminosterol or a salt thereof for the subject following escalation is fixed at a range of from 1 mg up to about 500 mg/day; and/or
   (c) the dose of the aminosterol or a salt thereof is escalated in about 25 mg increments.

10. The method of claim 8, wherein the aminosterol or a salt thereof is administered intranasally and:
    (a) the starting dose of the aminosterol or a salt thereof, prior to dose escalation, ranges from 0.001 mg to about 3 mg/day; and/or
    (b) the starting aminosterol dosage for IN administration, prior to dose escalation, is selected from the group consisting of about 0.001, about 0.005, about 0.01, about 0.02, about 0.03, about 0.05, about 0.06, about 0.07, about 0.08, about 0.09, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 1.0, about 1.1, about 1.25, about 1.3, about 1.4, about 1.5, about 1.6, about 1.7, about 1.75, about 1.8, about 1.9, about 2.0, about 2.1, about 2.25, about 2.3, about 2.4, about 2.5, about 2.6, about 2.7, about 2.75, about 2.8, about 2.9, and about 3 mg/day; and/or (c) the dose of the aminosterol or a salt thereof for the subject following escalation is fixed at a range of from 0.001 mg up to about 6 mg/day; and/or (d) the dose of the aminosterol or a salt thereof for the subject following escalation is a dose which is sub-therapeutic when administered orally or by injection; and/or (e) the dose of the aminosterol or a salt thereof is escalated in increments of about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

11. The method of claim 7, wherein:

(a) the dose of the aminosterol or a salt thereof is escalated every about 3 to about 5 days; and/or (b) the dose of the aminosterol or a salt thereof is escalated every about 1, about 2, about 3, about 4, about 5, about 6, about 7, about 8, about 9, about 10, about 11, about 12, about 13, or about 14 days; and/or (c) the dose of the aminosterol or a salt thereof is escalated about 1×/week, about 2×/week, about every other week, or about 1×/month; and/or (d) the therapeutically effective amount of the aminosterol or a salt thereof:

(i) is administered once per day, every other day, once per week, twice per week, three times per week, four times per week, five times per week, six times per week, every other week, or every few days; and/or (ii) administered for a first defined period of time of administration, followed by a cessation of administration for a second defined period of time, followed by resuming administration upon recurrence of SZ or a symptom of SZ; and/or (iii) is incrementally reduced after the fixed dose of aminosterol or a salt thereof has been administered to the subject for a period of time; and/or (e) each defined period of time is independently selected from the group consisting of about 1 day to about 10 days, about 10 days to about 30 days, about 30 days to about 3 months, about 3 months to about 6 months, about 6 months to about 12 months, and greater than 12 months.

12. The method of claim 7, wherein:

(a) progression of SZ is ameliorated over a defined period of time following administration of the fixed escalated dose of the aminosterol or a salt thereof, as measured by a medically-recognized technique; and/or (b) the SZ is positively impacted by the fixed escalated dose of the aminosterol or a salt thereof, as measured by a medically-recognized technique; and/or (c) the positive impact on and/or progression of SZ is measured quantitatively or qualitatively by one or more medically recognized techniques selected from the group consisting of The Clinical Assessment Interview for Negative Symptoms (CAINS), The Brief Negative Symptom Scale (BNSS), Scale for the Assessment of Positive Symptoms (SAPS), the Scale for the Assessment of Negative Symptoms (SANS), the Positive and Negative Symptoms Scale (PANSS), the Negative Symptom Assessment (NSA-16), the Clinical Global Impression Schizophrenia (CGI-SCH), computed tomography (CT), magnetic resonance imaging (MRI), magnetic resonance spectroscopy, functional MRI (fMRI), diffusion tensor imaging, single photon emission computed tomography (SPECT), and positron emission tomography (PET); and/or (d) the progression of SZ is ameliorated by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique; and/or (e) the fixed escalated dose of the aminosterol or a salt thereof reverses dysfunction caused by the SZ and ameliorates the SZ symptom being evaluated; and/or the amelioration of the schizophrenia symptom is measured using a clinically recognized scale or tool; and/or (g) the amelioration of the SZ symptom is 10%, 15%, 20%, 25%, 30%, 35%, 40%, 45%, 50%, 55%, 60%, 65%, 70%, 75%, 80%, 85%, 90%, 95%, or 100%, as measured using a clinically recognized scale or tool; and/or (h) each defined period of time is independently selected from the group consisting of about 1 day to about 10 days, about 10 days to about 30 days, about 30 days to about 3 months, about 3 months to about 6 months, about 6 months to about 12 months, and greater than 12 months.

13. The method of claim 7, wherein the SZ symptom to be evaluated is selected from the group consisting of:

(a) reduced social engagement, social withdrawal, and/or social isolation;

(b) reduced emotional expression;

(c) disorganized or irrational behavior;

(d) disorganized or irrational thinking;

(e) disorganized or irrational speech;

(f) aggression or anger;

(g) anxiety;

(h) compulsive behavior;

(i) excitability;

(j) repetitive movements;

(k) self-harm;

(l) delusions;

(m) amnesia;

(n) emotional instability;

(o) hallucinations;

(p) depression;

(q) constipation;

(r) neurodegeneration;

(s) sleep problem, sleep disorder, and/or sleep disturbance;

(t) cognitive impairment;

(u) feelings of fright and/or paranoia;

(v) distorted thoughts;

(w) lack of emotion or a very limited range of emotions;

(x) catatonia;

(y) impaired motor behavior and coordination;

(z) inability to make decisions;

(aa) forgetting or losing things;

(bb) poor executive functioning;

(cc) ADHD, trouble focusing, paying attention and/or difficulty concentrating;

(dd) difficulty with working memory;

(ee) lack of motivation;

(ff) reduced energy or apathy;

(gg) reduced speech;

(hh) loss of pleasure or interest in life;

(ii) poor hygiene and grooming habits;

(jj) hypertension;

(kk) sexual dysfunction, and/or
(ll) cardiovascular disease.

14. The method of claim 13, wherein the SZ symptom to be evaluated is hallucinations and wherein:
(a) the hallucinations comprise a visual, auditory, tactile, gustatory or olfactory hallucinations; and/or
(b) the method results in a decreased number of hallucinations over a defined period of time in the subject; and/or
(c) the method results in a decreased number of hallucinations over a defined period of time in the subject selected from the group consisting of by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or
(d) the method results in the subject being hallucination-free; and/or
(e) the method results in a decreased severity of hallucinations in the subject over a defined period of time, wherein the decrease in severity is measured by one or more medically-recognized techniques; and/or
the method results in a decreased severity of hallucinations in the subject over a defined period of time, wherein the decrease in severity is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as measured by one or more medically recognized techniques; and/or
(g) the one or more medically recognized techniques is selected from the group consisting of Chicago Hallucination Assessment Tool (CHAT), The Psychotic Symptom Rating Scales (PSYRATS), Auditory Hallucinations Rating Scale (AHRS), Hamilton Program for Schizophrenia Voices Questionnaire (HPSVQ), Characteristics of Auditory Hallucinations Questionnaire (CAHQ), Mental Health Research Institute Unusual Perception Schedule (MUPS), positive and negative syndrome scale (PANSS), scale for the assessment of positive symptoms (SAPS), Launay-Slade hallucinations scale (LSHS), the Cardiff anomalous perceptions scale (CAPS), and structured interview for assessing perceptual anomalies (SIAPA); and/or
(h) each defined period of time is independently selected from the group consisting of about 1 day to about 10 days, about 10 days to about 30 days, about 30 days to about 3 months, about 3 months to about 6 months, about 6 months to about 12 months, and greater than 12 months.

15. The method of claim 13, wherein the SZ symptom to be evaluated is depression and wherein:
(a) the method results in improvement in a subject's depression over a defined period of time, as measured by one or more clinically-recognized depression rating scales; and/or
(b) the method results in improvement in a subject's depression, over a defined period of time, as measured by one or more clinically-recognized depression rating scales and the improvement is in one or more depression characteristics selected from the group consisting of mood, behavior, eating, sleeping, energy, and sexual activity, episodes of sadness or apathy; and/or
(c) the method results in improvement in a subject's depression, over a defined period of time, as measured by one or more clinically-recognized depression rating scales, and the improvement a subject experiences following treatment is about 5, about 10, about 15, about 20, about 25, about 30, about 35, about 40, about 45, about 50, about 55, about 60, about 65, about 70, about 75, about 80, about 85, about 90, about 95 or about 100%; and/or
(d) wherein each defined period of time is independently selected from the group consisting of about 1 day to about 10 days, about 10 days to about 30 days, about 30 days to about 3 months, about 3 months to about 6 months, about 6 months to about 12 months, and greater than 12 months.

16. The method of claim 13, wherein the SZ symptom to be evaluated is cognitive impairment, and wherein:
(a) progression or onset of the cognitive impairment is slowed, halted, or reversed over a defined period of time following administration of the fixed escalated dose of the aminosterol or a salt thereof, as measured by a medically-recognized technique; and/or
(b) the cognitive impairment is positively impacted by the fixed escalated dose of the aminosterol or a salt thereof, as measured by a medically-recognized technique; and/or
(c) the cognitive impairment is positively impacted by the fixed escalated dose of the aminosterol or a salt thereof, as measured by a medically-recognized technique and the positive impact on and/or progression of cognitive decline is measured quantitatively or qualitatively by one or more techniques selected from the group consisting of ADASCog, Mini-Mental State Exam (MMSE), Mini-cog test, Woodcock-Johnson Tests of Cognitive Abilities, Leiter International Performance Scale, Miller Analogies Test, Raven's Progressive Matrices, Wonderlic Personnel Test, IQ tests, or a computerized tested selected from Cantab Mobile, Cognigram, Cognivue, Cognision, and Automated Neuropsychological Assessment Metrics Cognitive Performance Test(CPT); and/or
(d) the progression or onset of cognitive impairment is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique; and/or
(e) each defined period of time is independently selected from the group consisting of about 1 day to about 10 days, about 10 days to about 30 days, about 30 days to about 3 months, about 3 months to about 6 months, about 6 months to about 12 months, and greater than 12 months.

17. The method of claim 13, wherein the SZ symptom to be evaluated is constipation, and wherein:
(a) ameliorating the constipation ameliorates the progression of the schizophrenia; and/or
(b) the fixed escalated aminosterol dose causes the subject to have a bowel movement; and/or
(c) the method results in an increase in the frequency of bowel movement in the subject over a defined period of time; and/or
(d) the method results in an increase in the frequency of bowel movement in the subject and the increase in the frequency of bowel movement is defined as:
(i) an increase in the number of bowel movements per week of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or
   (ii) a percent decrease in the amount of time between each successive bowel movement selected from the group consisting of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%; and/or
(e) as a result of the method the subject has the frequency of bowel movement recommended by a medical authority for the age group of the subject; and/or
(f) the starting aminosterol dose is determined by the severity of the constipation, wherein:
   (i) if the average complete spontaneous bowel movement (CSBM) or spontaneous bowel movement (SBM) is one or less per week, then the starting aminosterol dose is 150 mg; and
   (ii) if the average CSBM or SBM is greater than one per week, then the starting aminosterol dose is about 75 mg or less; and/or
(g) wherein each defined period of time is independently selected from the group consisting of about 1 day to about 10 days, about 10 days to about 30 days, about 30 days to about 3 months, about 3 months to about 6 months, about 6 months to about 12 months, and greater than 12 months.

18. The method of claim 13, wherein the SZ symptom to be evaluated is neurodegeneration, and wherein:
(a) ameliorating the neurodegeneration ameliorates the progression of the SZ; and/or
(b) the method results in ameliorating the progression and/or onset of neurodegeneration in the subject; and/or
(c) progression or onset of the neurodegeneration is ameliorated over a defined period of time following administration of the fixed escalated dose of the aminosterol or a salt thereof, as measured by a medically-recognized technique; and/or
(d) the neurodegeneration is positively impacted by the fixed escalated dose of the aminosterol or a salt thereof, as measured by a medically-recognized technique; and/or
(e) the positive impact and/or progression of neurodegeneration is measured quantitatively or qualitatively by one or more techniques selected from the group consisting of electroencephalogram (EEG), neuroimaging, functional MM, structural Mill, diffusion tensor imaging (DTI), [18F]fluorodeoxyglucose (FDG) PET, agents that label amyloid, [18F]F-dopa PET, radiotracer imaging, volumetric analysis of regional tissue loss, specific imaging markers of abnormal protein deposition, multimodal imaging, and biomarker analysis; and/or
the progression or onset of neurodegeneration is ameliorated by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique; and/or
(g) each defined period of time is independently selected from the group consisting of about 1 day to about 10 days, about 10 days to about 30 days, about 30 days to about 3 months, about 3 months to about 6 months, about 6 months to about 12 months, and greater than 12 months.

19. The method of claim 13, wherein the SZ symptom to be evaluated is a sleep problem, sleep disorder, or sleep disturbance and:
(a) the sleep problem, sleep disorder, or sleep disturbance comprises a delay in sleep onset, sleep fragmentation, REM-behavior disorder, sleep-disordered breathing, snoring and apnea, day-time sleepiness, micro-sleep episodes, narcolepsy, circadian rhythm dysfunction, REM disturbed sleep, or any combination thereof; and/or
(b) the sleep problem, sleep disorder, or sleep disturbance comprises REM-behavior disorder, which comprises vivid dreams, nightmares, and acting out the dreams by speaking or screaming, or fidgeting or thrashing of arms or legs during sleep; and/or
(c) ameliorating the sleep problem, sleep disorder, or sleep disturbance ameliorates the progression of the schizophrenia; and/or
(d) the method results in a positive change in the sleeping pattern of the subject over a defined period of time; wherein the positive change is defined as:
   (i) an increase in the total amount of sleep obtained of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or
   (ii) a percent decrease in the number of awakenings during the night selected from the group consisting of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%; and/or
(f) as a result of the method the subject obtains the total number of hours of sleep recommended by a medical authority for the age group of the subject; and/or
(g) wherein each defined period of time is independently selected from the group consisting of about 1 day to about 10 days, about 10 days to about 30 days, about 30 days to about 3 months, about 3 months to about 6 months, about 6 months to about 12 months, and greater than 12 months.

20. The method of claim 7, wherein:
(a) the aminosterol or a salt thereof is administered in combination with at least one additional active agent to achieve either an additive or synergistic effect; and
(b) the additional active agent is administered via a method selected from the group consisting of concomitantly, as an admixture, separately and simultaneously or concurrently, and separately and sequentially; and/or
(c) the additional active agent is a different aminosterol from that administered in the method of claim 7; and/or
(d) the method comprises a first aminosterol which is aminosterol 1436 or a salt thereof administered intranasally and a second aminosterol which is squalamine or a salt thereof administered orally; and/or
(e) the additional active agent is an active agent used to treat schizophrenia or a symptom thereof; and/or
(f) the additional active agent is an active agent used to treat schizophrenia or a symptom thereof, wherein the active agent is selected from the group consisting of first-generation antipsychotics; atypical antipsychotics; and/or (g) the aminosterol or a salt thereof is taken on an empty stomach, optionally within two hours of the subject waking; and/or (h) no food is taken or consumed after about 60 to about 90 minutes of taking the aminosterol or a salt thereof; and/or (i) the aminosterol or a salt thereof is a pharmaceutically acceptable grade of at least one aminosterol or a pharmaceutically acceptable salt thereof; and/or (j) the aminosterol is comprised in a composition further comprising one or more of the following: an aqueous carrier; a buffer; a sugar; and/or a polyol compound; and/or (k) the subject is a human; and/or.

21. The method of claim 7, wherein the aminosterol or the salt thereof is squalamine or a pharmaceutically acceptable salt thereof.

22. The method of claim 1, wherein the aminosterol is a phosphate salt of squalamine.

23. The method of claim 1, wherein the aminosterol is aminosterol 1436 or a pharmaceutically acceptable salt thereof.

* * * * *